United States Patent [19]
Rorer

[11] Patent Number: 4,514,214

[45] Date of Patent: Apr. 30, 1985

[54] HERBICIDAL SULFAMATES

[75] Inventor: Morris P. Rorer, Newark, Del.

[73] Assignee: E. I. Du Pont de Nemours and Company, Wilmington, Del.

[21] Appl. No.: 637,783

[22] Filed: Aug. 6, 1984

Related U.S. Application Data

[60] Division of Ser. No. 473,322, Mar. 15, 1983, Pat. No. 4,475,944, which is a continuation-in-part of Ser. No. 386,680, Jun. 9, 1982, abandoned.

[51] Int. Cl.³ .................. C07D 403/12; A01N 43/66; C07D 413/12; C07D 417/12
[52] U.S. Cl. ......................................... 71/93; 544/212
[58] Field of Search ............................ 544/212; 71/93

[56] References Cited

U.S. PATENT DOCUMENTS 4,475,944 10/1984 Rorer ................................. 544/212

Primary Examiner—John M. Ford

[57] ABSTRACT

This invention relates to 2-(heterocyclic)phenyl sulfamates which are useful as agricultural chemicals.

36 Claims, No Drawings

HERBICIDAL SULFAMATES

RELATED APPLICATIONS

This is a divisional application of application Ser. No. 473,322, filed Mar. 15, 1983, now U.S. Pat. No. 4,475,944, which in turn is a continuation-in-part of my copending application U.S. Ser. No. 386,680, filed June 9, 1982, now abandoned.

BACKGROUND OF THE INVENTION

This invention relates to 2-(heterocyclic)phenyl sulfamates which are useful as agricultural chemicals.

U.S. Ser. No. 261,751 teaches that o-alkylsulfonyloxysulfamates are herbicidal.

DE No. 3,105,453 assigned to Hoechst AG teaches that phenoxysulfonylureas are herbicidal.

Netherlands Patent No. 121,788, published Sept. 15, 1966, teaches the preparation of the following compounds and their use as general or selective herbicides:

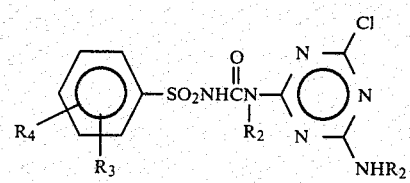

wherein
$R_1$ and $R_2$ may independently be alkyl of 1-4 carbon atoms; and
$R_3$ and $R_4$ may independently be hydrogen, chlorine or alkyl of 1-4 carbon atoms.

French Pat. No. 1,468,747 discloses para-substituted phenylsulfonamides, useful as antidiabetic agents:

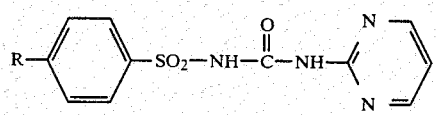

wherein
R=H, halogen, $CF_3$ or alkyl.

Logemann et al., Chem. Ab., 53, 18052 g (1959), disclose a number of sulfonamides, including uracil derivatives and those having the formula:

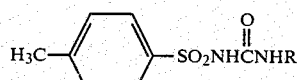

wherein
R is butyl, phenyl or

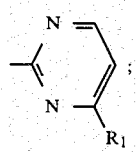

and
$R_1$ is hydrogen or methyl.

When tested for hypoglycemic effect in rats (oral doses of 25 mg/100 g), the compounds in which R is butyl and phenyl were most potent. The others were of low potency or inactive.

U.S. Pat. No. 4,191,553 discloses herbicidal compounds of the following formula:

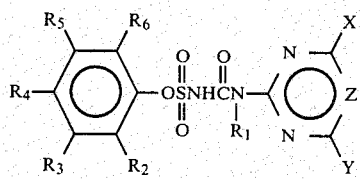

wherein
$R_1$ is H, $OCH_3$ or alkyl or 1-3 carbons;
$R_2$ is H, Cl, F, Br, $NO_2$, alkyl of 1-4 carbons, alkoxy of 1-4 carbons, $CF_3$ or

$R_3$ is H, Cl, F, Br, $CH_3$, or alkoxy of 1-4 carbons;
$R_4$ is H, Cl, F, Br, $NO_2$, alkyl of 1-4 carbons, alkoxy of 1-4 carbons, CN or

$R_5$ is H, Cl, F, Br, $CH_3$, $NO_2$ or $CF_3$;
$R_6$ is H, Cl, F, Br, alkyl of 1-4 carbons or alkoxy of 1-4 carbons;
$R_7$ is NavO-, OH, or alkoxy of 1-4 carbons;
X is $CH_3$, $CH_3CH_2$, alkoxy of 1-3 carbons, $CH_3OCH_2$, $CH_3OCH_2CH_2O$, $CH_3S$, $CH_3CH_2S$, $CF_3$ or Cl;
Y is $CH_3$, $CH_3CH_2$, alkoxy of 1-3 carbons, $CH_3OCH_2$, $CH_3OCH_2CH_2O$, $CH_3S$ or $CH_2CH_3S$; and
Z is CH or N;
provided that
only one of $R_2$, $R_3$ or $R_4$ is alkoxy; and
when $R_5$ is $NO_2$, $R_4$ is other than $NO_2$.

Wojciechowski, J. Acta. Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

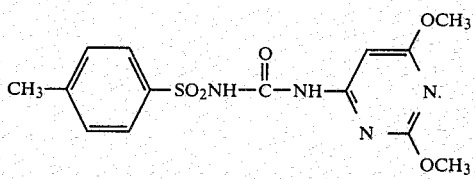

Based upon similarity to a known compound, the author predicted hypoglycemic activity for the foregoing compound.

The presence of undesired vegetation causes substantial damage to useful crops, especially agricultural products that satisfy man's basic food and fiber needs, such as cotton, rice, corn, wheat, soybean and the like. The current population explosion and concomitant world food and fiber shortage demand improvements in the efficiency of producing these crops. Preventing or minimizing the loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides. However, the need exists for still more effective herbicides that destroy or control weeds without causing significant damage to useful crops.

SUMMARY OF THE INVENTION

This invention relates to sulfamoylureas of Formula I, suitable agricultural compositions containing them and their method-of-use as general or selective pre-emergent or post-emergent herbicides or plant growth regulants.

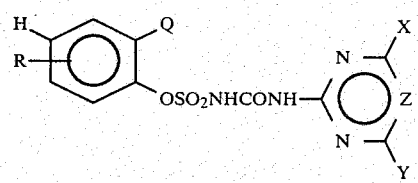

where

Q is

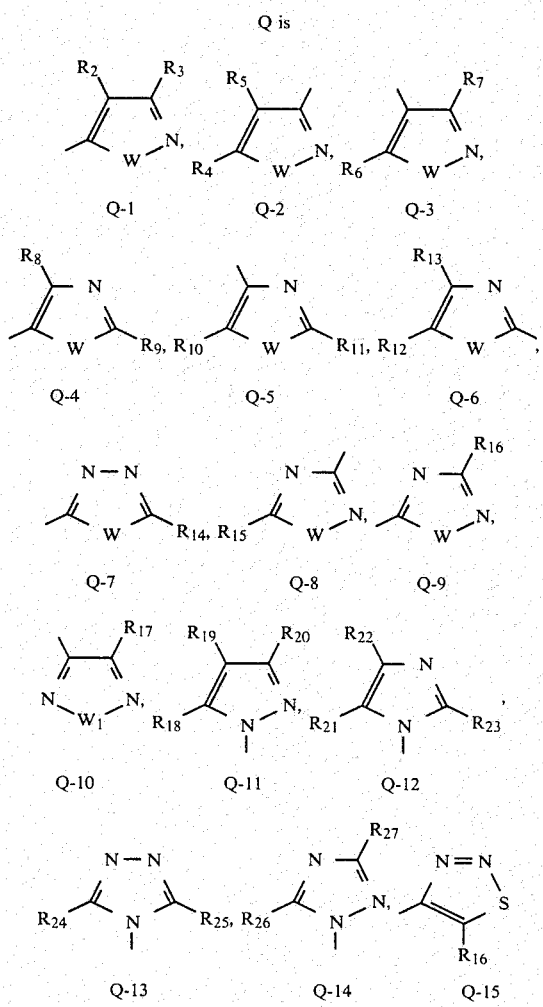

$R$ is H, F, Cl, Br, $CH_3$, $CF_3$ or $OCH_3$;

$W$ is O, S or $NR_1$;

$W_1$ is O or S;

$R_1$ is $C_1-C_3$ alkyl;

$R_2$, $R_3$, $R_4$, $R_5$, $R_8$, $R_9$, $R_{10}$, $R_{11}$, $R_{12}$, $R_{13}$, $R_{14}$, $R_{15}$, $R_{16}$, $R_{19}$, $R_{21}$, $R_{22}$, $R_{23}$, $R_{25}$ or $R_{27}$ are independently H, $CH_3$ or $C_2H_5$;

$R_6$, $R_7$, $R_{17}$, $R_{24}$ or $R_{26}$ are independently H or $CH_3$;

$R_{18}$ or $R_{20}$ are independently H or $C_1-C_3$ alkyl;

$X$ is Cl, $CH_3$, $OCH_3$, $OCF_2H$ or $SCF_2H$;

$Y$ is $CH_3$, $C_2H_5$, $OCH_3$, $OC_2H_5$, $OCH_2CF_3$, $CH_2OCH_3$, $CH(OCH_3)_2$ $$\begin{array}{c} \diagdown \\ \diagup \end{array} \!\!\! \begin{array}{c} O \\ O \end{array} \!\!\! ,$$

or $GCF_2T$ where G is O or S and

T is H, CHClF, CHBrF, $CF_2H$ or $CHFCF_3$; and Z is CH or N; provided that when X is Cl, then Z is CH and Y is $OCH_3$ or $OC_2H_5$; and their agriculturally suitable salts;

Preferred for their higher herbicidal activity, greater plant growth regulant activity or more favorable ease of synthesis are:

(1) Compounds of Formula I where R is H, W is O or S, and Q is Q-1 to Q-10, Q-15 and Q-16.

(2) Compounds of preferred 1 where $R_2$ to $R_{16}$, inclusive, are independently H or $CH_3$.

(3) Compounds of preferred 2 where

Q is ![structure with R2, R3, W, N]

(4) Compounds of preferred 2 where

Q is ![structure with R5, R4, W, N]

(5) Compounds of preferred 2 where

Q is ![structure with R7, R6, W, N]

(6) Compounds of preferred 2 where (7) Compounds of preferred 2 where

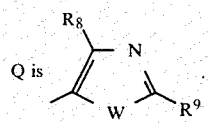

(8) Compounds of preferred 2 where

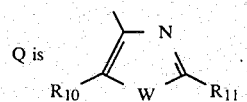

(9) Compounds of preferred 2 where

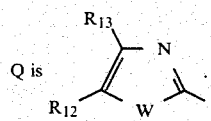

(10) Compounds of preferred 2 where

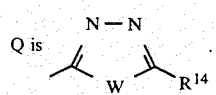

(11) Compounds of preferred 2 where

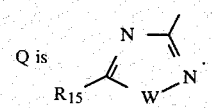

(12) Compounds of preferred 2 where

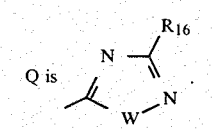

(13) Compounds of preferred 2 where

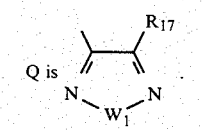

(14) Compounds of preferred 2 where

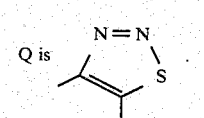

(15) Compounds of preferred 3 where
W is O.
(16) Compounds of preferred 4 where
W is O.
(17) Compounds of preferred 9 where
W is O.
(18) Compounds of preferred 2 where
X and Y are independently $CH_3$ or $OCH_3$.

Specifically preferred for their highest herbicidal activity, greatest plant growth regulant activity or most favorable ease of synthesis are:

2-(5-isoxazolyl)phenyl N-[(4,6-dimethoxypyrimidin-2-yl)aminocarbonyl]sulfamate;
2-(5-isoxazolyl)phenyl N-[(4-methoxy-6-methylpyrimidin-2-yl)aminocarbonyl]sulfamate;
2-(5-isoxazolyl)phenyl N-[(4,6-dimethylpyrimidin-2-yl)aminocarbonyl]sulfamate;
2-(5-isoxazolyl)phenyl N-[(4-methoxy-6-methyl-1,3,5-triazin-2-yl)aminocarbonyl]sulfamate;
2-(3-isoxazolyl)phenyl N-[(4,6-dimethoxypyrimidin-2-yl)aminocarbonyl]sulfamate;
2-(3-isoxazolyl)phenyl N-[(4-methoxy-6-methylpyrimidin-2-yl)aminocarbonyl]sulfamate;
2-(3-isoxazolyl)phenyl N-[(4,6-dimethylpyrimidin-2-yl)aminocarbonyl]sulfamate;
2-(3-isoxazolyl)phenyl N-[(4-methoxy-6-methyl-1,3,5-triazin-2-yl)aminocarbonyl]sulfamate;
2-(1,3,4-oxadiazol-2-yl)phenyl N-[(4,6-dimethoxypyrimidin-2-yl)aminocarbonyl]sulfamate;
2-(1,3,4-oxadiazol-2-yl)phenyl N-[(4-methoxy-6-methylpyrimidin-2-yl)aminocarbonyl]sulfamate;
2-(1,3,4-oxadiazol-2-yl)phenyl N-[(4,6-dimethylpyrimidin-2-yl)aminocarbonyl]sulfamate;
2-(1,3,4-oxadiazol-2-yl)phenyl N-[(4-methoxy-6-methyl-1,3,5-triazin-2-yl)aminocarbonyl]sulfamate;
2-(5-methyl-1,3,4-oxadiazol-2-yl)phenyl N-[(4,6-dimethoxypyrimidin-2-yl)aminocarbonyl]sulfamate; and
2-(1,3,4-oxadiazol-2-yl)-6-methylphenyl N-[(4,6-dimethoxypyrimidin-2-yl)aminocarbonyl]sulfamate.

DETAILED DESCRIPTION OF THE INVENTION

Synthesis

As shown in Equation 1 below, many compounds of Formula (I) can be prepared by reacting an aryloxysulfonyl isocyanate of Formula (III) with an appropriate 2-aminopyrimidine or 2-amino-1,3,5-triazine of Formula (IV).

Equation 1

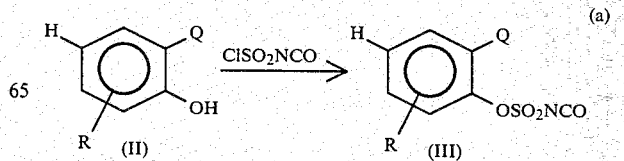

(a)

-continued
Equation 1

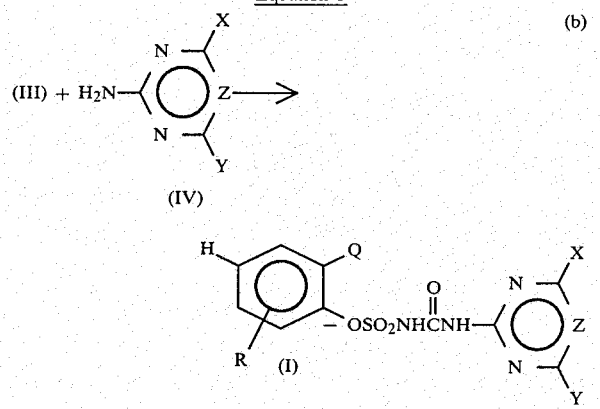

wherein R, X, Y and, Z are as originally defined; and Q is Q-1 to Q-10, Q-15 and Q-16; provided W is O or S.

Reaction 1b above is best carried out in an inert aprotic organic solvent such as methylene chloride, tetrahydrofuran or acetonitrile at ambient pressure and temperature. The mode of addition is not critical; however, it is convenient to add aryloxysulfonyl isocyanate III in solution to a stirred suspension of heterocyclic amine IV. The reaction is generally exothermic. In some cases the desired product is insoluble in the warm reaction medium and crystallizes from it in pure form. Products soluble in the reaction medium are isolated by evaporation of the solvent, trituration of the residue with solvents such as 1-chlorobutane, hexane, ethyl ether or ethy acetate, and filtration. The products may be further purified by recrystallization or chromatography procedures by methods well-known in the art.

The intermediate aryloxysulfonyl isocyanates of Formula (III) in reaction 1a above can be prepared by procedures similar to those described in Lohaus, Chem. Ber., 105, 2791 (1972) and U.S. Pat. No. 4,191,553. Thus, chlorosulfonyl isocyanate is reacted with an appropriate phenol of Formula (II) in an inert solvent such as toluene or xylene at about 15° to 40° C.; the resultant suspension is heated at about 80° to 135° C. for a short time to form III, e.g., at least 15 minutes. Preferably, the reaction is run in toluene, and the suspension is heated at reflux for only about 0.2 to 1 hour in order to reduce or prevent decomposition by-products. The aryloxysulfonyl isocyanate III is isolated by cooling the reaction suspension to room temperature, filtering to remove insoluble by-products and concentrating the filtrate in vacuo to yield III.

The compounds of Formula (I) may also be prepared as shown in Equation 2 below.

Equation 2

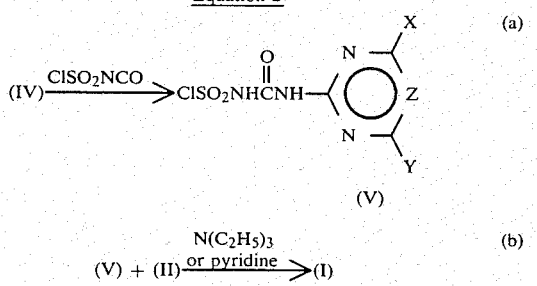

wherein R, X, Y, Z and Q are as originally defined.

According to reaction 2a above, chlorosulfonyl isocyanate is reacted with an appropriate heterocyclic amine of Formula (IV) to form a [(pyrimidin-2-yl)aminocarbonyl]sulfamoyl chloride or [(1,3,5-triazin-2-yl)aminocarbonyl]sulfamoyl chloride or Formula (V). The reaction is best carried out by adding one equivalent of chlorosulfonyl isocyanate to a suspension of amine IV in an inert aprotic solvent such as tetrahydrofuran, methylene chloride or acetonitrile at −40° C. to 10° C. The reaction is generally completed within one hour at 0° C. Unexamined European patent application No. 39,239 is hereby incorporated by reference for further details on the preparation and properties of sulfamoyl chlorides of Formula (V).

In reaction 2b above, the metastable intermediate sulfamoyl chlorides V are not isolated but are reacted directly with phenols of Formula (II) to form compounds I. The reaction is best carried out by adding one equivalent of phenol II followed by two equivalents of a suitable base such as pyridine or triethylamine to the suspension containing the freshly prepared sulfamoyl chloride V. It is preferred to carry out the addition at ambient temperature; pyridine is a preferred base. The reaction is run at about 20° to 50° C. for 1 to 48 hours, preferably at 20° to 30° C.

The desired product is isolated by (1) acidifying the reaction suspension with 10% hydrochloric acid or aqueous acetic acid to a pH of less than 7, (2) extracting the suspension with water to remove water soluble impurities, (3) drying and concentrating the organic phase in vacuo to yield compound I as a crude product, and (4) purifying the product by recrystallization or chromatography procedures by methods obvious to one skilled in the art.

Some of the ortho-heterocyclic phenols for Formula (II) in Equations 1 and 2 above can be preferred from appropriately substituted 2-hydroxyphenyl alkyl ketones, benzofuran-3-yl alkyl ketones or chromones by methods known in the art.

For instance, the 2-(1,2,3-thiadiazol-4-yl)phenols of Formula (IIa) below can be prepared by the method of U.S. Pat. No. 3,940,407. The method requires reacting an appropriate 2-hydroxyphenyl alkyl ketone with ethyl carbazate to form the corresponding hydrazide. Subsequent reaction of the hydrazide with thionyl chloride forms IIa.

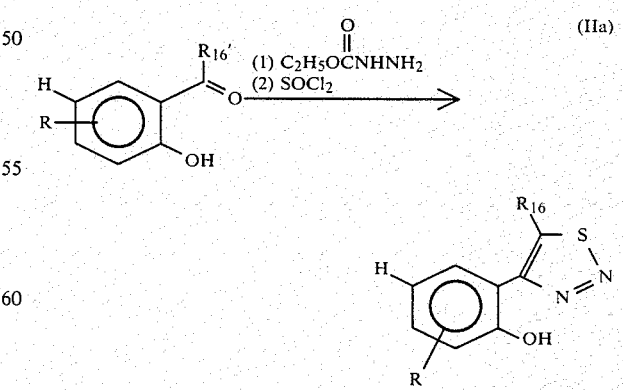

wherein R and $R_{16}$ are as defined above; and $R_{16}'$ is $C_1$–$C_3$ alkyl.

Similarly, the 2-(1,2,3-thiadiazol-5-yl)phenols of Formula (IIa') below are prepared by reacting an appropriate (2-hydroxyphenyl)acetaldehyde or ketone with ethyl carbazate followed by thionyl chloride, according to the general method of U.S. Pat. No. 3,940,407 described below.

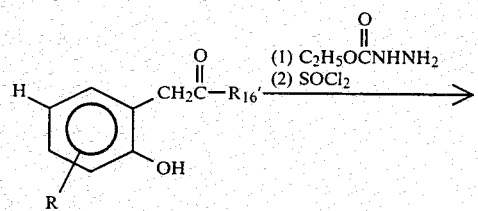

(IIa')

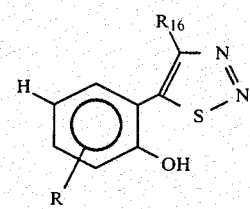

wherein R and $R_{16}$ are as defined above; and $R_{16}'$ is H, $CH_3$ or $C_2H_5$.

Also, the 2-(thiazol-4-yl)phenols of Formula (IIb) below can be prepared by reacting an appropriate 2-hydroxyphenyl α-haloalkyl ketone with an alkylthioamide, according to the teachings of R. Moffett, *J. Heterocycl. Chem.*, 17, 753, (1980).

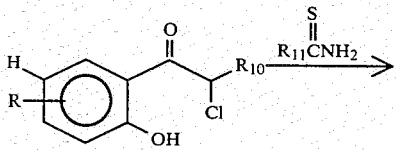

(IIb)

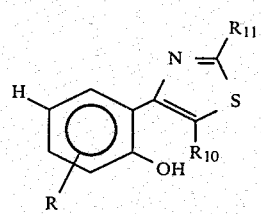

wherein R, $R_{10}$ and $R_{11}$ are as defined above.

Also, the 2-(1,3,4-oxadiazol-2-yl)phenols of Formula (IIc) below can be prepared by reacting an appropriate 2-hydroxybenzhydrazide with triethylorthoformate, triethylorthoacetate or triethylorthopropionate, according to the teachings of C. Runti et al., *Ann. Chim.*, 49, 1649 (1959) and F. Russo et al., *Boll. Chim. Farm.*, 105, 911 (1966).

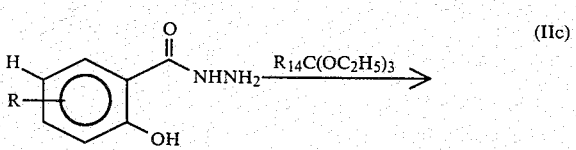

(IIc)

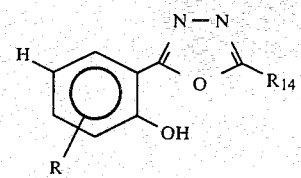

wherein R and $R_{14}$ are as defined above.

Also, the 2-(1,2,4-oxadiazol-3-yl)phenols of Formula (IId) below can be prepared by reacting a salicylamidoxime with an orthoformate described above or an appropriate alkyl acid chloride. For details refer to Shojiro et al., *Chem. Pharm. Bull.*, 21, 1885 (1973) and K. Harsanyi, *J. Heterocycl. Chem.*, 10, 957 (1973) and references therein.

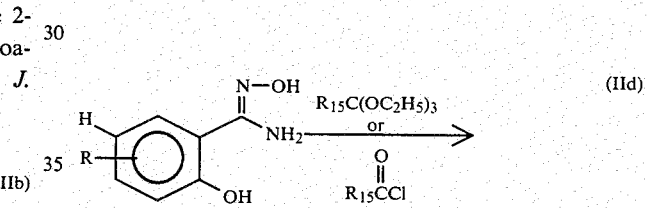

(IId)

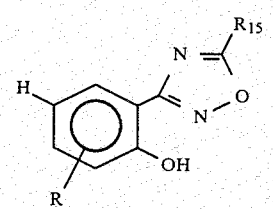

wherein R and $R_{15}$ are as defined above.

Also, the 2-(isoxazol-4-yl)phenols of Formula (IIe) and 2-(1-alkyl-1H-pyrazol-4-yl)phenols of Formula (IIf) below can be prepared by reacting an appropriate benzofuran-3-yl alkyl ketone with hydroxylamine or alkylhydrazine respectively. For details refer to *Neth. Applic.* 6,404,788; M. Descamps et al., *Bull. Soc. Chim. Belges.*, 73, 459 (1964); R. Royer et al. *Bull. Soc. Chim. France*, 59, 1746 (1963) and M. Hubert-Habart et al., ibid, 1587, (1966).

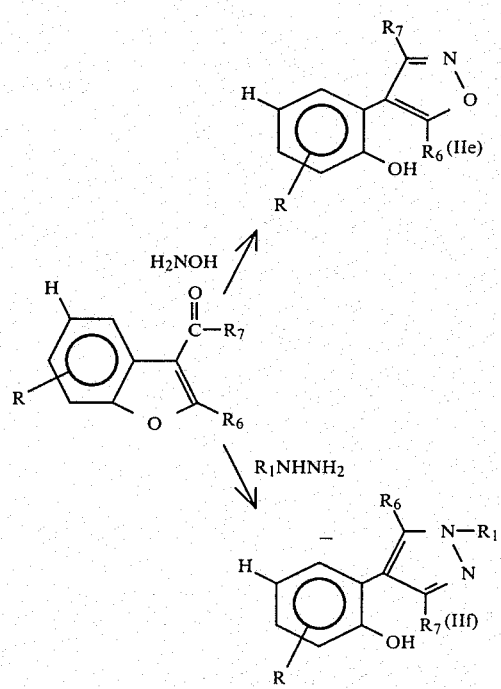

wherein
R₇ is CH₃; and
R, R₁ and R₆ are as defined above.

Also, the 2-(isoxazol-3-yl)phenols of Formula (IIg) and 2-(isoxazol-5-yl)phenols of Formula (IIh) below can be prepared by reacting an appropriate chromone with hydroxylamine. For details refer to R. Beugelmans et al., *J. Org. Chem.*, 42, 1356 (1977); V. Szabo et al., *Acta. Chim. Acad. Sci. Hung.*, 103, 271 (1980); ibid., 95, 333 (1977); A. Azim Sayed et al., ibid., 87, 165 (1975); and W. Basinski et al., *Pol. J. Chem.*, 53, 229 (1979).

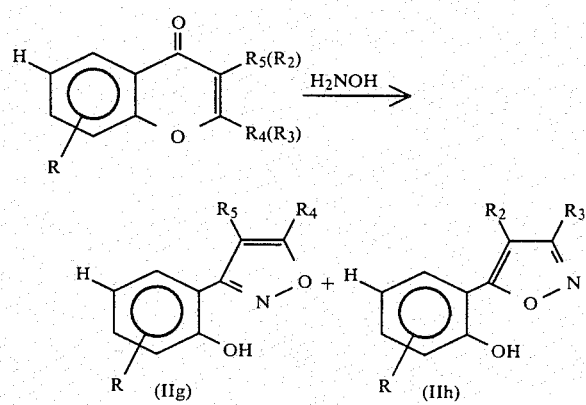

wherein R, R₂, R₃, R₄ and R₅ are as defined above.

In addition, certain other phenols of Formula (II) in Equations 1 and 2 above are known. For instance, 2-(isothiazol-4-yl)phenol can be prepared by the procedure of J. Finley et al., *J. Heterocycl. Chem.*, 6, 841 (1969); 2-(1,3,4-thiadiazol-2-yl)phenol by the procedure of M. Ohta et al., *J. Pharm. Soc. Japan*, 73, 701 and 852 (1953); 2-(1H-imidazol-1-yl)phenol by th procedure of L. Sitkina et al., *Khim. Geterotsikl. Soedin. Akad. Nauk. Latv. SSR*, 143 (1966) [*Chem. Abst.*, 65:13686 f]; 2-(1-methyl-1H-imidazol-2-yl)phenol by the procedure of G. Rogers et al., *J. Am. Chem. Soc.*, 96, 2463 (1974); 2-(1-methyl-1H-imidazol-3-yl)phenol by the procedure of C. Overberger, *J. Am. Chem. Soc.*, 93, 6992 (1971); and 2-(3,5-dimethyl-1H-pyrazol-1-yl)phenol by the procedure of V. Dziomko et al., *Tr. Vses. Nauchn-Isaled. Inst. Khim. Reaktivov.*, 25, 41 (1963) [*Chem. Abst.*, 60:15854 h].

As shown in Equation 3 below, still other phenols of Formula (II) in Equations 1 and 2 above can be prepared from ortho-(heterocyclic)benzeneamines of Formula (VI).

Equation 3

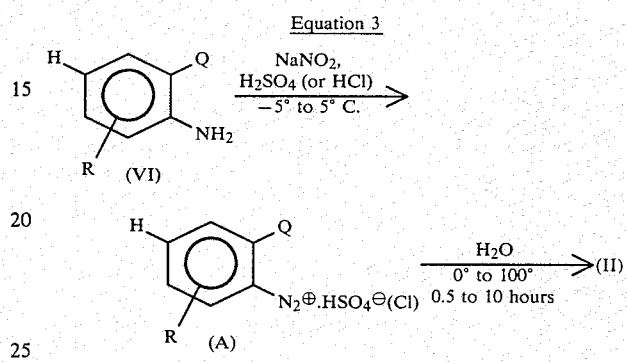

wherein R and Q are as defined above.

According to Equation 3 above, amine VI is diazotized in sulfuric acid or hydrochloric acid, preferably sulfuric acid, and the diazonium salt is reacted with water at 0° to 100° C. for about 0.5 to 10 hours to yield II. The preparation of phenols from benzeneamines via hydrolysis of diazonium salts is well known in the literature. For details, for instance, refer to A. I. Vogel, "Practical Organic Chemistry," p. 595 (1956), 3rd Edition; U.S. Pat. No. 3,270,029; J. H. Finley et al., *J. Het. Chem.*, 6, 841 (1969); M. Ohta et al., *J. Pharm. Soc. Japan*, 73, 701 (1953); and *Neth. Appl. No.* 6,602,601.

Some of the amines of Formula (VI) in Equation 3 above are known. For instance, 4-(2-aminophenyl)isothiazole may be prepared by the procedure of J. H. Finley, *J. Heterocycl. Chem.*, 6, 841 (1969); 2-(2-aminophenyl)-1,3,4-thiadiazole by the procedure of M. Ohta, *J. Pharm. Soc. Japan*, 73, 701 (1953); 2-(2-aminophenyl)-5-methyl-1,3,4-thiadiazole by the procedure of S. Leistner and G. Wagner, *Z. Chem.*, 14, 305 (1974); 2-(2-aminophenyl)-1,3,4-oxadiazole by the procedure of M. Vincent et al., *Bull. Soc. Chim. France*, 1580 (1962); 3-(2-aminophenyl)-5-methyl-1,2,4-oxadiazole by the procedure of H. Goncalves et al., *Bull. Soc. Chim. France*, 2599 (1970); 4-(2-aminophenyl)-1,2,4-triazole by the procedure of M. Khan and J. Polya, *J. Chem. Soc. C*, 85 (1970); and 3-methyl-4-(2-aminophenyl)-1,2,4-triazole and 3,5-dimethyl-4-(2-aminophenyl)-1,2,4-triazole by the procedure of W. Ried and H. Lohwasser, *Justus Liebigs Ann. Chem.*, 699, 88 (1966).

As shown in Equation 4 below, other amines of Formula (VI) can be prepared by reduction of corresponding nitrobenzenes of Formula (VII).

Equation 4

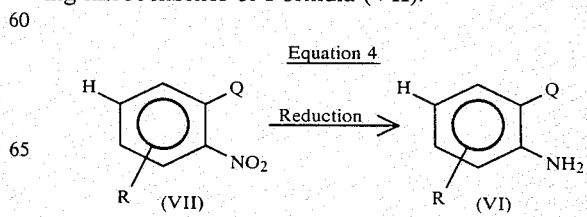

wherein

R and Q are as defined above.

The reduction reactions of Equation 4 above can be run by methods known in the literature by one skilled in the art. For instance, many of the reductions can be run by one or more of the following methods:

(a) with stannous chloride or tin and hydrochloric acid, either neat or in an inert solvent such as methanol, at about 25° to 80° C. for 0.5 to 10 hours. For details refer to similar procedures described in G. Corsi et al., *Boll. Chim. Farm.*, 103, 115 (1964); J. H. Finley, *J. Heterocycl. Chem.*, 6, 841 (1969); A. Quilico et al., *Gazz. Chim. Ital.*, 76, 87 (1946); and M. Khan and J. Polya, *J. Chem. Soc. C.*, 85 (1970).

(b) with ferrous sulfate heptahydrate and 28% ammonium hydroxide in an inert solvent such as aqueous ethanol at about 40° to 80° C. for about 1 to 2 hours. For details refer to similar procedures described in T. Naito et al., *Chem. Pharm. Bull.*, 16, 160 (1968); Neth. Appl. No. 6,608,094; and U.S. Pat. No. 3,341,518;

(c) with ammonium chloride and iron powder in an inert solvent such as water at 50° to about 80° C. for 1 to 3 hours. For details refer to a similar procedure described in M. Ohta et al., *J. Pharm. Soc. Japan*, 73, 701 (1953);

(d) with sodium hydrogen sulfide in an inert solvent such as methanol at about 40° to 70° C. for about 0.5 to 1 hour. For details refer to similar procedures described in G. Corsi et al., *Boll. Chim. Farm.*, 103, 115 (1964); and U.S. Pat. No. 3,270,029;

(e) by catalytic reduction with 5% palladium-on-charcoal, in the presence of 2 to 5 equivalents of aqueous hydrochloric acid, in an inert solvent such as ethanol at 25° to 45° C. at 1 to 3 atmospheres of hydrogen. For details refer to a similar procedure described in U.S. Pat. No. 3,910,942; and Ger. Offen. No. 2,415,978;

(f) by catalytic reduction with 5% Raney Nickel in an inert solvent such as ethanol or dioxane at 25° to 45° C. at 1 to 3 atmospheres of hydrogen. For details refer to similar procedures described in U.S. Pat. No. 3,270,029 and Neth. Appl. 6,513,932;

(g) by catalytic reduction with 5% palladium-on-charcoal in an inert solvent such as methanol at 25° to 45° C. at 1 to 3 atmospheres of hydrogen for short reaction times, i.e., less than 1 hour. For details refer to a similar procedure described in M. Vincent et al., *Bull. Soc. Chim. France*, 1580 (1962);

(h) by reduction with Raney Nickel catalyst and hydrazine hydrate in 95% ethanol at 25° to 80° C. for 0.2 to about 1 hour. For details refer to a similar procedure described in C. Ainsworth et al., *J. Med. Pharm. Chem.*, 5, 383 (1962);

(i) with sodium sulfide in 50% aqueous p-dioxane at about 25° to 80° C. for 0.25 to 1 hour, or with sodium sulfide and sodium bicarbonate in refluxing methanol for 1 to 10 hours. For details refer to Y. Lin and S. Lang, Jr., *J. Heterocycl. Chem.*, 17, 1273 (1980) and P. Smith and J. Boyer, *J. Am. Chem. Soc.*, 73, 2626 (1951) respectively; and, (j) with sodium hydrosulfite in ethanol-water at about 25° to 60° C. for 0.25 to 1 hour at a pH of less than 7. For details refer to U.S. Pat. No. 4,229,343.

The ortho-(heterocyclic)nitrobenzenes of Formula (VII) in Equation 4 above are important starting compounds for preparing the compounds I of this invention, which can be prepared by the following methods.

As shown in Equation 5 below, certain 5-(2-nitrophenyl)isoxazoles of Formula (VIIa) can be prepared by reacting a 2-nitrophenyl alkyl ketone of Formula (VIII) with an appropriate dimethylalkanamide dimethyl acetal of Formula (IX) to form a 3-dimethylamino-1-(2-nitrophenyl)-2-propen-1-one of Formula (X). Subsequent reaction of (X) with hydroxylamine hydrochloride provides VIIa.

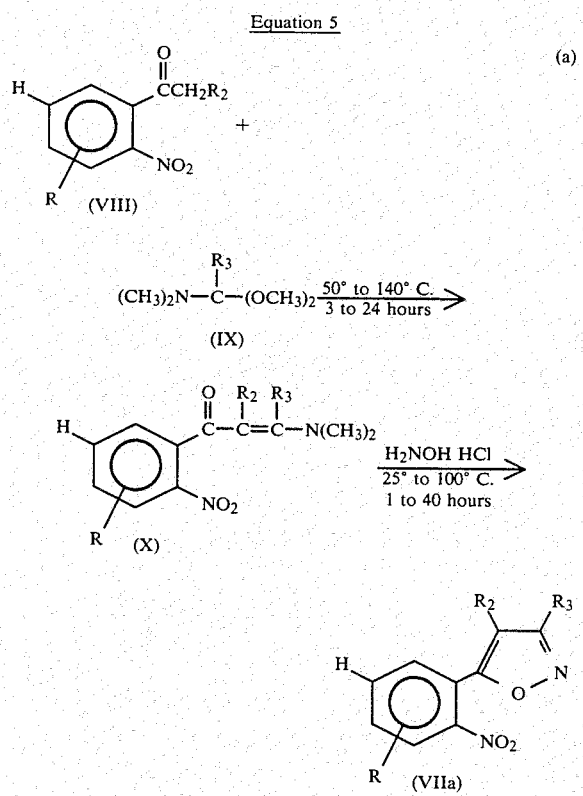

Equation 5 wherein

R, $R_2$ and $R_3$ are as defined above.

The reaction of Equation 5a is run at 50° to 140° C. for 3 to 24 hours in a solvent such as toluene or dimethylformamide or excess dimethyl alkanamide dimethyl acetal. The product can be isolated by evaporating the solvent. For more details, refer to similar procedures described in *Technical Information Bulletin*, "DMF Acetals", Aldrich Chemical, December 1973, and Lin and Lang, *J. Org. Chem.*, 45, 4857 (1980). The preparation of dimethyl alkanamide dialkyl acetals is reviewed in Abdulla and Brinkmeyer, *Tetrahedron*, 35, 1675 (1979).

The reaction of Equation 5b above is run in an inert solvent such as ethanol or aqueous dioxane at 25° to 100° C. for 1 to 48 hours. The product is isolated by addition of water and extraction with methylene chloride. For more details refer to similar procedures described in Lin and Lang, *J. Heterocycl. Chem.*, 14, 345 (1977).

As shown in Equation 6 below, 4-(2-nitrophenyl)isoxazoles of Formula (VIIb) can be prepared by reacting a 3-(dimethylamino)-2-(2-nitrophenyl)acrolein of Formula (XI) with hydroxylamine hydrochloride.

Equation 6

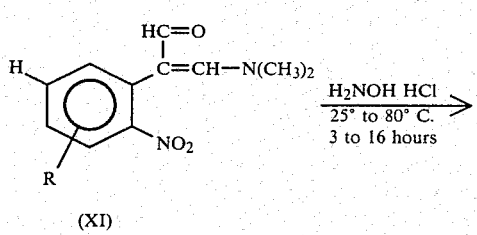

(XI)

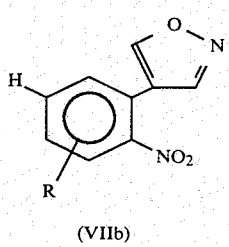

(VIIb)

wherein

R is as defined above.

The reaction of Equation 6 is run in ethanol at 25° to 80° C. for 3 to 16 hours. The product is isolated by addition of water and extraction with methylene chloride. The product is purified by recrystallization or column chromatography on silica gel. The starting material XI is prepared by known methods, e.g., U. Hengartner et al., *J. Org. Chem.*, 44, 3748 (1979).

5-Methyl-4-(2-nitrophenyl)isoxazoles of Formula (VIIb') can be prepared as shown in Equation 7 below. The method requires reacting a 2-nitrophenylpropanone of Formula (XII) with ethyl formate and sodium ethoxide to form a 3-oxo-2-(2-nitrophenyl)butyraldehyde of Formula (XIII). Subsequent reaction of XIII with hydroxylamine provides VIIb'.

Equation 7

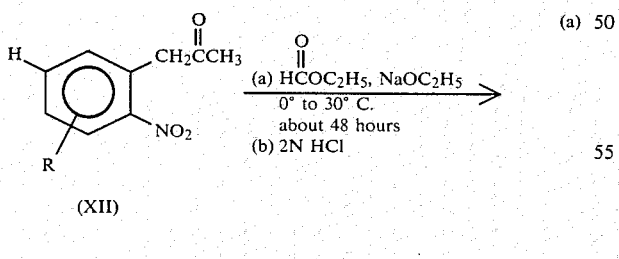

(XII)

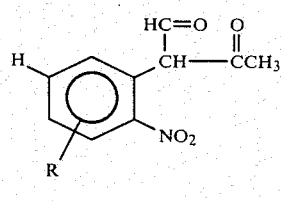

(XIII)

-continued
Equation 7

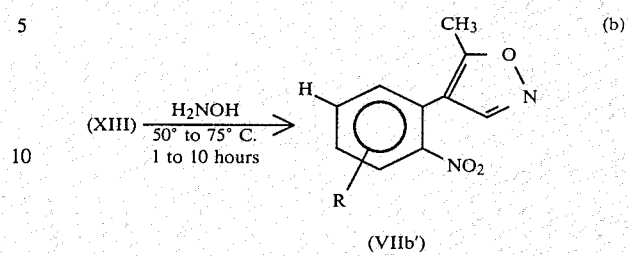

(VIIb')

wherein

R is as defined above.

The reaction of Equation 7a is run in ethanol at 0° to about 30° C. for about 48 hours. The product is isolated by addition of water and 2N HCl and extraction with methylene chloride. The reaction of Equation 7b is also run in ethanol at reflux for about 1 to 10 hours. The product is isolated by addition of water and extraction with methylene chloride. For more details refer to similar procedures described in H. Yasuda, *Yakugaku Zasshi*, 79, 623 (1959).

As shown in Equation 8 below, 3,5-dimethyl-4-(2-nitrophenyl)isoxazoles of Formula (VIIb'') can be prepared by reacting a 3-(2-nitrophenyl)pentan-2,4-dione of Formula (XIV) with hydroxylamine.

Equation 8

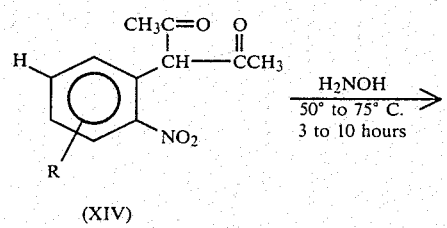

(XIV)

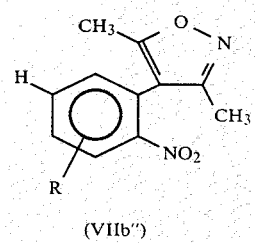

(VIIb'')

wherein

R is as defined above.

The reaction of Equation 8 is run in ethanol at 50° to 75° C. for about 3 to 10 hours. The product is isolated by addition of water and extraction with methylene chloride. For more details refer to similar procedures described in Bobranski and Wojtowski, *Roczniki Chem.*, 38, 1327 (1964).

Equation 9 below illustrates a method for preparing 3-(2-nitrophenyl)isoxazoles of Formula (VIIc).

Equation 9

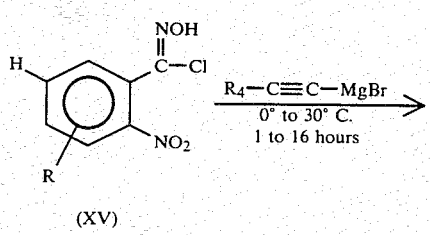

(XV)

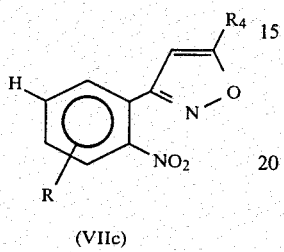

(VIIc)

wherein

R and $R_4$ are as defined above.

The reaction of Equation 9 is run by procedures similar to those taught by M. Langella et al., *Chim. Ind. (Milan)*, 47, 996 (1965) for the preparation of 3-(2-nitrophenyl)isoxazole, and by G. Gaudiano et al., *Gazz. Chim. Ital.*, 89, 2466 (1959) for the preparation of 5-ethoxy-3-(2-nitrophenyl)isoxazole. Thus, a 2-nitrophenylhydroxamic acid chloride of Formula (XV) is reacted with an appropriate acetylenic Grignard reagent in tetrahydrofuran at 0° to 30° C. for 1 to about 16 hours. The product is isolated by addition of water and ammonium chloride and extraction with methylene chloride. The acetylenic Grignard reagents are prepared from substituted acetylenes by procedures described in the cited references.

Equation 10 below illustrates a method for preparing 3-(2-nitrophenyl)isoxazoles of Formula (VIIc').

Equation 10

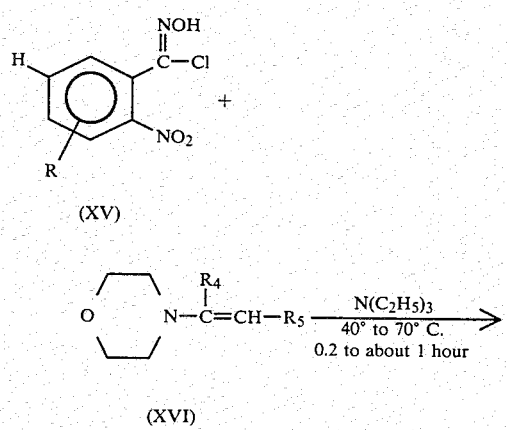

Equation 10 -continued

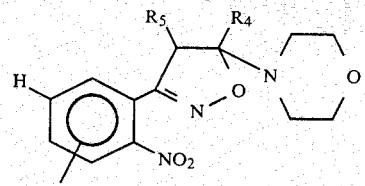

(XVII)

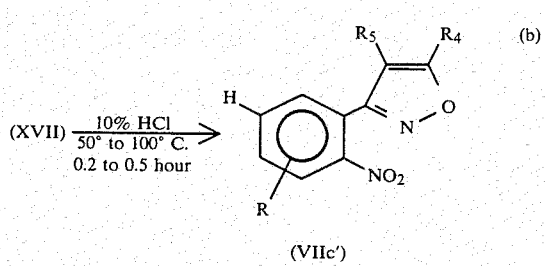

(VIIc')

wherein

R is as defined above;

$R_5$ is $CH_3$ or $C_2H_5$; and $R_4$ is H, $CH_3$ or $C_2H_5$.

The reactions of Equation 10 above can be run by procedures similar to those described in G. Bianchetti et al., *Gazz. Chim. Ital.*, 93, 1714 (1963) for the preparation of various 3-phenylisoxazoles. Thus, in reaction 10a, a 2-nitrophenylhydroxamic acid chloride of Formula (XV) is reacted with an equimolar amount of triethylamine and a N-alkenylmorpholine of Formula (XVI) in chloroform at reflux for 0.2 to about 1 hour to form a 5-(N-morpholinyl)-3-(2-nitrophenyl)isoxazoline of Formula (XVII). In reaction 10b, XVII is reacted with 10% hydrochloric acid at reflux for about 0.2 to 0.5 hour to form VIIc'. The product VIIc' is isolated by extraction with methylene chloride.

Equation 11 below illustrates a method for preparing 3-(2-nitrophenyl)isoxazoles of Formula (VIIc'').

Equation 11

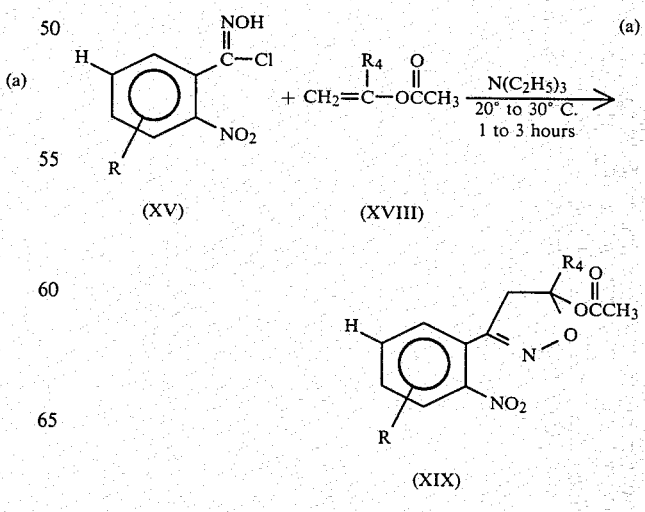

-continued
Equation 11

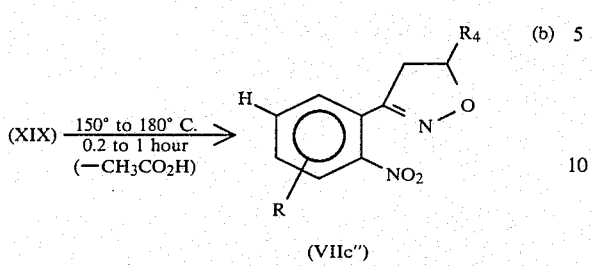

(VIIc'')

wherein

R and R₄ are as defined above.

The reactions of Equation 11 above can be run by procedures similar to those described in R. Micetich, *Can. J. Chem.*, 48, 467 (1970) for the preparation of various 3-phenylisoxazoles. Thus, in reaction 11a, a 2-nitrophenylhydroxamic acid chloride XV is reacted with equimolar amounts of a vinyl acetate of Formula (XVIII) and triethylamine in a solvent such as ether or tetrahydrofuran at about 30° C. for 1 to 3 hours to form a 5-acetoxy-3-(2-nitrophenyl)isoxazoline of Formula (XIX). In reaction 11b, XIX is heated at about 150° to 180° C. for a short period to form VIIc''.

The 5-(2-nitrophenyl)isothiazoles of Formula (VIId) in Equation 12 below can be prepared by methods analogous to those described in Yang-i Lin and S. A. Lang, *J. Org. Chem.*, 45, 4857 (1980) for the preparation of 5-phenylisothiazole.

Equation 12

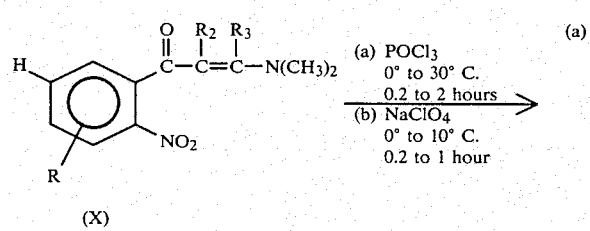

(X)

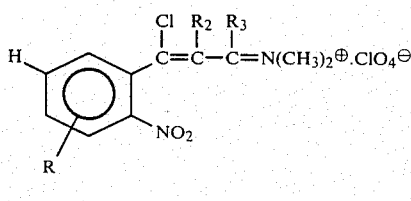

(XXI)

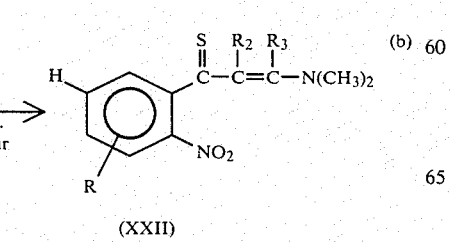

(XXII)

-continued
Equation 12

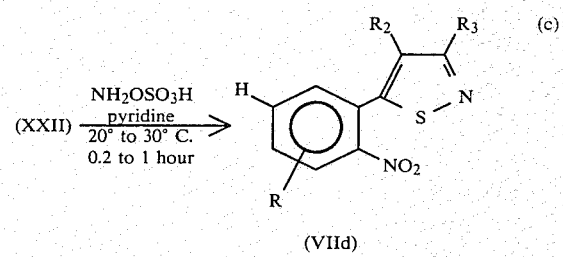

(VIId)

wherein

R, R₂ and R₃ are as defined above.

According to Equation 12 above, in reaction 12a a 3-dimethylamino-1-(2-nitrophenyl)-2-propen-1-one of Formula (X) is reacted with phosphorus oxychloride in methylene chloride at 0° to 30° C. for 0.2 to about 2 hours, followed by treatment with sodium perchlorate in water at 0° to 10° C. for 0.2 to about 1 hour to form a perchlorate salt of Formula (XXI). In reaction 12b, XXI is reacted with sodium sulfide nonahydrate in dimethylformamide and water at 0° to 10° C. for 0.2 to about 1 hour to form a 3-dimethylamino-1-(2-nitrophenyl)-2-propene-1-thione of Formula (XXII). And in reaction 12c, XXII is reacted with hydroxylamine-O-sulfonic acid (HSA) and two mole equivalents of pyridine in methanol at 20° to 30° C. for 0.2 to about 1 hour to form VIId.

The 4-(2-nitrophenyl)isothiazoles of Formula (VIIe) in Equation 13 below can be prepared by nitrating 4-phenylisothiazoles of Formula (XXIII) with concentrated nitric acid in concentrated sulfuric acid, according to the teachings of J. H. Finley and G. P. Volpp, *J. Heterocycl. Chem.*, 6, 841 (1969).

Equation 13

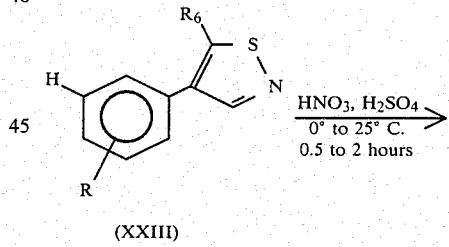

(XXIII)

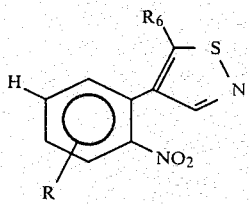

(VIIe)

wherein

R₆ is H or CH₃.

The reaction of Equation 13 above is run at 0° to 25° C. for 0.5 to 2 hours. The product VIIe is purified by column chromatography on silica gel. The starting compounds XXIII can be prepared by known methods. Several such methods are described in M. Muehlstaedt, *J. Prakt. Chem.*, 318, 507 (1976); M. Ohashi et al., *J.*

*Chem. Soc.*, 1148 (1970); R. A. Olofson et al., *Tetrahedron*, 22, 2119 (1966); and F. Huebenett et al., *Angew Chem.*, 75, 1189 (1963).

As shown in Equation 14 below, the 3-(2-nitrophenyl)isothiazoles of Formula (VIIf) and (VIIf') can be prepared by a series of procedures starting from a 2-nitrobenzonitrile of Formula (XXIV).

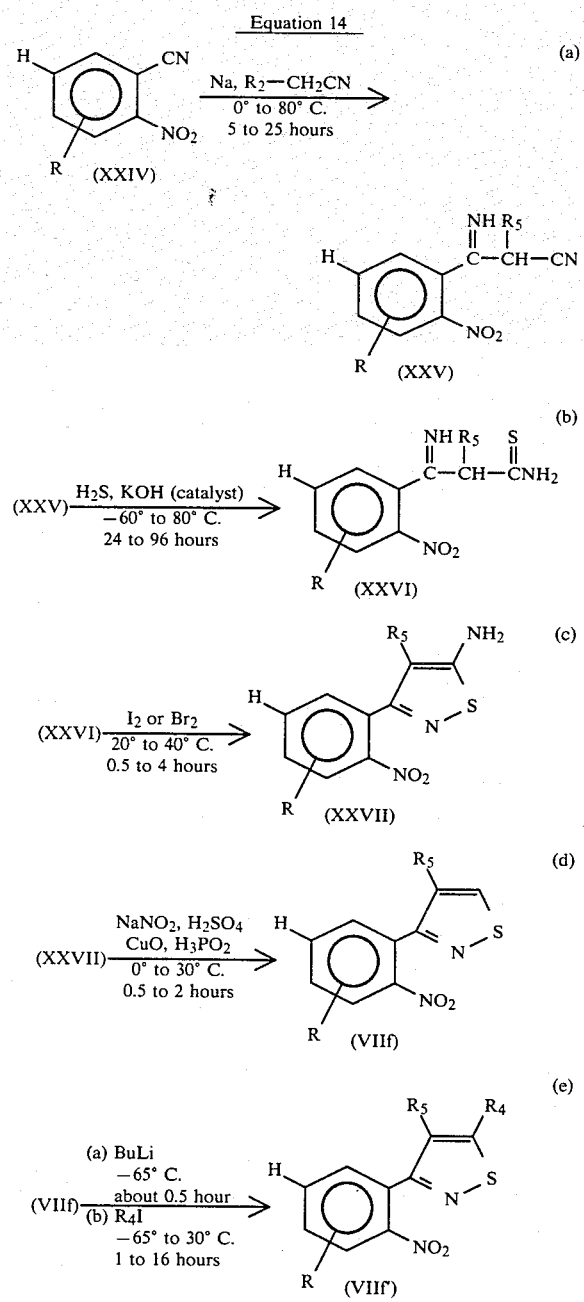

wherein
R, $R_4$ and $R_5$ are as defined above.

The reactions of Equation 14 above can be run by procedures known in the art. Thus, in reaction 14a, 2-nitrobenzonitrile XXIV can be reacted with an appropriate alkyl nitrile and sodium metal in a solvent such as ether or toluene at 0° to 80° C. for about 5 to 25 hours to form a 2-imino-2-(2-nitrophenyl)propionitrile of Formula (XXV), according to the teachings of U.S. Pat. No. 3,479,365; Netherlands No. 6,608,094; and T. Naito et al., *Bull. Chem. Soc. Japan*, 41, 965 (1968).

In the reaction of Equation 14b, XXV can be reacted with hydrogen sulfide and potassium hydroxide catalyst in methylene chloride at −60° C. to 80° C. in a sealed tube for 24 to 96 hours to form a 2-imino-2-(2-nitrophenyl)thiopropionamide of Formula (XXVI), according to the teachings of T. Naito et al., *Chem. Pharm. Bull.*, 16, 148 (1968) and J. Goerdeler and H. Pohland, *Chem. Ber.*, 94, 2950 (1961).

In the reaction of Equation 14c above, XXVI can be cyclized by reaction with iodine or bromine in a solvent such as ether, chloroform or ethanol containing potassium carbonate at 20° to 40° C. for 0.5 to 4 hours to form a 5-amino-3-(2-nitrophenyl)isothiazole of Formula (XXVII), according to the teachings of ibid., Netherlands 6,608,094 and J. Goerdeler and H. Pohland, *Angew Chem.*, 72, 77 (1962).

In the reaction of Equation 14d above, a diazonium salt, prepared from XXVII and sodium nitrite in sulfuric acid at 0° C. for 0.5 hour, can be reacted with cuprous oxide and 50% hypophosphorous acid at 0° to 30° C. for about 2 hours to form a 3-(2-nitrophenyl)isothiazole of Formula (VIIf), according to the teachings of M. Beringer et al., *Helv. Chim. Acta.*, 49, 2466 (1966).

And in the reaction of Equation 14e above, VIIf can be reacted with butyl lithium in tetrahydrofuran at −65° C. for about 0.5 hour to form a 5-lithio-3-(2-nitrophenyl)isothiazole reagent, according to the teachings of T. Naito et al., *Chem. Pharm. Bull.*, 16, 148 (1968). Subsequent reaction of this reagent with methyl or ethyl iodide, at −65° to 30° C. for 1 to 16 hours, can provide VIIf', according to the teachings of ibid.

Equation 15 below illustrates a method for preparing 3-(2-aminophenyl)-1H-pyrazoles of Formula (VIa) and 5-(2-aminophenyl)-1H-pyrazoles of Formula (VIb).

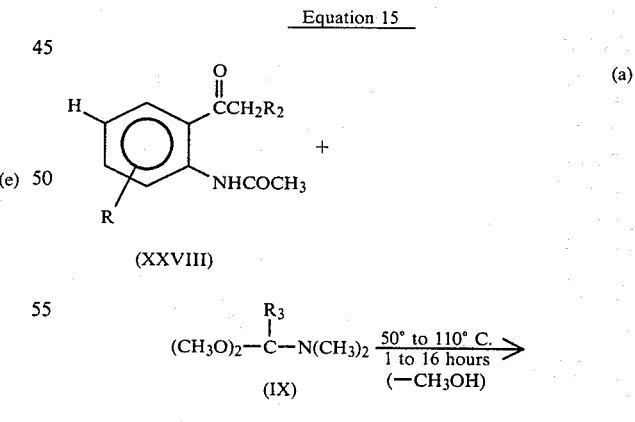

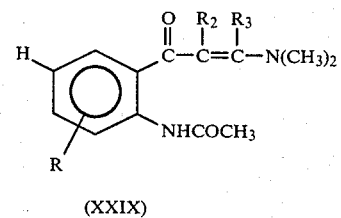

-continued
Equation 15

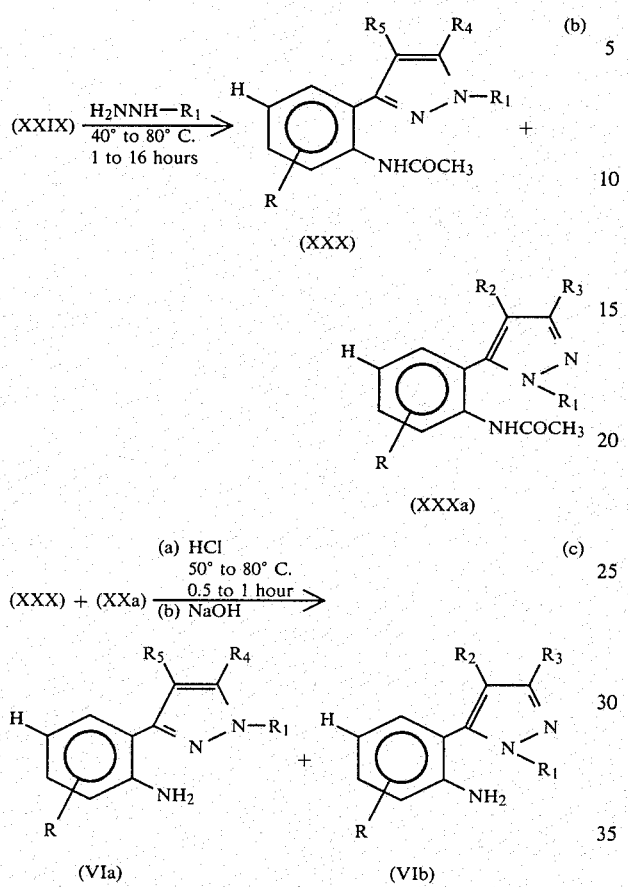

wherein

R, $R_1$, $R_2$, $R_3$, $R_4$ and $R_5$ are as defined above.

According to Equation 15 above, in reaction 15a, a 2-acetamidophenyl alkyl ketone of Formula (XXVIII) is reacted with a dimethylalkanamide dimethyl acetal of Formula (IX) to form a 3-dimethylamino-1-(2-acetamidophenyl)-2-propen-1-one of Formula (XXIX). The reaction can be run by procedures described above for the preparation of X in Equation 5a.

In the reaction of Equation 15b, XXIX is reacted with an appropriate hydrazine to form a mixture containing 3-(2-acetamidophenyl)-1H-pyrazole of Formula (XXX) and 5-(2-acetamidophenyl)-1H-pyrazole of Formula (XXXa). The reaction is run is ethanol at reflux for 1 to 16 hours. The product mixture is isolated by evaporation of the solvent.

And in the reaction of Equation 15c, amines VIa and VIb are obtained by acid hydrolysis of acetamides XXX and XXXa in the following manner. A mixture containing XXX and XXXa in concentrated hydrochloric acid is heated at reflux for about 1 hour, cooled and filtered. The solid, composed of hydrochloride salts of VIa and VIb, is neutralized in water with 50% NaOH. A mixture containing amines VIa and VIb is isolated by extraction with methylene chloride. The mixture can be reacted directly by procedures described in Equations 3 and then 2 above to provide corresponding compounds I of the invention as a mixture.

As shown in Equation 16 below, 4-(2-nitrophenyl)-1H-pyrazoles of Formula (VIIi) are prepared by reacting a 3-dimethylamino-2-(nitrophenyl)acrolein of Formula (XI) with an appropriate hydrazine.

Equation 16

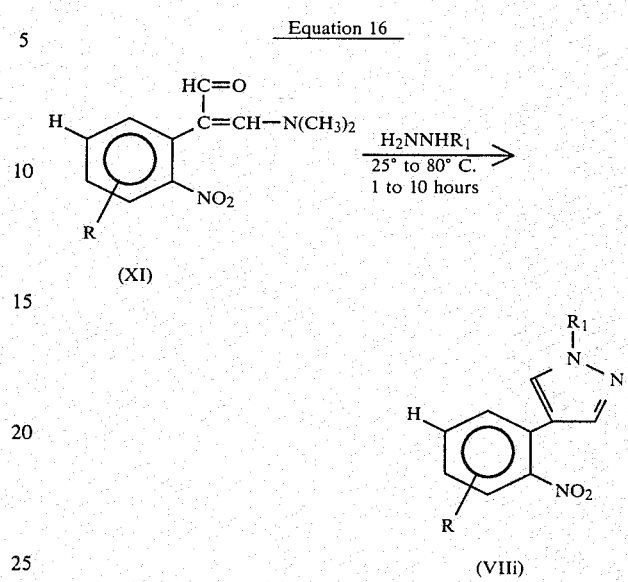

wherein

R and $R_1$ are as defined above.

The reaction of Equation 16 above is run in ethanol at 25° to 80° C. for 1 to 10 hours. The product is isolated by evaporation of the solvent and purified by recrystallization procedures.

As shown in Equation 17 below, a 3,5-dimethyl-4-(2-nitrophenyl)-1H-pyrazole of Formula (VIIi′) is prepared by reacting a 3-(2-nitrophenyl)pentan-2,4-dione of Formula (XIV) with an appropriate hydrazine. The reaction can be run by procedures described above in Equation 16.

Equation 17

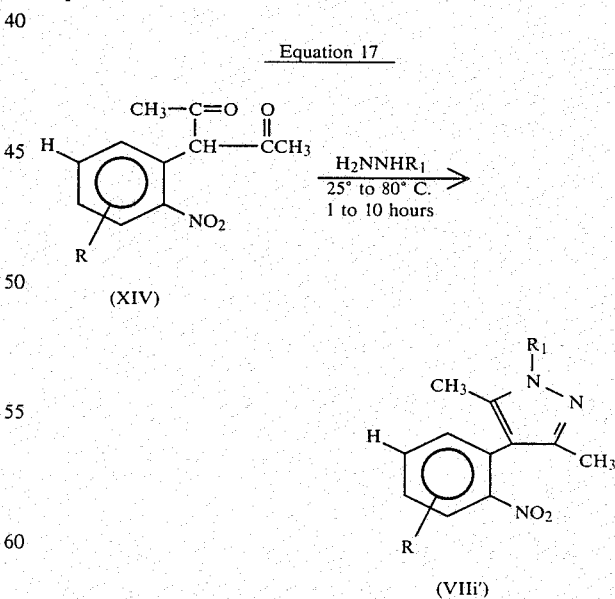

wherein

R and $R_1$ are as defined above.

A mixture containing 4-(2-nitrophenyl)-1H-pyrazoles of Formula (VIIi″) and (VIIi‴) can be prepared by reacting a 3-oxo-2-(2-nitrophenyl)butyraldehyde of Formula (XIII) with an appropriate hydrazine, as shown in Equation 18 below.

Equation 18

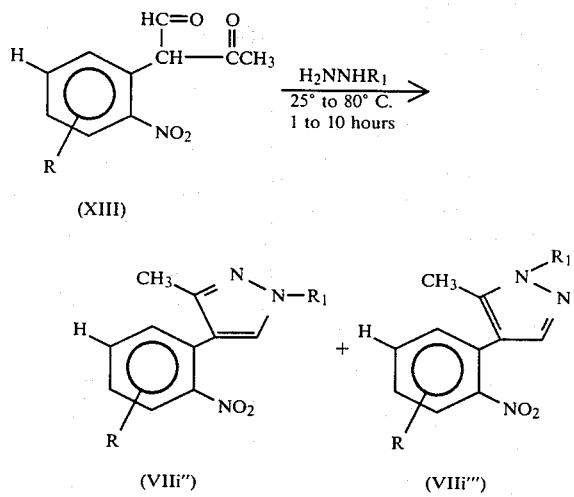

wherein
R and $R_1$ are as defined above.

The reaction of Equation 18 above can be run by procedures described in Equation 16 above. The product mixture can be transformed to a mixture of corresponding compounds I of the invention by a sequence of reactions described above in Equations 4, 3 and 2, respectively.

1-(2-Nitrophenyl)-1H-pyrazoles of Formula (VIIj) can be prepared as shown in Equation 19 below.

Equation 19

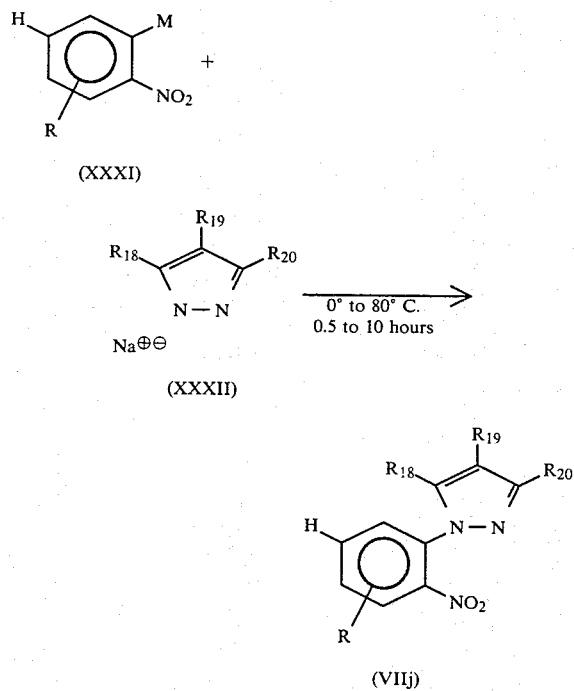

wherein
M is Cl, Br or F; and

R and $R_{18}$ to $R_{20}$ are as defined above.

According to Equation 19, a pyrazole sodium salt of Formula (XXXII) is reacted with a 2-halo-1-nitrobenzene of Formula (XXXI) to form VIIj. The reaction can be run in an aprotic solvent such as tetrahydrofuran or dimethylformamide at about 0° to 80° C. for 0.5 to 10 hours. The product is isolated by addition of water and extraction with methylene chloride. The product is purified by recrystallization or chromatography procedures. The sodium salt XXXII is formed by reacting an appropriate pyrazole with sodium hydride in situ by methods known in the art.

Many 1-(2-nitrophenyl)-1H-pyrazoles of Formula (VIIj) above can also be prepared by the Ullmann reaction, according to the teachings of M. Khan and J. Polya, *J. Chem. Soc. C.*, 85 (1970). This requires the reaction of a 2-halonitrobenzene, such as XXXI above, with an appropriately substituted pyrazole, copper (II) oxide catalyst and potassium carbonate in pyridine at reflux for 0.5 to several hours. The product is purified by column chromatography.

The 2-(2-nitrophenyl)-1,3,4-oxadiazoles of Formula (VIIk) in Equation 20 below can be prepared by reacting a 2-nitrobenzhydrazide of Formula (XXXIII) with excess triethylorthoformate at 100° to 150° C. for 5 to 24 hours, according to procedures described in U.S. Pat. No. 3,808,223.

Equation 20

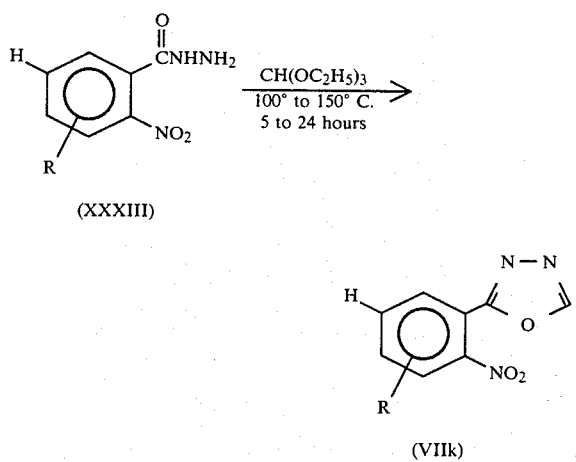

wherein
R is as defined above.

The 2-alkyl-5-(2-nitrophenyl)-1,3,4-oxadiazoles of Formula (VIIk') in Equation 21 below can be prepared by heating a 2-nitrobenzhydrazide of Formula (XXXIV) in excess phosphorus oxychloride at 70° to 100° C. for 0.5 to 2 hours, according to procedures described in ibid.

Equation 21

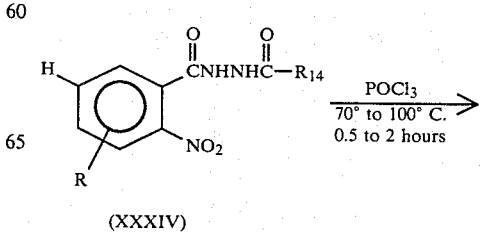

-continued
Equation 21

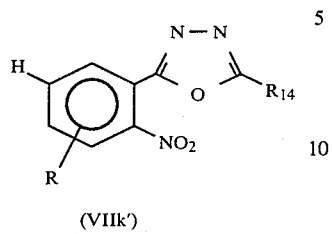

(VIIk')

wherein

R is as defined above; and $R_{14}$ is $CH_3$ or $C_2H_5$.

The 3-(2-nitrophenyl)-1,2,4-oxadiazoles of Formula (VIII) in Equation 22 below can be prepared by reacting a 2-nitrobenzamidoxime of Formula (XXXV) with excess triethylorthoformate at 100° to 150° C. for about 1 to 24 hours, according to the teachings of U.S. Pat. No. 3,910,942.

Equation 22

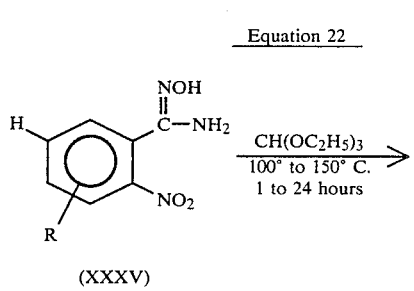

(XXXV)

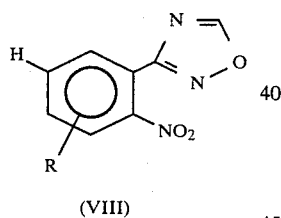

(VIII)

wherein

R is as defined above.

The 5-alkyl-3-(2-nitrophenyl)-1,2,4-oxadiazoles of Formula (VIII') in Equation 23 below can be prepared by reacting 2-nitrobenzamidoxime XXXV with an appropriate acid chloride in dioxane, with $BF_3 \cdot (C_2H_5)_2O$ catalyst, at 25° to 100° C. for about 1 to 18 hours, according to the teachings of ibid., or by reacting XXXV with acid chloride and pyridine in xylene at 25° to 130° C. for 0.5 to 5 hours, according to the teachings of U.S. Pat. No. 3,270,029. Also, VIII' can be prepared by reacting XXXV with excess anhydride at 100° to 150° C. for 0.5 to 5 hours, according to the teachings of ibid.

Equation 23

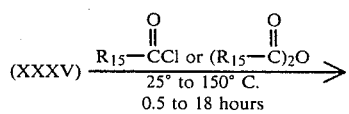

-continued
Equation 23

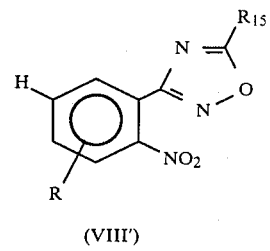

(VIII')

wherein

R is as defined above; and $R_{15}$ is $CH_3$ or $C_2H_5$.

The 5-(2-nitrophenyl)-1,2,4-oxadiazoles of Formula (VIIm) in Equation 24 below are prepared according to the teachings of Y. Lin et al., *J. Org. Chem.*, 44, 4160 (1979).

Equation 24

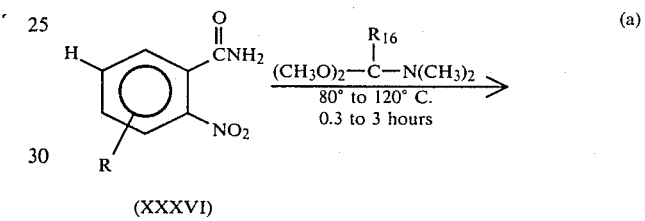

(XXXVI)

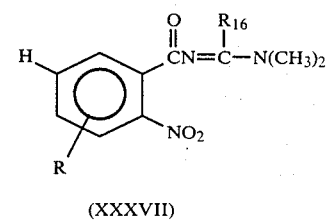

(XXXVII)

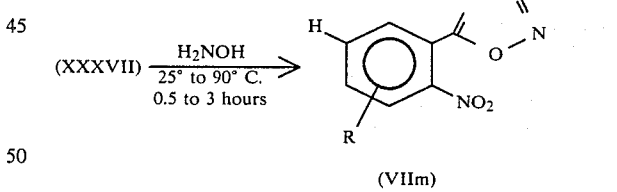

(VIIm)

wherein

R and $R_{16}$ are as defined above.

In the reaction of Equation 24a above, 2-nitrobenzamide XXXVI is reacted with excess dimethylalkanamide dimethyl acetal at 80° to 120° C. for about 0.3 to 3 hours to form a N-[(dimethylamino)methylene]benzamide of Formula (XXXVII). In reaction 24b, XXXVII is reacted with hydroxylamine in aqueous dioxane-acetic acid at 25° to 90° C. for 0.5 to 3 hours to form VIIm.

The 3-(2-nitrophenyl)-1,2,5-oxadiazoles of Formula (VIIn) in Equation 25 below can be prepared by heating a 2-nitrophenylglyoxime of Formula (XXXVIII) with 6N $NH_4OH$ in an autoclave at 150°–180° C. for 1 to 8 hours, according to the teachings of M. Milone, *Gazz. Chim. Ital.*, 63, 456 (1933).

Equation 25

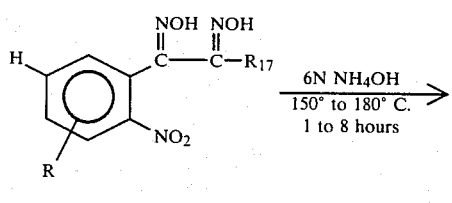

(XXXVIII)

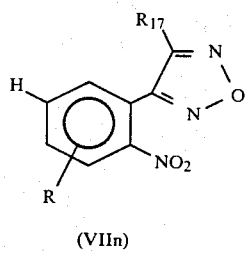

(VIIn)

wherein
R and $R_{17}$ are as defined above.

The 2-(2-nitrophenyl)-1,3,4-thiadiazoles of Formula (VIIo) in Equation 26 below can be prepared by reacting 2-nitrothiobenzhydrazide XXXIX with excess triethylorthoformate at reflux for 1 to 16 hours, according to the teachings of C. Ainsworth, *J. Am. Chem. Soc.*, 77, 1150 (1955).

Equation 26

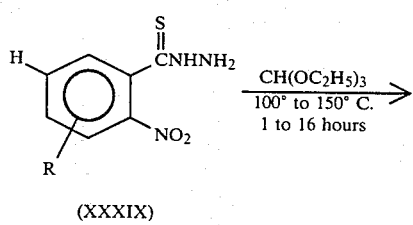

(XXXIX)

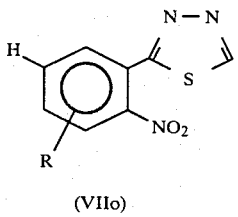

(VIIo)

wherein
R is as defined above.

The 2-alkyl-5-(2-nitrophenyl)-1,3,4-thiadiazoles of Formula (VIIo') in Equation 27 below can be prepared by reacting 2-nitrothiobenzhydrazide XXXIX with an appropriate alkylimidate ester HCl in a solvent such as ethanol at 25° to 80° C. for 0.5 to 5 hours, according to the teachings of H. Weidinger and J. Kranz, Ber., 96, 1059 (1963).

Equation 27

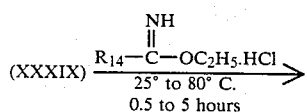

Equation 27 -continued

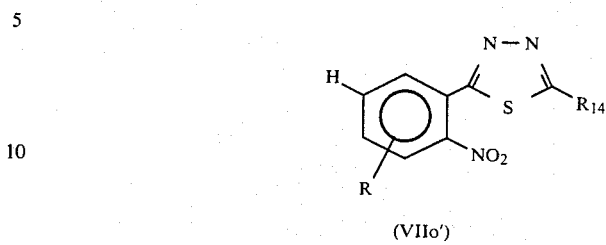

(VIIo')

wherein
R is as defined above; and
$R_{14}$ is $CH_3$ or $C_2H_5$.

Equation 28 below illustrates a method for preparing 3-(2-nitrophenyl)-1,2,4-thiadiazoles and 5-chloro-3-(2-nitrophenyl)-1,2,4-thiadiazoles of Formula (VIIp).

Equation 28

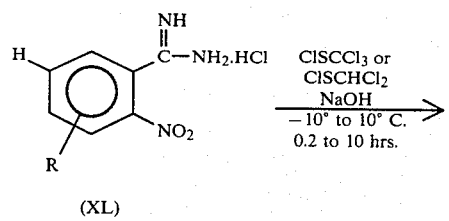

(XL)

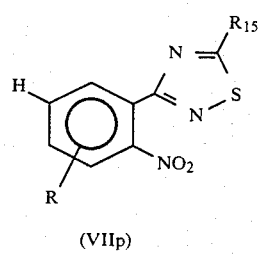

(VIIp)

wherein
R is as defined above; and
$R_{15}$ is H or Cl.

The reactions of Equation 28 can be run according to similar procedures described in J. Goerdeler et al., *Chem. Ber.*, 53, 8166 (1959); and J. Goerdeler and M. Budnowski, *Chem. Ber.*, 94, 1682 (1961). Thus, a 2-nitrobenzamidine HCl of Formula (XL) is reacted with perchloromethylmercaptan or dichloromethanesulfenyl chloride and sodium hydroxide in a solvent such as water-methylene chloride or aqueous dioxane at about −10° to 10° C. for 0.2 to 10 hours to form VIIp.

Equation 29 below illustrates a method for preparing 5-alkyl-3-(2-nitrophenyl)-1,2,4-thiadiazoles of Formula (VIIp').

Equation 29

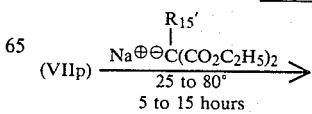 (a)

-continued
Equation 29

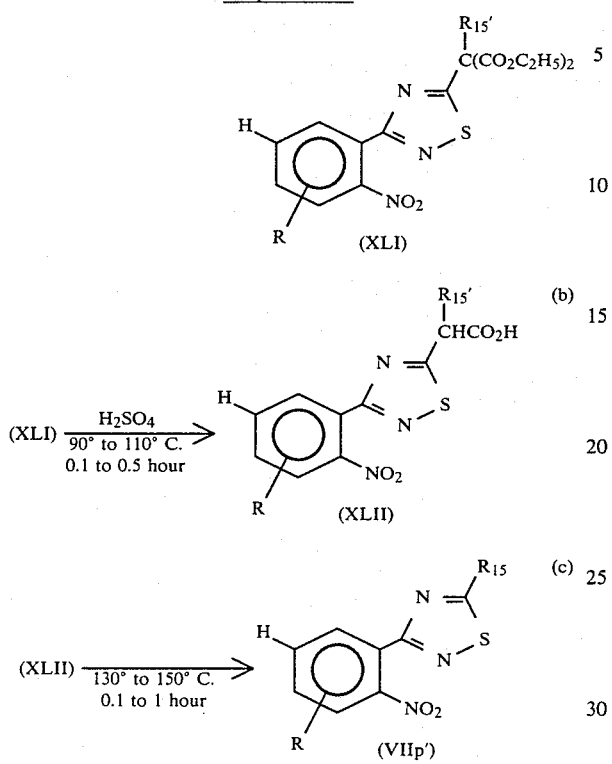

wherein
R is as defined above;
$R_{15}'$ is H or $CH_3$; and
$R_{15}$ is $CH_3$ or $C_2H_5$.

The reactions of Equation 29 above can be run according to similar procedures described in G. Goerdeler and H. Hammer, *Ber.*, 97, 1134 (1964). Thus, in reaction 29a, 5-chloro-3-(2-nitrophenyl)-1,2,4-thiadiazole VIIp is reacted with an appropriate diethyl sodiomalonate in a solvent such as benzene or tetrahydrofuran at reflux for about 5 to 15 hours to form a 5-(substituted)-3-(2-nitrophenyl)-1,2,4-thiadiazole of Formula (XLI). In reaction 29b, XLI is deesterified by heating it in aqueous sulfuric acid at 90° to 110° C. for about 0.1 to 0.5 hour to form a 5-carboxymethylene-3-(2-nitrophenyl)-1,2,4-thiadiazole of Formula (XLII). And in reaction 29c, XLII is decarboxylated by heating under nitrogen at about 130° to 150° C. for 0.1 to 1 hour to form VIIp'.

Equation 30 below illustrates a method for preparing 5-(2-nitrophenyl)-1,2,4-thiadiazoles of Formula (VIIq).

Equation 30

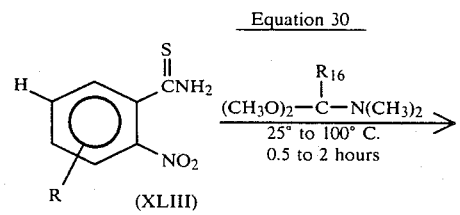

(a)

-continued
Equation 30

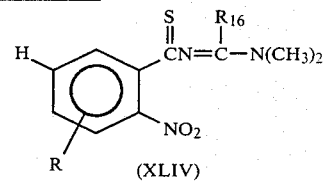

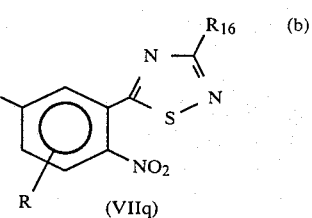

wherein
R and $R_{16}$ are as defined above.

The reactions of Equation 30 above can be run according to similar procedures described in Yang-i Lin et al., *J. Org. Chem.*, 45, 3750 (1980). Thus, in reaction 30a, a 2-nitrobenzthioamide of Formula (XLIII) is reacted with an appropriate N,N-dimethylalkanamide dimethyl acetal at 25° to 100° C. for 0.5 to 2 hours to form N-[(dimethylamino)methylene]-2-nitrobenzthioamide of Formula (XLIV). In the second reaction, XLIV is reacted with O-(mesitylenesulfonyl)hydroxylamine (MSH) in a solvent such as methylene chloride at 0° to 30° C. for 0.5 to 5 hours to form VIIq.

The 3-(2-nitrophenyl)-1,2,5-thiadiazoles of Formula (VIIr) in Equation 31 below can be prepared by nitrating 3-phenyl-1,2,5-thiadiazoles of Formula (XLV) with nitric acid at 0° to 30° C. for 0.2 to 2 hours, according to the teachings of A. de Munno et al., *Int. J. Sulfur Chem.*, Part A, 2, 25 (1972).

Equation 31

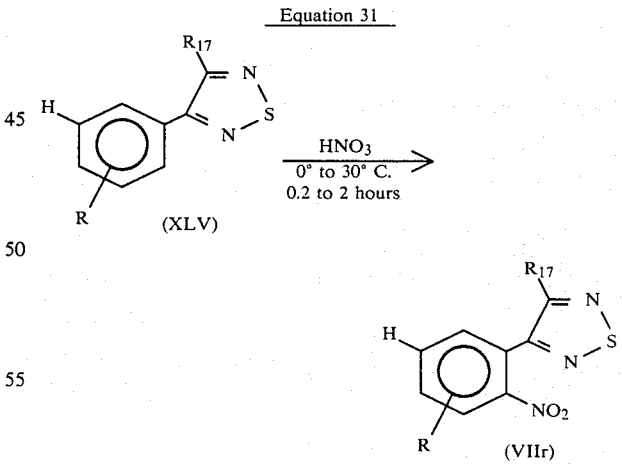

wherein
R and $R_{17}$ are as defined above.

The starting compounds XLV in Equation 31 above can be prepared by known methods. Several such methods are described in L. Weinstock et al., *J. Org. Chem.*, 32, 2823 (1967); S. Mataka et al., *Synthesis*, 7, 524 (1979); V. Bertini and P. Pino, *Angew. Chem. Internat. Edit.*, 5, 514 (1966); and V. Bertini and P. Pino, *Corsi. Semin. Chim.*, 10, 82 (1968).

The 1-alkyl-5-(2-nitrophenyl)-1H-1,2,4-triazoles of Formula (VIIs) in Equation 32 below can be prepared by reacting a N-[(dimethylamino)methylene]-2-nitrobenzamide of Formula (XLVI) with alkylhydrazine in acetic acid at 50° to 90° C. for 0.5 to 2 hours, according to the teachings of Lin et al., *J. Org. Chem.*, 44, 4160 (1979). The starting material XLVI can be prepared by procedures described above in Equation 24a.

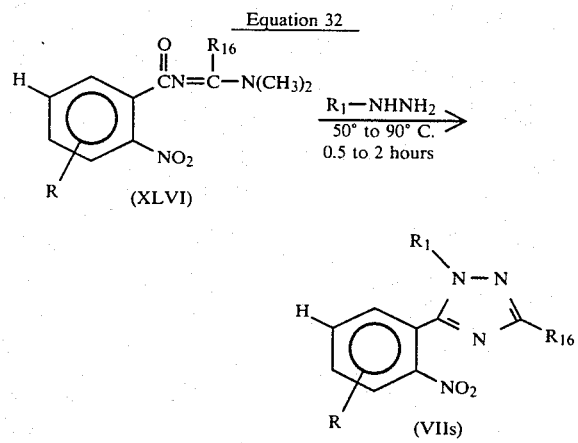

wherein
R, R$_1$ and R$_{16}$ are as defined above.

Equation 33 below illustrates a method for preparing 1-alkyl-3-(2-nitrophenyl)-1H-1,2,4-triazoles of Formula (VIIt).

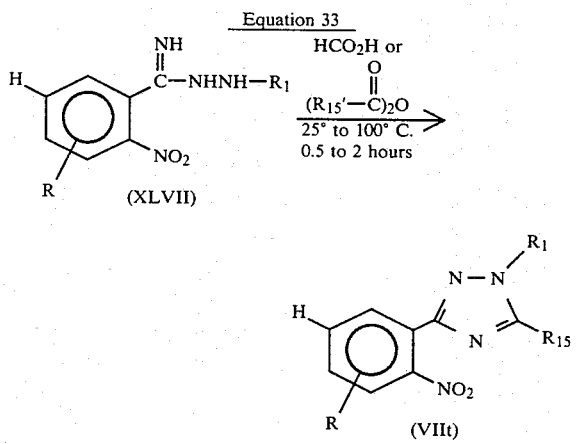

wherein
R, R$_1$ and R$_{15}$ are as defined above; and
R$_{15}'$ is CH$_3$ or C$_2$H$_5$.

The reaction of Equation 33 above can be run according to similar procedures described in M. Atkinson and J. Polya, *J. Chem. Soc.*, 3319 (1954). Thus, VIIt is prepared by reacting a N-2-nitrobenzimidoyl-N'-alkylhydrazine of Formula (XLVII) with formic acid, acetic anhydride or propionic anhydride at about 25° to 100° C. for 0.5 to 1 hour. The starting material XLVII is prepared by reacting an appropriate 2-nitrobenzimidoate HCl with alkylhydrazines in pyridine at ambient temperature according to the teachings of ibid.

The 1-(2-nitrophenyl)-1H-1,2,4-pyrazoles of Formula (VIIu) in Equation 34 below can be prepared by reacting a 1-formyl-2-(2-nitrophenyl)hydrazine of Formula (XLVIII) with excess formamide at reflux for about 1 to 6 hours, according to the procedures described in C. Ainsworth et al., *J. Med. Pharm. Chem.*, 5, 383 (1962).

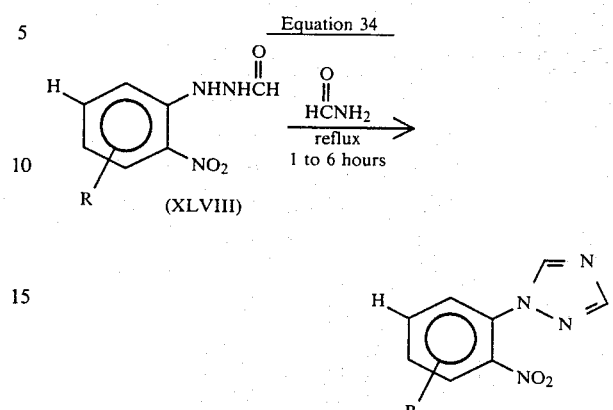

wherein
R is as defined above.

The 1-(2-nitrophenyl)-1H-1,2,4-triazoles of Formula (VIIu') in Equation 35 below can be prepared by reacting a 2-halo-1-nitrobenzene of Formula (XXXI) with a sodium 1,2,4-triazole salt of Formula (XLIX). The reaction can be run by procedures described above in Equation 19 by one skilled in the art.

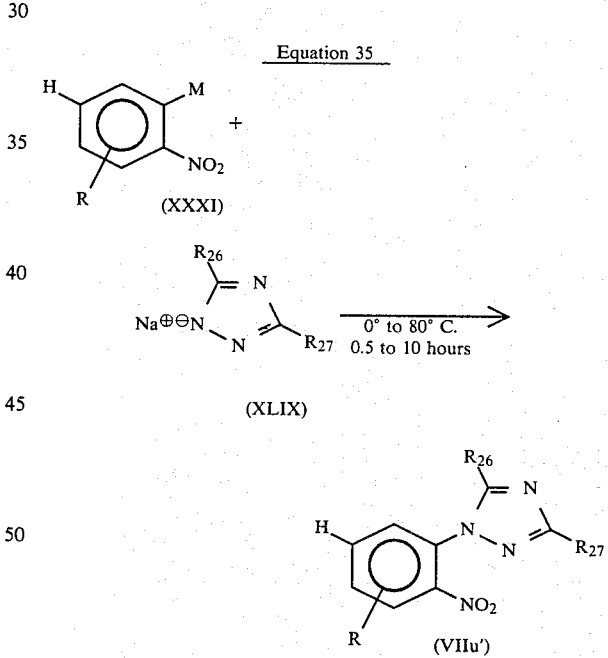

wherein
M is Cl, Br or F; and
R, R$_{26}$ and R$_{27}$ are as defined above.

Many 1-(2-nitrophenyl)-1H-1,2,4-triazoles of Formula (VIIu') above can also be prepared by the Ullman reaction, according to the teachings of M. Khan and J. Polya, *J. Chem. Soc. C.*, 85 (1970). This requires reacting a 2-halonitrobenzene, such as XXXI above, with an appropriately substituted 1,2,4-triazole, copper (II) oxide catalyst and potassium carbonate in pyridine at reflux for 0.5 to several hours. The product is purified by column chromatography.

Equation 36 below illustrates a method for preparing 4-alkyl-3-(2-nitrophenyl)-4H-1,2,4-triazoles of Formula (VIIv).

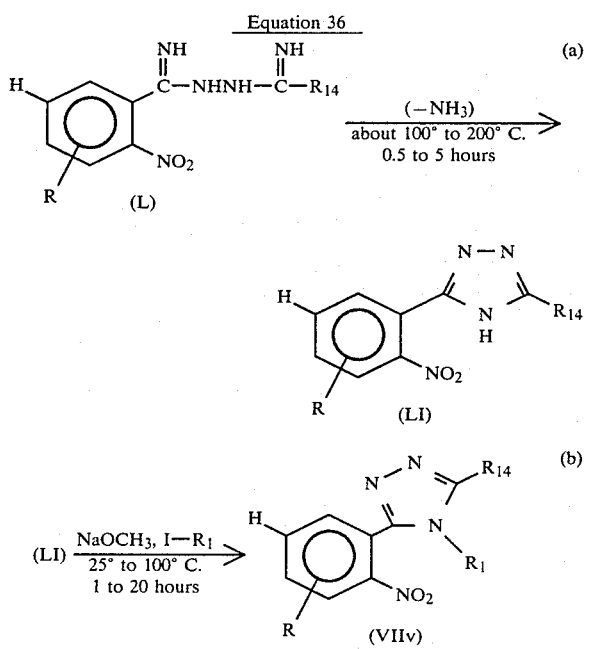

wherein

R, R$_{14}$ and R$_1$ are as defined above.

In the reaction of Equation 36a above, a 2-nitrophenyldihydrazidine of Formula (L) can be heated at elevated temperatures, i.e. 100° to 200° C., in a solvent such as N-methyl-2-pyrrolidinone to cause cyclization to form a 3-(2-nitrophenyl)-4H-1,2,4-triazole of Formula (LI), according to methods known in the art, e.g., A. Rusanov, *Russ. Chem. Rev.*, 43, 795 (1974). In reaction 36b, LI can be alkylated to form VIIv. This requires reacting LI with sodium methoxide followed by an appropriate alkyl iodide in methanol at 25° to 100° C. in a sealed tube for 1 to 20 hours. The product is purified by chromatography procedures.

The 4-(2-nitrophenyl)-4H-1,2,4-triazoles of Formula (VIIw) in Equation 37 below can be prepared by reacting a 2-nitroaniline of Formula (LII) with N,N'-diformylhydrazine at 150° to 200° C. for about 0.5 to 2 hours, according to methods known in the art, e.g., C. Ainsworth et al., *J. Med. Pharm. Chem.*, 5, 383 (1962).

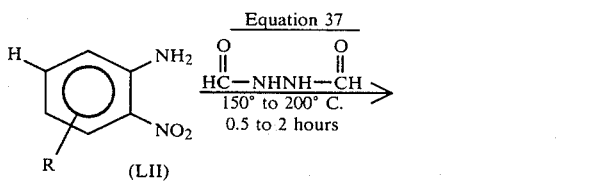

wherein

R is as defined above.

Equation 38 below illustrates a method for preparing 4-(2-aminophenyl)-4H-1,2,4-triazoles of Formula (VIc).

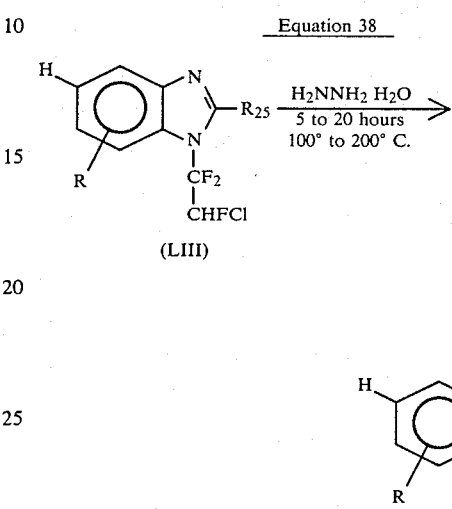

wherein

R and R$_{25}$ are as defined above.

The reaction of Equation 38 above is run according to similar procedures described in W. Ried and H. Lohwasser, *Justus Liebigs Ann. Chem.*, 699, 88 (1966) and *Angew Chem. Int. Ed. Engl.*, 5, 835 (1966). Thus, N-(1,1,2-trifluoro-2-chloroethyl)benzimidazole of Formula (LIII) is reacted with excess hydrazine hydrate in ethylene glycol at reflux for 5 to 20 hours to form VIc.

Equations 39, 40 and 41 below illustrate methods for preparing 2-(2-nitrophenyl)oxazoles of Formulae (VIIy) and (VIIy'). Details of the procedures of Equations 39 and 40 can be found in W. E. Cass, *J. Am. Chem. Soc.*, 64, 785 (1942). Equation 41 illustrates the Robinson-Gabriel synthesis of oxazoles from corresponding acylaminoketones of Formula (LIV). For details see Elderfield, "Heterocyclic Compounds", Vol. 5, Chapter 5, 1957, J. Wiley & Sons, New York and references therein. In all three reactions, R is as defined above.

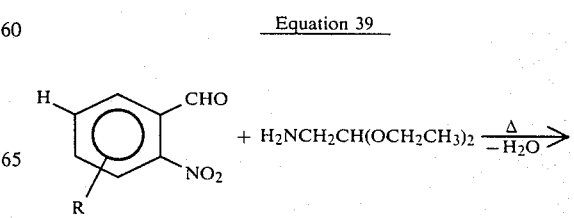

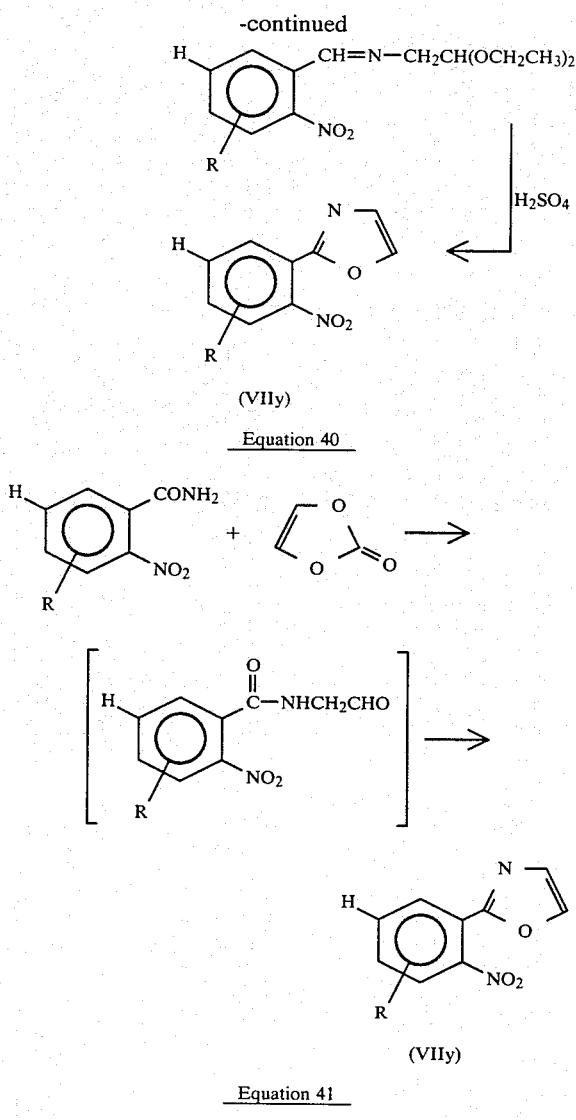

(VIIy)

Equation 40

(VIIy)

Equation 41

(VIIy')

wherein
R$_{12}$ and R$_{13}$ are H, CH$_3$ or CH$_2$CH$_3$; provided that both R$_{12}$ and R$_{13}$ are not simultaneously H.

Equations 42 to 45 below illustrate methods for preparing 5-(2-nitrophenyl)oxazoles of Formula (VIIz) to (VIIz"). For details of the procedures of Equations 42 and 43, see the above cited reference; for Equation 44, see A. M. Van Leusen et al., *Tet. Let.*, 2369 (1972); and for Equation 45, see Y. Koyama et al., *Agric. Biol.* *Chem.*, 45, 1285 (1981). In all four equations, R is as defined above.

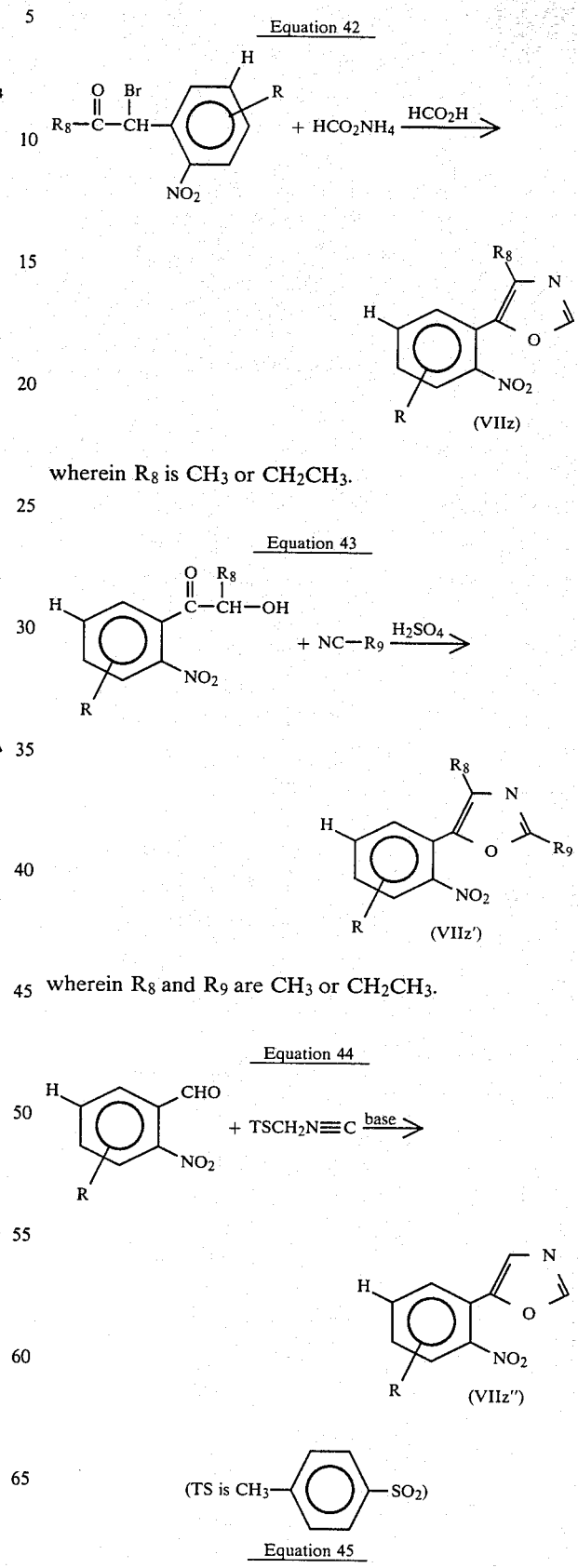

Equation 42

(VIIz)

wherein R$_8$ is CH$_3$ or CH$_2$CH$_3$.

Equation 43

(VIIz')

wherein R$_8$ and R$_9$ are CH$_3$ or CH$_2$CH$_3$.

Equation 44

(VIIz")

(TS is CH$_3$—⌬—SO$_2$)

Equation 45

-continued

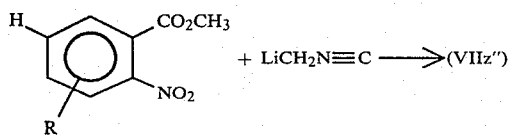

4-(2-Nitrophenyl)oxazoles of Formula (VIIzz) below are prepared by analogous procedures to those described above in Equations 42 and 43. Substituent limitations are the same ($R_8=R_{10}$ and $R_9=R_{11}$).

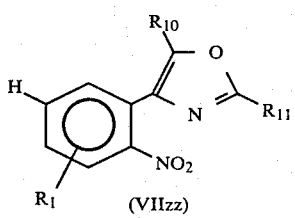

Equations 46 and 47 below illustrate methods for preparing 2-(2-nitrophenyl)thiazoles of Formulae (VIIaa) and (VIIaa'). For additional details on the procedures of Equations 46 and 47, see:
(1) J. V. Metzer (ed.), *Chem. Heterocyclic Compounds*, 34, parts (1–3) (1978–1979).
(2) J. M. Sprague and A. H. Land, "Heterocyclic Compounds", (R. C. Elderfield, ed.) V, 484–722. Wiley, N.Y.

Equation 46

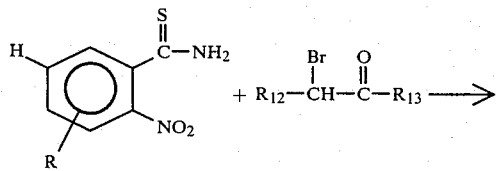

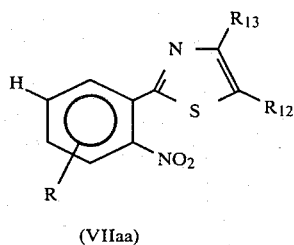

wherein
$R_{12}$ is H, $CH_3$ or $CH_2CH_3$;
$R_{13}$ is $CH_3$ or $CH_2CH_3$; and
R is as defined above.

Equation 47

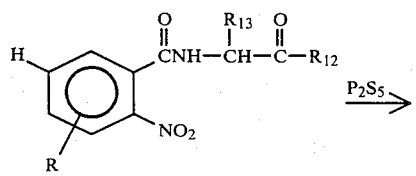

-continued
Equation 47

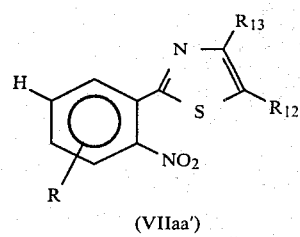

where
$R_{12}$ is H, $CH_3$ or $CH_2CH_3$;
$R_{13}$ is $CH_3$ or $CH_2CH_3$; and
R is as defined above.

Equations 48 and 49 below illustrate methods for preparing 5-(2-nitrophenyl)thiazoles of Formula (VIIbb) and (VIIbb'). For further details on these reactions refer to references cited above for Equations 46 and 47.

Equation 48

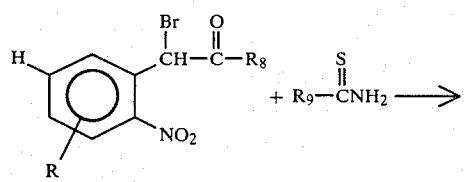

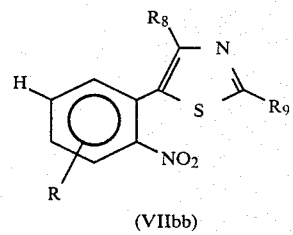

wherein
$R_8$ is H, $CH_3$ or $CH_2CH_3$;
$R_9$ is $CH_3$ or $CH_2CH_3$; and
R is as defined above.

Equation 49

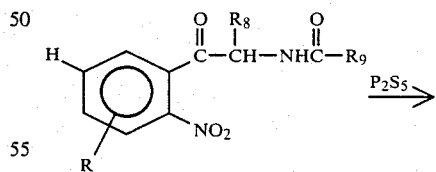

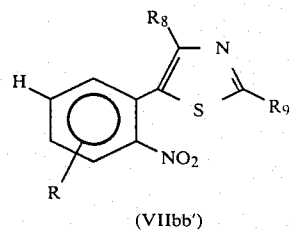

wherein
$R_8$ is $CH_3$ or $CH_2CH_3$;

$R_9$ is H, $CH_3$ or $CH_2CH_3$; and
R is as defined above.

Equations 50 and 51 below illustrate methods for preparing 4-(2-nitrophenyl)thiazoles of Formulae (VIIcc) and (VIIcc'). For further details on these reactions refer to references cited above for Equations 46 and 47.

Equation 50

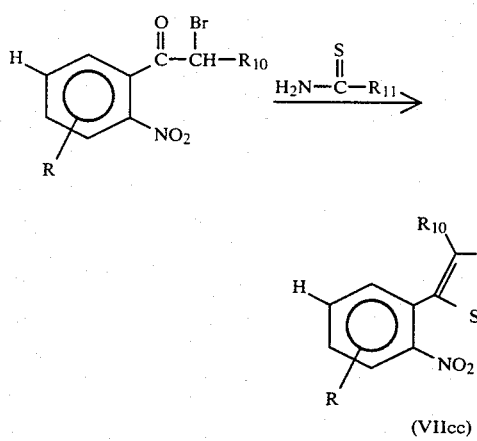

(VIIcc)

wherein
$R_{10}$ is H, $CH_3$ or $CH_2CH_3$;
$R_{11}$ is $CH_3$ or $CH_2CH_3$; and
R is as defined above.

Equation 51

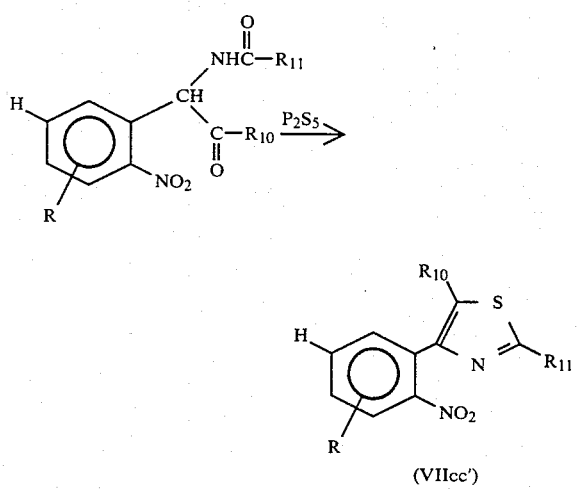

(VIIcc')

wherein
$R_{10}$ is $CH_3$ or $CH_2CH_3$;
$R_{11}$ is H, $CH_3$ or $CH_2CH_3$; and
R is as defined above.

As shown in Equation 52 below, 1-(2-nitrophenyl)-1H-imidazoles of Formula (VIIdd) are prepared by reacting an imidazole sodium salt with 2-halo-1-nitrobenzene. The reaction can be run by procedures described above in Equation 19.

Equation 52

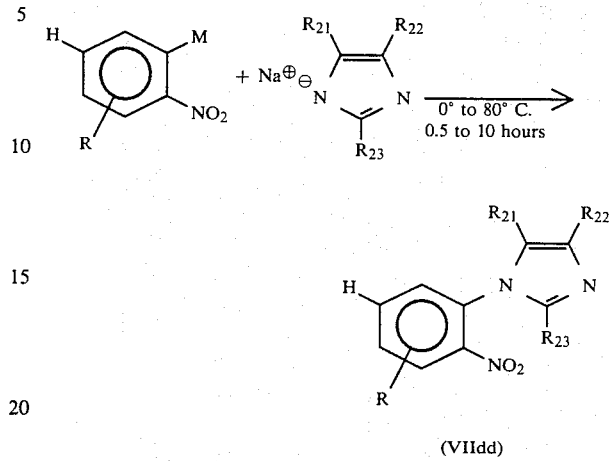

(VIIdd)

wherein
R, $R_{21}$, $R_{22}$ and $R_{23}$ are as defined above; and
M is Cl, Br or F.

As shown in Equation 53 below, 1-alkyl-2-(2-nitrophenyl)-1H-imidazoles of Formula (VIIee) can be prepared by reacting an appropriately substituted 2-nitrobenzaldehyde with a 1,2-diketone in the presence of an alkylamine.

Equation 53

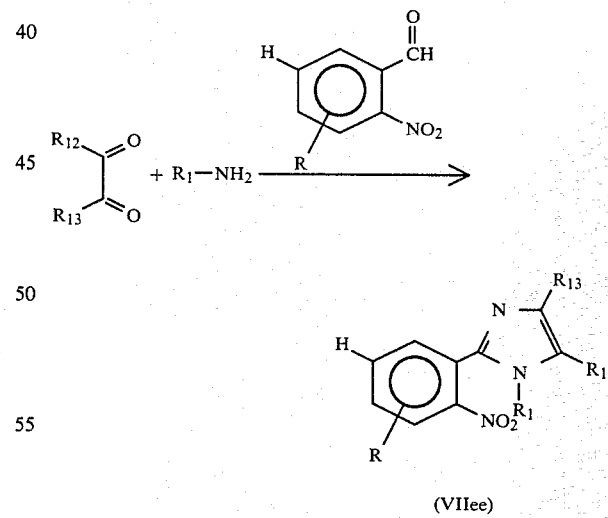

(VIIee)

wherein
R and $R_1$ are as defined above; and
$R_{12}$ and $R_{13}$ are H, $CH_3$ or $CH_2CH_3$.

Equation 54 below illustrates a method for preparing 1-alkyl-5-(2-nitrophenyl)-1H-imidazoles of Formula (VIIff) and 1-alkyl-4-(2-nitrophenyl)-1H-imidazoles of Formula (VIIgg).

Equation 54

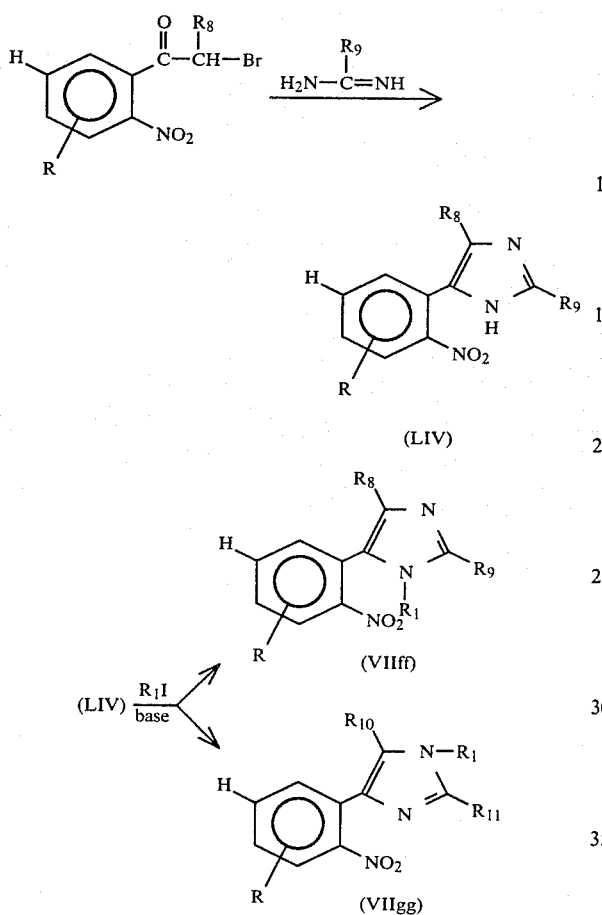

wherein R, R$_1$, R$_8$, R$_9$, R$_{10}$ and R$_{11}$ are as defined above.

According to Equation 54, an appropriate α-haloketone is reacted with an amidine to form 5-(2-nitrophenyl)-1H-imidazole LIV. Subsequent reaction of LIV with an alkyl iodide in the presence of a base yields a product mixture containing VIIff and VIIgg. The product mixture can be transformed to a mixture of corresponding compounds I of the invention by a sequence of reactions described above in Equations 4, 3 and then 2. The reactions of Equation 54 are run by methods obvious to one skilled in the art.

The synthesis of heterocyclic amines such as IV in Equations 1 and 2 above has been reviewed in "The Chemistry of Heterocyclic Compounds", a series published by Interscience Publ., New York and London. 2-Aminopyrimidines are described by D. J. Brown in "The Pyrimidines", Vol. XVI of the above series. The 2-amino-1,3,5-triazines are reviewed by E. M. Smolin and L. Rapaport in "s-Triazines and Derivatives", Vol. XIII of the same series. The synthesis of triazines is also described by F. C. Schaefer, U.S. Pat. No. 3,154,547 and by K. R. Huffman and F. C. Schaefer, *J. Org. Chem.*, 28, 1812–1821 (1963).

The synthesis of heterocyclic amines is also disclosed in S. African Patent Application Nos. 82/5045 and 82/5671.

Also, 2-aminopyrimidines of Formula (IVa) below, where Y is CH(OC$_2$H$_5$)$_2$ are described by W. Baker et al., *J. Am. Chem. Soc.*, 69, 3072 (1947), the disclosures of which are herein incorporated by reference. Using techniques taught by Braker, or suitable modifications that would be obvious to one skilled in the art, the pyrimidines IVa can be prepared.

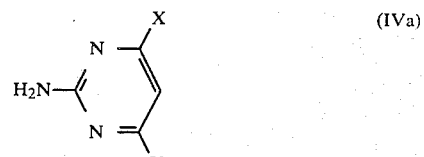

wherein X is CH$_3$ or OCH$_3$; and

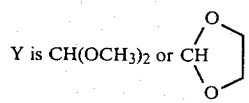

Y is CH(OCH$_3$)$_2$ or

In addition, 2-aminotriazines of Formula (IVb) may be prepared as shown in Equations 55 and 56 below.

Equation 55

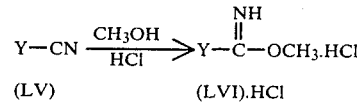

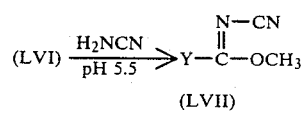

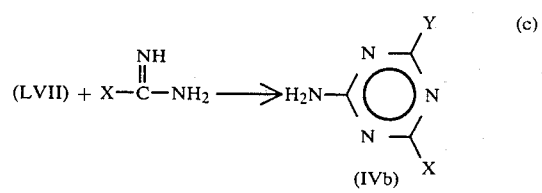

wherein X is CH$_3$ or OCH$_3$; and

Y is CH(OCH$_3$)$_2$ or 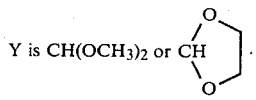

Equation 56

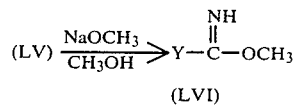

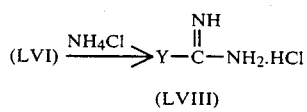

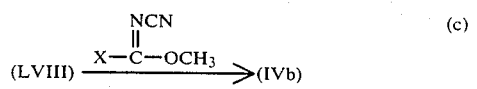

wherein X and Y are as defined in Equation 55.

The reaction of Equation 55a is carried out according to the teachings of J. M. McElvain and R. L. Clarke, *J. Amer. Chem. Soc.*, 69, 2657 (1947), in which the preparation of ethyl diethoxyiminoacetate is described. The intermediate N-cyanoimidate of Formula (LVII) may be prepared according to the teaching of D. Lwowski in *Synthesis*, 1971, 263, by reacting LVI.HCl with cyanamide at pH 5.5, and this may be condensed according to reaction 55c with either acetamide or O-methyl isourea in an alcoholic solvent at 25° to 80° C. to provide the appropriate triazines IVb. Alternatively, the reaction of Equation 56a, described for substituted acetonitriles by F. C. Schaefer and G. A. Peters in *J. Org. Chem.*, 26, 412 (1961), may be used to convert nitrile of Formula (LV) to the corresponding iminoester. The free base may be carried on through reactions 56b and 56c, or, alternatively, converted to the amidinium hydrochloride salt (LVIII) as described in the aforementioned reference, and condensed with either methyl N-cyanoacetimidate or with dimethyl N-cyano imidocarbonate in the presence of one equivalent of sodium methoxide to provide the triazines of Formula (IVb).

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation to another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and all parts are by weight unless otherwise indicated.

EXAMPLE 1

2-(Isoxazol-3-yl)phenyl isocyanatosulfonate

To a solution containing 30 g of 2-(isoxazol-3-yl)phenol [prepared by the procedure of R. Beugelmans and C. Morin, *J. Org. Chem.*, 42, 1356 (1977)] in 200 ml of dry toluene was added slowly 26.3 g of chlorosulfonyl isocyanate while maintaining the temperature at 20° to 30° C. with external cooling. The resulting suspension containing a white solid was stirred at 25° C. for 1 hour, then heated at 100° to 110° C. for 1 hour. The resulting slightly cloudy solution was cooled to 25° C., filtered, and the filtrate was concentrated in vacuo to yield 45 g of the title compound as a crude oil. The IR spectrum showed an isocyanate absorption at 2220 cm$^{-1}$.

EXAMPLE 2

2-(3-Isoxazolyl)phenyl N-[(4,6-dimethoxy-1,3,5-triazin-2-yl)aminocarbonyl]-sulfamate To a suspension of 2 g of 2-amino-4,6-dimethoxy-1,3,5-triazine in 25 ml of tetrahydrofuran was added 4.5 g of the isocyanate prepared above in Example 1. The resulting solution was stirred at 25° C. for 16 hours, then concentrated to dryness in vacuo to yield a viscous oil. The oil was triturated with ethyl acetate to form a solid. The solid was recrystallized from ethyl acetate to yield 2 g of the title compound; m.p. 166°–168° C.

Anal. Calcd. for $C_{15}H_{14}N_6O_7S$: C, 42.7; H, 3.3; N, 19.8. Found: C, 42.8; H, 3.4; N, 20.2.

EXAMPLE 3

2-(1,3,4-Oxadiazol-2-yl)phenyl isocyanatosulfonate

By the procedure of Example 1, 7.1 g of chlorosulfonyl isocyanate was added to a suspension containing 8.1 g of 2-(1,3,4-oxadiazol-2-yl)phenol [prepared by the procedure of J. Maillard et al., *Bull. Soc. Chim. France*, 3, 529 (1961)] in 125 ml of dry toluene. The reaction mixture was stirred at 25° C. for 1 hour, then heated at 100° to 110° C. for about 0.5 hour. The resulting suspension containing a viscous oil was cooled to 25° C., filtered, and the filtrate was concentrated in vacuo to yield 8 g of the title compound as a viscous, crude oil. The IR spectrum showed an isocyanate absorption at 2220 cm$^{-1}$.

EXAMPLE 4

2-(1,3,4-Oxadiazol-2-yl)phenyl N-[(4,6-dimethoxypyrimidin-2-yl)aminocarbonyl]sulfamate To a suspension of 6 g of 2-amino-4,6-dimethoxypyrimidine in 25 ml of tetrahydrofuran was added a solution of 8 g of the isocyanate prepared in Example 3 dissolved in 25 ml of tetrahydrofuran. After an initial exotherm, the solution was stirred at 25° C. for 16 hours, to yield a precipitate. The mixture was filtered, and the solid was recrystallized from acetonitrile to yield 1.5 g of the title compound; m.p. 161°–164° C.

Anal. Calcd. for $C_{15}H_{14}N_6O_7S$: C, 42.7; H, 3.3; N, 19.9. Found: C, 42.7; H, 3.3; N, 20.2.

EXAMPLE 5

2-(1,2,3-Thiadiazol-4-yl)phenyl isocyanatosulfonate

By the procedure of Example 1, 7.9 g of chlorosulfonyl isocyanate was reacted with 10 g of 2-(1,2,3-thiadiazol-4-yl)phenol [prepared by the procedure of U.S. Pat. No. 3,940,407] in 125 ml of dry toluene. The reaction mixture was stirred at 25° C. for 1 hour, then heated at 100° to 110° C. for 1 hour. The resulting solution was cooled to 25° C., filtered, and the filtrate was concentrated in vacuo to yield 14 g of the title compound as a crude oil. The IR showed an isocyanate absorption at 2220 cm$^{-1}$.

EXAMPLE 6

2-(1,2,3-Thiadiazol-4-yl)phenyl N-[(4,6-dimethoxypyrimidin-2-yl)aminocarbonyl]sulfamate By the procedure of Example 4, 5.3 g of 2-amino-4,6-dimethoxypyrimidine in 20 ml of tetrahydrofuran was reacted with 14 g of the isocyanate prepared in Example 5 above in 30 ml of tetrahydrofuran. After stirring the mixture at 25° C. for 3 hours, the mixture was filtered and the solid isolated was recrystallized from acetonitrile to yield 4 g of the title compound; m.p. 173°–175° C.

Anal. Calcd. for $C_{15}H_{14}N_6O_6S_2$: C, 41.1; H, 3.2; N, 19.2 Found: C, 41.4; H, 3.3; N, 19.6

EXAMPLE 7

A. [(4,6-Dimethylpyrimidin-2-yl)aminocarbonyl]sulfamoyl chloride; and

B. 2-(3,5-Dimethyl-1H-pyrazol-1-yl)phenyl N-[(4,6-dimethylpyrimidin-2-yl)aminocarbonyl]sulfamate To 7 g of 2-amino-4,6-dimethylpyrimidine in 100 ml of methylene chloride at 0° C. is added 8.1 g of chlorosulfonyl isocyanate dropwise with stirring. The resultant mixture containing compound A is stirred and allowed to come to room temperature during 1 hour and then 10.7 g of 2-(3,5-dimethyl-1H-pyrazol-1-yl)phenol is added followed by 9 g of pyridine. The mixture is stirred 16 hours at ambient temperature, then poured into 100 ml of ice-water and 10% hydrochloric acid is added to attain a pH of about 6. The methylene chloride layer is separated, extracted with an equal volume of water, dried over sodium sulfate, filtered and concentrated in vacuo. The residue is purified by chromatography procedures to yield title compound B.

Using analogous procedures to those described in Examples 2, 4, 6 and 7 above and methods described in Equations 1–56, the following compounds in Tables I–IIIi can be prepared.

TABLE I

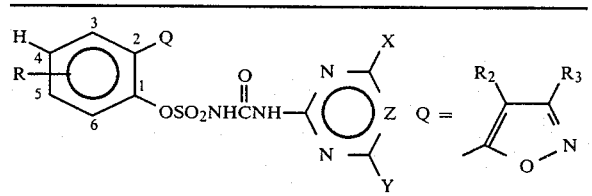

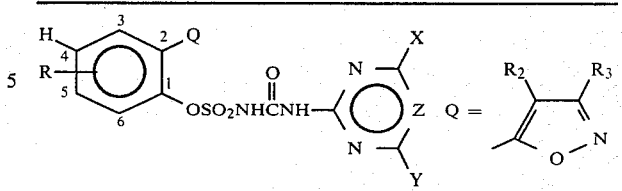

| R | R2 | R3 | X | Y | Z | m.p. (°C.) |
|---|----|----|---|---|---|------------|
| H | H | H | CH3 | CH3 | CH | 68–69° |
| H | H | H | OCH3 | OCH3 | CH | 179–182° |
| H | H | H | CH3 | OCH3 | CH | 115–118° |
| H | H | H | CH3 | CH3 | N | 160–163° |
| H | H | H | OCH3 | OCH3 | N | 137–143° |
| H | H | H | CH3 | OCH3 | N | 143–146° |
| H | H | H | Cl | OCH3 | CH | 164–165° |
| H | H | H | CH3 | C2H5 | CH | |
| H | H | H | OCH3 | CH2OCH3 | N | |
| H | H | H | CH3 | OC2H5 | N | |

TABLE I-continued

| R | R2 | R3 | X | Y | Z | m.p. (°C.) |
|---|----|----|---|---|---|------------|
| H | H | H | OCH3 | OC2H5 | CH | |
| H | H | H | CH3 | CH(OCH3)2 | CH | |
| H | CH3 | H | CH3 | CH3 | CH | |
| H | CH3 | H | OCH3 | OCH3 | CH | |
| H | CH3 | H | CH3 | OCH3 | CH | |
| H | CH3 | H | CH3 | CH3 | N | |
| H | CH3 | H | OCH3 | OCH3 | N | |
| H | CH3 | H | CH3 | OCH3 | N | |
| H | CH3 | H | Cl | OCH3 | CH | |
| H | C2H5 | H | OCH3 | OCH3 | CH | |
| H | H | CH3 | CH3 | CH3 | CH | |
| H | H | CH3 | CH3 | OCH3 | CH | |
| H | H | CH3 | OCH3 | OCH3 | CH | |
| H | H | CH3 | CH3 | CH3 | N | |
| H | H | CH3 | CH3 | OCH3 | N | |
| H | H | CH3 | OCH3 | OCH3 | N | |
| H | H | CH3 | Cl | OCH3 | CH | |
| H | H | C2H5 | OCH3 | OCH3 | CH | |
| 6-F | H | H | OCH3 | OCH3 | CH | |
| 3-Cl | H | H | OCH3 | OCH3 | CH | |
| 6-Br | H | H | OCH3 | OCH3 | CH | |
| 6-CF3 | H | H | OCH3 | OCH3 | CH | |
| 5-OCH3 | H | H | OCH3 | OCH3 | CH | |
| 3-CH3 | H | H | OCH3 | OCH3 | CH | |
| H | H | H | Cl | OC2H5 | CH | |
| H | H | H | OCH3 | CH(OCH3)2 | CH | |
| H | H | H | OCH3 | OCH2CF3 | CH | |
| H | H | H | CH3 | OCH2CF3 | CH | |
| H | H | H | CH3 | OCF2CF3 | N | |
| H | H | H | OCH3 | OCH2CF3 | N | |
| H | H | H | OCH3 | 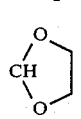 | CH |  |
| H | H | H | CH3 | 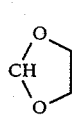 | CH |  |
| H | H | H | OCH3 | 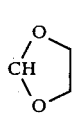 | N |  |
| H | H | H | OCH3 | CH2OCH3 | CH | |
| H | H | H | CH3 | CH2OCH3 | CH | |
| H | H | H | CH3 | OCF2H | CH | |
| H | H | H | OCH3 | OCF2H | CH | |
| H | H | H | CH3 | SCF2H | CH | |
| H | H | H | OCH3 | SCF2H | CH | |
| H | H | H | CH3 | OCF2CHFCl | CH | |
| H | H | H | OCH3 | OCF2CHFCl | CH | |
| H | H | H | CH3 | OCF2CHFBr | CH | |
| H | H | H | OCH3 | OCF2CHFBr | CH | |
| H | H | H | CH3 | OCF2CF2H | CH | |
| H | H | H | OCH3 | OCF2CF2H | CH | |
| H | H | H | CH3 | OCF2CHFCF3 | CH | |
| H | H | H | OCH3 | OCF2CHFCF3 | CH | |
| H | H | H | OCF2H | OCF2H | CH | |
| H | H | H | OCF2H | SCF2H | CH | |
| H | H | H | SCF2H | SCF2H | CH | |
| H | H | H | CH3 | OCF2H | N | |
| H | H | H | OCH3 | OCF2H | N | |
| H | H | H | CH3 | SCF2H | N | |
| H | H | H | OCH3 | SCF2H | N | |

TABLE I-continued

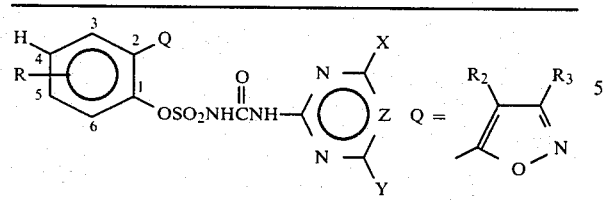

Q = 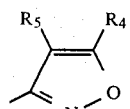

| R | R2 | R3 | X | Y | Z | m.p. (°C.) |
|---|----|----|---|---|---|-----------|
| H | H | H | CH3 | OCF2CHFCl | N | |
| H | H | H | OCH3 | OCF2CHFCl | N | |
| H | H | H | CH3 | OCF2CHFBr | N | |
| H | H | H | OCH3 | OCF2CHFBr | N | |
| H | H | H | CH3 | OCF2CF2H | N | |
| H | H | H | OCH3 | OCF2CF2H | N | |
| H | H | H | CH3 | OCF2CHFCF3 | N | |
| H | H | H | OCH3 | OCF2CHFCF3 | N | |
| H | H | H | OCF2H | OCF2H | N | |

TABLE Ia

[In Formula I] Q is

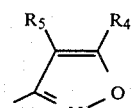

| R | R4 | R5 | X | Y | Z | m.p. (°C.) |
|---|----|----|---|---|---|-----------|
| H | H | H | CH3 | CH3 | CH | 134–136° |
| H | H | H | OCH3 | OCH3 | CH | 181–183° |
| H | H | H | CH3 | OCH3 | CH | 163–165° |
| H | H | H | CH3 | CH3 | N | 168–170° |
| H | H | H | OCH3 | OCH3 | N | 166–168° |
| H | H | H | CH3 | OCH3 | N | 88–92° |
| H | H | H | Cl | OCH3 | CH | 155–157° |
| H | H | H | OCH3 | C2H5 | CH | |
| H | H | H | OCH3 | CH2OCH3 | N | |
| H | H | H | CH3 | OC2H5 | N | |
| H | H | H | OCH3 | OC2H5 | CH | |
| H | H | H | OCH3 | CH(OCH3)2 | CH | |
| H | CH3 | H | CH3 | CH3 | CH | |
| H | CH3 | H | OCH3 | OCH3 | CH | |
| H | CH3 | H | CH3 | OCH3 | CH | |
| H | CH3 | H | CH3 | CH3 | N | |
| H | CH3 | H | OCH3 | OCH3 | N | |
| H | CH3 | H | CH3 | OCH3 | N | |
| H | CH3 | H | Cl | OCH3 | CH | |
| H | C2H5 | H | OCH3 | OCH3 | CH | |
| H | H | CH3 | CH3 | CH3 | CH | |
| H | H | CH3 | OCH3 | OCH3 | CH | |
| H | H | CH3 | OCH3 | OCH3 | CH | |
| H | H | CH3 | CH3 | CH3 | N | |
| H | H | CH3 | OCH3 | OCH3 | N | |
| H | H | CH3 | OCH3 | OCH3 | N | |
| H | H | CH3 | Cl | OCH3 | CH | |
| H | H | C2H5 | OCH3 | OCH3 | CH | |
| 6-F | H | H | OCH3 | OCH3 | CH | |
| 3-Cl | H | H | OCH3 | OCH3 | CH | |
| 6-Br | H | H | OCH3 | OCH3 | CH | |
| 6-CF3 | H | H | OCH3 | OCH3 | CH | |
| 5-OCH3 | H | H | OCH3 | OCH3 | CH | |
| 3-CH3 | H | H | OCH3 | OCH3 | CH | |
| H | H | H | OCH3 | OCH2CF3 | CH | |
| H | H | H | CH3 | OCH2CF3 | N | |
| H | H | H | OCH3 | OCH2CF3 | N | |
| H | H | H | OCH3 | CH2OCH3 | CH | |

TABLE Ia-continued

[In Formula I] Q is

| R | R4 | R5 | X | Y | Z | m.p. (°C.) |
|---|----|----|---|---|---|-----------|
| H | H | H | OCH3 | O-CH-O-CH2-CH2 (1,3-dioxolane) | CH | |
| H | H | H | CH3 | O-CH-O-CH2-CH2 (1,3-dioxolane) | CH | |
| H | H | H | CH3 | C2H5 | CH | |
| H | H | H | CH3 | CH(OCH3)2 | CH | |
| H | H | H | Cl | OC2H5 | CH | |
| H | H | H | CH3 | OCF2H | CH | |
| H | H | H | OCH3 | OCF2H | CH | |
| H | H | H | CH3 | SCF2H | CH | |
| H | H | H | OCH3 | SCF2H | CH | |
| H | H | H | CH3 | OCF2CHFCl | CH | |
| H | H | H | OCH3 | OCF2CHFCl | CH | |
| H | H | H | CH3 | OCF2CHFBr | CH | |
| H | H | H | OCH3 | OCF2CHFBr | CH | |
| H | H | H | CH3 | OCF2CF2H | CH | |
| H | H | H | OCH3 | OCF2CF2H | CH | |
| H | H | H | CH3 | OCF2CHFCF3 | CH | |
| H | H | H | OCH3 | OCF2CHFCF3 | CH | |
| H | H | H | OCF2H | OCF2H | CH | |
| H | H | H | OCF2H | SCF2H | CH | |
| H | H | H | SCF2H | SCF2H | CH | |
| H | H | H | CH3 | OCF2H | N | |
| H | H | H | OCH3 | OCF2H | N | |
| H | H | H | CH3 | SCF2H | N | |
| H | H | H | OCH3 | SCF2H | N | |
| H | H | H | CH3 | OCF2CHFCl | N | |
| H | H | H | OCH3 | OCF2CHFCl | N | |
| H | H | H | CH3 | OCF2CHFBr | N | |
| H | H | H | OCH3 | OCF2CHFBr | N | |
| H | H | H | CH3 | OCF2CF2H | N | |
| H | H | H | OCH3 | OCF2CF2H | N | |
| H | H | H | CH3 | OCF2CHFCF3 | N | |
| H | H | H | OCH3 | OCF2CHFCF3 | N | |
| H | H | H | OCF2H | OCF2H | N | |

TABLE Ib

[In Formula I] Q is

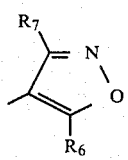

| R | R6 | R7 | X | Y | Z | m.p. (°C.) |
|---|----|----|---|---|---|-----------|
| H | H | H | CH3 | CH3 | CH | |
| H | H | H | OCH3 | OCH3 | CH | |
| H | H | H | CH3 | OCH3 | CH | |
| H | H | H | CH3 | CH3 | N | |
| H | H | H | OCH3 | OCH3 | N | |
| H | H | H | CH3 | OCH3 | N | |
| H | H | H | Cl | OCH3 | CH | |
| H | H | H | CH3 | C2H5 | CH | |
| H | H | H | OCH3 | CH2OCH3 | N | |
| H | H | H | CH3 | OC2H5 | N | |
| H | H | H | OCH3 | OC2H5 | CH | |
| H | H | H | CH3 | CH(OCH3)2 | CH | |

TABLE Ib-continued

[In Formula I] Q is

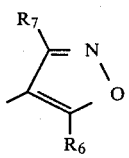

| R | R6 | R7 | X | Y | Z | m.p. (°C.) |
|---|---|---|---|---|---|---|
| H | CH3 | H | CH3 | CH3 | CH | |
| H | CH3 | H | OCH3 | OCH3 | CH | |
| H | CH3 | H | CH3 | OCH3 | CH | |
| H | CH3 | H | CH3 | CH3 | N | |
| H | CH3 | H | CH3 | OCH3 | N | |
| H | CH3 | H | Cl | OCH3 | CH | |
| H | H | CH3 | CH3 | CH3 | CH | |
| H | H | CH3 | CH3 | OCH3 | CH | |
| H | H | CH3 | OCH3 | OCH3 | CH | |
| H | H | CH3 | CH3 | CH3 | N | |
| H | H | CH3 | CH3 | OCH3 | N | |
| H | H | CH3 | OCH3 | OCH3 | N | |
| H | H | CH3 | Cl | OCH3 | CH | |
| 6-F | H | H | OCH3 | OCH3 | CH | |
| 3-Cl | H | H | OCH3 | OCH3 | CH | |
| 6-Br | H | H | OCH3 | OCH3 | CH | |
| 6-CF3 | H | H | OCH3 | OCH3 | CH | |
| 5-OCH3 | H | H | OCH3 | OCH3 | CH | |
| 3-CH3 | H | H | OCH3 | OCH3 | CH | |
| H | H | H | CH3 | OC2H5 | CH | |
| H | H | H | OCH3 | OCH2CF3 | CH | |
| H | H | H | CH3 | OCH2CF3 | CH | |
| H | H | H | OCH3 | OCH2CF3 | N | |
| H | H | H | CH3 | OCH2CF3 | N | |
| H | H | H | OCH3 | CH2OCH3 | CH | |
| H | H | H | OCH3 | CH(OCH3)2 | CH | |
| H | H | H | OCH3 |  | CH | |
| H | H | H | CH3 | OCF2H | CH | |
| H | H | H | OCH3 | OCF2H | CH | |
| H | H | H | CH3 | SCF2H | CH | |
| H | H | H | OCH3 | SCF2H | CH | |
| H | H | H | CH3 | OCF2CHFCl | CH | |
| H | H | H | OCH3 | OCF2CHFCl | CH | |
| H | H | H | CH3 | OCF2CHFBr | CH | |
| H | H | H | OCH3 | OCF2CHFBr | CH | |
| H | H | H | CH3 | OCF2CF2H | CH | |
| H | H | H | OCH3 | OCF2CF2H | CH | |
| H | H | H | CH3 | OCF2CHFCF3 | CH | |
| H | H | H | OCH3 | OCF2CHFCF3 | CH | |
| H | H | H | OCF2H | OCF2H | CH | |
| H | H | H | OCF2H | SCF2H | CH | |
| H | H | H | SCF2H | SCF2H | CH | |
| H | H | H | CH3 | OCF2H | N | |
| H | H | H | OCH3 | OCF2H | N | |
| H | H | H | CH3 | SCF2H | N | |
| H | H | H | OCH3 | SCF2H | N | |
| H | H | H | CH3 | OCF2CHFCl | N | |
| H | H | H | OCH3 | OCF2CHFCl | N | |
| H | H | H | CH3 | OCF2CHFBr | N | |
| H | H | H | OCH3 | OCF2CHFBr | N | |
| H | H | H | CH3 | OCF2CF2H | N | |
| H | H | H | OCH3 | OCF2CF2H | N | |
| H | H | H | CH3 | OCF2CHFCF3 | N | |
| H | H | H | OCH3 | OCF2CHFCF3 | N | |
| H | H | H | OCF2H | OCF2H | N | |

TABLE Ic

[In Formula I] Q is

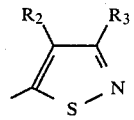

| R | R2 | R3 | X | Y | Z | m.p.(°C.) |
|---|---|---|---|---|---|---|
| H | H | H | CH3 | CH3 | CH | |
| H | H | H | OCH3 | OCH3 | CH | |
| H | H | H | CH3 | OCH3 | CH | |
| H | H | H | CH3 | CH3 | N | |
| H | H | H | OCH3 | OCH3 | N | |
| H | H | H | CH3 | OCH3 | N | |
| H | H | H | Cl | OCH3 | CH | |
| H | H | H | CH3 | C2H5 | CH | |
| H | H | H | OCH3 | CH2OCH3 | N | |
| H | H | H | CH3 | OC2H5 | N | |
| H | H | H | OCH3 | OC2H5 | CH | |
| H | H | H | CH3 | CH(OCH3)2 | CH | |
| H | CH3 | H | OCH3 | OCH3 | CH | |
| H | C2H5 | H | OCH3 | OCH3 | CH | |
| H | H | CH3 | OCH3 | OCH3 | CH | |
| H | H | C2H5 | OCH3 | OCH3 | CH | |
| H | H | H | OCH3 | OCH2CF3 | CH | |
| H | H | H | CH3 |  | CH | |
| H | H | H | CH3 | OCF2H | CH | |
| H | H | H | OCH3 | OCF2H | CH | |
| H | H | H | CH3 | SCF2H | CH | |
| H | H | H | OCH3 | SCF2H | CH | |
| H | H | H | CH3 | OCF2CHFCl | CH | |
| H | H | H | OCH3 | OCF2CHFCl | CH | |
| H | H | H | CH3 | OCF2CHFBr | CH | |
| H | H | H | OCH3 | OCF2CHFBr | CH | |
| H | H | H | CH3 | OCF2CF2H | CH | |
| H | H | H | OCH3 | OCF2CF2H | CH | |
| H | H | H | CH3 | OCF2CHFCF3 | CH | |
| H | H | H | OCH3 | OCF2CHFCF3 | CH | |
| H | H | H | OCF2H | OCF2H | CH | |
| H | H | H | OCF2H | SCF2H | CH | |
| H | H | H | SCF2H | SCF2H | CH | |
| H | H | H | CH3 | OCF2H | N | |
| H | H | H | OCH3 | OCF2H | N | |
| H | H | H | CH3 | SCF2H | N | |
| H | H | H | OCH3 | SCF2H | N | |
| H | H | H | CH3 | OCF2CHFCl | N | |
| H | H | H | OCH3 | OCF2CHFCl | N | |
| H | H | H | CH3 | OCF2CHFBr | N | |
| H | H | H | OCH3 | OCF2CHFBr | N | |
| H | H | H | CH3 | OCF2CF2H | N | |
| H | H | H | OCH3 | OCF2CF2H | N | |
| H | H | H | CH3 | OCF2CHFCF3 | N | |
| H | H | H | OCH3 | OCF2CHFCF3 | N | |
| H | H | H | OCF2H | OCF2H | N | |

TABLE Id

[In Formula I] Q is

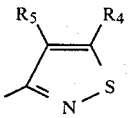

| R | R4 | R5 | X | Y | Z | m.p. (°C.) |
|---|---|---|---|---|---|---|
| H | H | H | CH3 | CH3 | CH | |
| H | H | H | OCH3 | OCH3 | CH | |
| H | H | H | CH3 | OCH3 | CH | |
| H | H | H | CH3 | CH3 | N | |
| H | H | H | OCH3 | OCH3 | N | |
| H | H | H | CH3 | OCH3 | N | |
| H | H | H | Cl | OCH3 | CH | |

TABLE Id-continued

[In Formula I] Q is

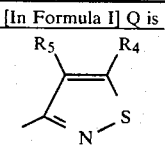

| R | R4 | R5 | X | Y | Z | m.p. (°C.) |
|---|---|---|---|---|---|---|
| H | H | H | CH3 | C2H5 | CH | |
| H | H | H | OCH3 | CH2OCH3 | N | |
| H | H | H | CH3 | OC2H5 | N | |
| H | H | H | OCH3 | OC2H5 | CH | |
| H | H | H | CH3 | CH(OCH3)2 | CH | |
| H | CH3 | H | OCH3 | OCH3 | CH | |
| H | C2H5 | H | OCH3 | OCH3 | CH | |
| H | H | CH3 | OCH3 | OCH3 | CH | |
| H | H | C2H5 | OCH3 | OCH3 | CH | |
| H | H | H | CH3 | OCF2H | CH | |
| H | H | H | OCH3 | OCF2H | CH | |
| H | H | H | CH3 | SCF2H | CH | |
| H | H | H | OCH3 | SCF2H | CH | |
| H | H | H | CH3 | OCF2CHFCl | CH | |
| H | H | H | OCH3 | OCF2CHFCl | CH | |
| H | H | H | CH3 | OCF2CHFBr | CH | |
| H | H | H | OCH3 | OCF2CHFBr | CH | |
| H | H | H | CH3 | OCF2CF2H | CH | |
| H | H | H | OCH3 | OCF2CF2H | CH | |
| H | H | H | CH3 | OCF2CHFCF3 | CH | |
| H | H | H | OCH3 | OCF2CHFCF3 | CH | |
| H | H | H | OCF2H | OCF2H | CH | |
| H | H | H | OCF2H | SCF2H | CH | |
| H | H | H | SCF2H | SCF2H | CH | |
| H | H | H | CH3 | OCF2H | N | |
| H | H | H | OCH3 | OCF2H | N | |
| H | H | H | CH3 | SCF2H | N | |
| H | H | H | OCH3 | SCF2H | N | |
| H | H | H | CH3 | OCF2CHFCl | N | |
| H | H | H | OCH3 | OCF2CHFCl | N | |
| H | H | H | CH3 | OCF2CHFBr | N | |
| H | H | H | OCH3 | OCF2CHFBr | N | |
| H | H | H | CH3 | OCF2CF2H | N | |
| H | H | H | OCH3 | OCF2CF2H | N | |
| H | H | H | CH3 | OCF2CHFCF3 | N | |
| H | H | H | OCH3 | OCF2CHFCF3 | N | |
| H | H | H | OCF2H | OCF2H | N | |

TABLE Ie

[In Formula I] Q is

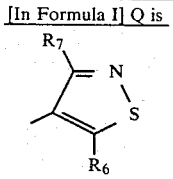

| R | R6 | R7 | X | Y | Z | m.p. (°C.) |
|---|---|---|---|---|---|---|
| H | H | H | CH3 | CH3 | CH | |
| H | H | H | OCH3 | OCH3 | CH | |
| H | H | H | CH3 | OCH3 | CH | |
| H | H | H | CH3 | CH3 | N | |
| H | H | H | OCH3 | OCH3 | N | |
| H | H | H | CH3 | OCH3 | N | |
| H | H | H | Cl | OCH3 | CH | |
| H | H | H | CH3 | C2H5 | CH | |
| H | H | H | OCH3 | CH2OCH3 | N | |
| H | H | H | CH3 | OC2H5 | N | |
| H | H | H | OCH3 | OC2H5 | CH | |
| H | H | H | CH3 | CH(OCH3)2 | CH | |
| H | CH3 | H | OCH3 | OCH3 | CH | |
| H | H | CH3 | OCH3 | OCH3 | CH | |
| H | H | H | OCH3 | OCH2CF3 | CH | |
| H | H | H | CH3 |  | CH | |

TABLE Ie-continued

[In Formula I] Q is

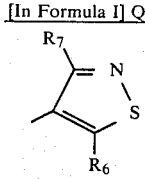

| R | R6 | R7 | X | Y | Z | m.p. (°C.) |
|---|---|---|---|---|---|---|
| H | H | H | CH3 | OCF2H | CH | |
| H | H | H | OCH3 | OCF2H | CH | |
| H | H | H | CH3 | SCF2H | CH | |
| H | H | H | OCH3 | SCF2H | CH | |
| H | H | H | CH3 | OCF2CHFCl | CH | |
| H | H | H | OCH3 | OCF2CHFCl | CH | |
| H | H | H | CH3 | OCF2CHFBr | CH | |
| H | H | H | OCH3 | OCF2CHFBr | CH | |
| H | H | H | CH3 | OCF2CF2H | CH | |
| H | H | H | OCH3 | OCF2CF2H | CH | |
| H | H | H | CH3 | OCF2CHFCF3 | CH | |
| H | H | H | OCH3 | OCF2CHFCF3 | CH | |
| H | H | H | OCF2H | OCF2H | CH | |
| H | H | H | OCF2H | SCF2H | CH | |
| H | H | H | SCF2H | SCF2H | CH | |
| H | H | H | CH3 | OCF2H | N | |
| H | H | H | OCH3 | OCF2H | N | |
| H | H | H | CH3 | SCF2H | N | |
| H | H | H | OCH3 | SCF2H | N | |
| H | H | H | CH3 | OCF2CHFCl | N | |
| H | H | H | OCH3 | OCF2CHFCl | N | |
| H | H | H | CH3 | OCF2CHFBr | N | |
| H | H | H | OCH3 | OCF2CHFBr | N | |
| H | H | H | CH3 | OCF2CF2H | N | |
| H | H | H | OCH3 | OCF2CF2H | N | |
| H | H | H | CH3 | OCF2CHFCF3 | N | |
| H | H | H | OCH3 | OCF2CHFCF3 | N | |
| H | H | H | OCF2H | OCF2H | N | |

TABLE II

[In Formula I] Q is

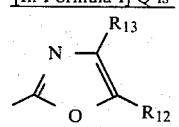

| R | R12 | R13 | X | Y | Z | m.p. (°C.) |
|---|---|---|---|---|---|---|
| H | H | H | CH3 | CH3 | CH | |
| H | H | H | OCH3 | OCH3 | CH | |
| H | H | H | CH3 | OCH3 | CH | |
| H | H | H | CH3 | CH3 | N | |
| H | H | H | OCH3 | OCH3 | N | |
| H | H | H | CH3 | OCH3 | N | |
| H | H | H | Cl | OCH3 | CH | |
| H | H | H | CH3 | C2H5 | CH | |
| H | H | H | OCH3 | CH2OCH3 | N | |
| H | H | H | CH3 | OC2H5 | N | |
| H | H | H | OCH3 | OC2H5 | CH | |
| H | H | H | OCH3 | CH(OCH3)2 | CH | |
| H | CH3 | H | OCH3 | OCH3 | CH | |
| H | C2H5 | H | OCH3 | OCH3 | CH | |
| H | H | CH3 | OCH3 | OCH3 | CH | |
| H | H | C2H5 | OCH3 | OCH3 | CH | |
| 5-F | H | H | OCH3 | OCH3 | CH | |
| 6-Cl | H | H | OCH3 | OCH3 | CH | |
| 6-Br | H | H | OCH3 | OCH3 | CH | |
| 5-CF3 | H | H | OCH3 | OCH3 | CH | |
| 5-OCH3 | H | H | OCH3 | OCH3 | CH | |
| 3-CH3 | H | H | OCH3 | OCH3 | CH | |
| H | H | H | OCH3 | OCH3 | CH | |
| H | H | H | CH3 | OCH2CF3 | CH | |
| H | H | H | OCH3 | OCH2CF3 | N | |

TABLE II-continued

[In Formula I] Q is

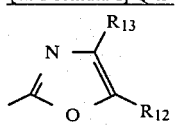

| R | R12 | R13 | X | Y | Z | m.p. (°C.) |
|---|---|---|---|---|---|---|
| H | H | H | OCH3 |  | CH | |
| H | H | H | Cl | OC2H5 | CH | |
| H | H | H | CH3 | OCF2H | CH | |
| H | H | H | OCH3 | OCF2H | CH | |
| H | H | H | CH3 | SCF2H | CH | |
| H | H | H | OCH3 | SCF2H | CH | |
| H | H | H | CH3 | OCF2CHFCl | CH | |
| H | H | H | OCH3 | OCF2CHFCl | CH | |
| H | H | H | CH3 | OCF2CHFBr | CH | |
| H | H | H | OCH3 | OCF2CHFBr | CH | |
| H | H | H | CH3 | OCF2CF2H | CH | |
| H | H | H | OCH3 | OCF2CF2H | CH | |
| H | H | H | CH3 | OCF2CHFCF3 | CH | |
| H | H | H | OCH3 | OCF2CHFCF3 | CH | |
| H | H | H | OCF2H | OCF2H | CH | |
| H | H | H | OCF2H | SCF2H | CH | |
| H | H | H | SCF2H | SCF2H | CH | |
| H | H | H | CH3 | OCF2H | N | |
| H | H | H | OCH3 | OCF2H | N | |
| H | H | H | CH3 | SCF2H | N | |
| H | H | H | OCH3 | SCF2H | N | |
| H | H | H | CH3 | OCF2CHFCl | N | |
| H | H | H | OCH3 | OCF2CHFCl | N | |
| H | H | H | CH3 | OCF2CHFBr | N | |
| H | H | H | OCH3 | OCF2CHFBr | N | |
| H | H | H | CH3 | OCF2CF2H | N | |
| H | H | H | OCH3 | OCF2CF2H | N | |
| H | H | H | CH3 | OCF2CHFCF3 | N | |
| H | H | H | OCH3 | OCF2CHFCF3 | N | |
| H | H | H | OCF2H | OCF2H | N | |

TABLE IIa

[In Formula I] Q is

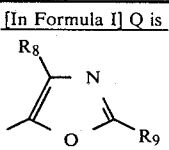

| R | R8 | R9 | X | Y | Z | m.p. (°C.) |
|---|---|---|---|---|---|---|
| H | H | H | CH3 | CH3 | CH | |
| H | H | H | OCH3 | OCH3 | CH | |
| H | H | H | CH3 | OCH3 | CH | |
| H | H | H | CH3 | CH3 | N | |
| H | H | H | OCH3 | OCH3 | N | |
| H | H | H | CH3 | OCH3 | N | |
| H | H | H | Cl | OCH3 | CH | |
| H | H | H | CH3 | C2H5 | CH | |
| H | H | H | OCH3 | CH2OCH3 | N | |
| H | H | H | CH3 | OC2H5 | N | |
| H | H | H | OCH3 | OC2H5 | CH | |
| H | H | H | OCH3 | CH(OCH3)2 | CH | |
| H | CH3 | H | OCH3 | OCH3 | CH | |
| H | C2H5 | H | OCH3 | OCH3 | CH | |
| H | H | CH3 | OCH3 | OCH3 | CH | |
| H | H | C2H5 | OCH3 | OCH3 | CH | |
| H | H | H | OCH3 | OCH2CF3 | CH | |
| H | H | H | CH3 | OCH2CF3 | N | |

TABLE IIa-continued

[In Formula I] Q is

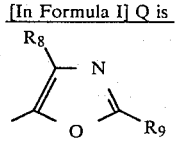

| R | R8 | R9 | X | Y | Z | m.p. (°C.) |
|---|---|---|---|---|---|---|
| H | H | H | CH3 |  | CH | |
| H | H | H | CH3 | OCF2H | CH | |
| H | H | H | OCH3 | OCF2H | CH | |
| H | H | H | CH3 | SCF2H | CH | |
| H | H | H | OCH3 | SCF2H | CH | |
| H | H | H | CH3 | OCF2CHFCl | CH | |
| H | H | H | OCH3 | OCF2CHFCl | CH | |
| H | H | H | CH3 | OCF2CHFBr | CH | |
| H | H | H | OCH3 | OCF2CHFBr | CH | |
| H | H | H | CH3 | OCF2CF2H | CH | |
| H | H | H | OCH3 | OCF2CF2H | CH | |
| H | H | H | CH3 | OCF2CHFCF3 | CH | |
| H | H | H | OCH3 | OCF2CHFCF3 | CH | |
| H | H | H | OCF2H | OCF2H | CH | |
| H | H | H | OCF2H | SCF2H | CH | |
| H | H | H | SCF2H | SCF2H | CH | |
| H | H | H | CH3 | OCF2H | N | |
| H | H | H | OCH3 | OCF2H | N | |
| H | H | H | CH3 | SCF2H | N | |
| H | H | H | OCH3 | SCF2H | N | |
| H | H | H | CH3 | OCF2CHFCl | N | |
| H | H | H | OCH3 | OCF2CHFCl | N | |
| H | H | H | CH3 | OCF2CHFBr | N | |
| H | H | H | OCH3 | OCF2CHFBr | N | |
| H | H | H | CH3 | OCF2CF2H | N | |
| H | H | H | OCH3 | OCF2CF2H | N | |
| H | H | H | CH3 | OCF2CHFCF3 | N | |
| H | H | H | OCH3 | OCF2CHFCF3 | N | |
| H | H | H | OCF2H | OCF2H | N | |

TABLE IIb

[In Formula I] Q is

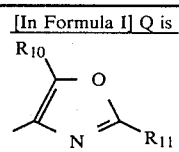

| R | R10 | R11 | X | Y | Z | m.p. (°C.) |
|---|---|---|---|---|---|---|
| H | H | H | CH3 | CH3 | CH | |
| H | H | H | OCH3 | OCH3 | CH | |
| H | H | H | CH3 | OCH3 | CH | |
| H | H | H | CH3 | CH3 | N | |
| H | H | H | OCH3 | OCH3 | N | |
| H | H | H | CH3 | OCH3 | N | |
| H | H | H | Cl | OCH3 | CH | |
| H | H | H | CH3 | C2H5 | CH | |
| H | H | H | OCH3 | CH2OCH3 | N | |
| H | H | H | CH3 | OC2H5 | N | |
| H | H | H | OCH3 | OC2H5 | CH | |
| H | H | H | OCH3 | CH(OCH3)2 | CH | |
| H | CH3 | H | OCH3 | OCH3 | CH | |
| H | C2H5 | H | OCH3 | OCH3 | CH | |
| H | H | CH3 | OCH3 | OCH3 | CH | |
| H | H | C2H5 | OCH3 | OCH3 | CH | |
| H | H | H | OCH3 | OCH2CF3 | CH | |
| H | H | H | CH3 | OCH2CF3 | N | |
| H | H | H | OCH3 | (cyclic acetal) | CH | |
| H | H | H | CH3 | OCF2H | CH | |
| H | H | H | OCH3 | OCF2H | CH | |

TABLE IIb-continued

[In Formula I] Q is

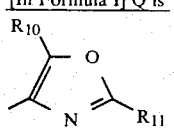

| R | R10 | R11 | X | Y | Z | m.p. (°C.) |
|---|---|---|---|---|---|---|
| H | H | H | CH3 | SCF2H | CH | |
| H | H | H | OCH3 | SCF2H | CH | |
| H | H | H | CH3 | OCF2CHFCl | CH | |
| H | H | H | OCH3 | OCF2CHFCl | CH | |
| H | H | H | CH3 | OCF2CHFBr | CH | |
| H | H | H | OCH3 | OCF2CHFBr | CH | |
| H | H | H | CH3 | OCF2CF2H | CH | |
| H | H | H | OCH3 | OCF2CF2H | CH | |
| H | H | H | CH3 | OCF2CHFCF3 | CH | |
| H | H | H | OCH3 | OCF2CHFCF3 | CH | |
| H | H | H | OCF2H | OCF2H | CH | |
| H | H | H | OCF2H | SCF2H | CH | |
| H | H | H | SCF2H | SCF2H | CH | |
| H | H | H | CH3 | OCF2H | N | |
| H | H | H | OCH3 | OCF2H | N | |
| H | H | H | CH3 | SCF2H | N | |
| H | H | H | OCH3 | SCF2H | N | |
| H | H | H | CH3 | OCF2CHFCl | N | |
| H | H | H | OCH3 | OCF2CHFCl | N | |
| H | H | H | CH3 | OCF2CHFBr | N | |
| H | H | H | OCH3 | OCF2CHFBr | N | |
| H | H | H | CH3 | OCF2CF2H | N | |
| H | H | H | OCH3 | OCF2CF2H | N | |
| H | H | H | CH3 | OCF2CHFCF3 | N | |
| H | H | H | OCH3 | OCF2CHFCF3 | N | |
| H | H | H | OCF2H | OCF2H | N | |

TABLE IIc

[In Formula I] Q is

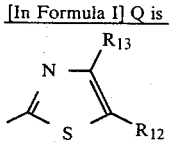

| R | R12 | R13 | X | Y | Z | m.p. (°C.) |
|---|---|---|---|---|---|---|
| H | H | H | CH3 | CH3 | CH | |
| H | H | H | OCH3 | OCH3 | CH | |
| H | H | H | CH3 | OCH3 | CH | |
| H | H | H | CH3 | CH3 | N | |
| H | H | H | OCH3 | OCH3 | N | |
| H | H | H | CH3 | OCH3 | N | |
| H | H | H | Cl | OCH3 | CH | |
| H | H | H | CH3 | C2H5 | CH | |
| H | H | H | OCH3 | CH2OCH3 | N | |
| H | H | H | CH3 | OC2H5 | N | |
| H | H | H | OCH3 | OC2H5 | CH | |
| H | H | H | OCH3 | CH(OCH3)2 | CH | |
| H | CH3 | H | OCH3 | OCH3 | CH | |
| H | C2H5 | H | OCH3 | OCH3 | CH | |
| H | H | CH3 | OCH3 | OCH3 | CH | |
| H | H | C2H5 | OCH3 | OCH3 | CH | |
| 5-F | H | H | OCH3 | OCH3 | CH | |
| 6-Cl | H | H | OCH3 | OCH3 | CH | |
| 6-Br | H | H | OCH3 | OCH3 | CH | |
| 5-CF3 | H | H | OCH3 | OCH3 | CH | |
| 5-OCH3 | H | H | OCH3 | OCH3 | CH | |
| 3-CH3 | H | H | OCH3 | OCH3 | CH | |
| H | H | H | OCH3 | OCH2CF3 | CH | |
| H | H | H | CH3 |  | CH | |
| H | H | H | CH3 | OCF2H | CH | |
| H | H | H | OCH3 | OCF2H | CH | |
| H | H | H | CH3 | SCF2H | CH | |
| H | H | H | OCH3 | SCF2H | CH | |
| H | H | H | CH3 | OCF2CHFCl | CH | |

TABLE IIc-continued

[In Formula I] Q is

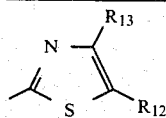

| R | R12 | R13 | X | Y | Z | m.p. (°C.) |
|---|---|---|---|---|---|---|
| H | H | H | OCH3 | OCF2CHFCl | CH | |
| H | H | H | CH3 | OCF2CHFBr | CH | |
| H | H | H | OCH3 | OCF2CHFBr | CH | |
| H | H | H | CH3 | OCF2CF2H | CH | |
| H | H | H | OCH3 | OCF2CF2H | CH | |
| H | H | H | CH3 | OCF2CHFCF3 | CH | |
| H | H | H | OCH3 | OCF2CHFCF3 | CH | |
| H | H | H | OCF2H | OCF2H | CH | |
| H | H | H | OCF2H | SCF2H | CH | |
| H | H | H | SCF2H | SCF2H | CH | |
| H | H | H | CH3 | OCF2H | N | |
| H | H | H | OCH3 | OCF2H | N | |
| H | H | H | CH3 | SCF2H | N | |
| H | H | H | OCH3 | SCF2H | N | |
| H | H | H | CH3 | OCF2CHFCl | N | |
| H | H | H | OCH3 | OCF2CHFCl | N | |
| H | H | H | CH3 | OCF2CHFBr | N | |
| H | H | H | OCH3 | OCF2CHFBr | N | |
| H | H | H | CH3 | OCF2CF2H | N | |
| H | H | H | OCH3 | OCF2CF2H | N | |
| H | H | H | CH3 | OCF2CHFCF3 | N | |
| H | H | H | OCH3 | OCF2CHFCF3 | N | |
| H | H | H | OCF2H | OCF2H | N | |

TABLE IId

[In Formula I] Q is

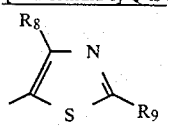

| R | R8 | R9 | X | Y | Z | m.p. (°C.) |
|---|---|---|---|---|---|---|
| H | H | H | CH3 | CH3 | CH | |
| H | H | H | OCH3 | OCH3 | CH | |
| H | H | H | CH3 | OCH3 | CH | |
| H | H | H | CH3 | CH3 | N | |
| H | H | H | OCH3 | OCH3 | N | |
| H | H | H | CH3 | OCH3 | N | |
| H | H | H | Cl | OCH3 | CH | |
| H | H | H | CH3 | C2H5 | CH | |
| H | H | H | OCH3 | CH2OCH3 | N | |
| H | H | H | CH3 | OC2H5 | N | |
| H | H | H | OCH3 | OC2H5 | CH | |
| H | H | H | OCH3 | CH(OCH3)2 | CH | |
| H | CH3 | H | OCH3 | OCH3 | CH | |
| H | C2H5 | H | OCH3 | OCH3 | CH | |
| H | H | CH3 | OCH3 | OCH3 | CH | |
| H | H | C2H5 | OCH3 | OCH3 | CH | |
| H | H | H | OCH3 | OCH2CF3 | CH | |
| H | H | H | OCH3 | OCH2CF3 | N | |
| H | H | H | CH3 |  | CH | |
| H | H | H | CH3 | OCF2H | CH | |
| H | H | H | OCH3 | OCF2H | CH | |
| H | H | H | CH3 | SCF2H | CH | |
| H | H | H | OCH3 | SCF2H | CH | |
| H | H | H | CH3 | OCF2CHFCl | CH | |
| H | H | H | OCH3 | OCF2CHFCl | CH | |
| H | H | H | CH3 | OCF2CHFBr | CH | |
| H | H | H | OCH3 | OCF2CHFBr | CH | |
| H | H | H | CH3 | OCF2CF2H | CH | |
| H | H | H | OCH3 | OCF2CF2H | CH | |
| H | H | H | CH3 | OCF2CHFCF3 | CH | |
| H | H | H | OCH3 | OCF2CHFCF3 | CH | |
| H | H | H | OCF2H | OCF2H | CH | |

TABLE IId-continued

[In Formula I] Q is $$\underset{S}{\overset{R_8}{\diagdown}}\underset{}{\overset{N}{=}}R_9$$

| R | R8 | R9 | X | Y | Z | m.p. (°C.) |
|---|----|----|---|---|---|------------|
| H | H | H | OCF$_2$H | SCF$_2$H | CH | |
| H | H | H | SCF$_2$H | SCF$_2$H | CH | |
| H | H | H | CH$_3$ | OCF$_2$H | N | |
| H | H | H | OCH$_3$ | OCF$_2$H | N | |
| H | H | H | CH$_3$ | SCF$_2$H | N | |
| H | H | H | OCH$_3$ | SCF$_2$H | N | |
| H | H | H | CH$_3$ | OCF$_2$CHFCl | N | |
| H | H | H | OCH$_3$ | OCF$_2$CHFCl | N | |
| H | H | H | CH$_3$ | OCF$_2$CHFBr | N | |
| H | H | H | OCH$_3$ | OCF$_2$CHFBr | N | |
| H | H | H | CH$_3$ | OCF$_2$CF$_2$H | N | |
| H | H | H | OCH$_3$ | OCF$_2$CF$_2$H | N | |
| H | H | H | CH$_3$ | OCF$_2$CHFCF$_3$ | N | |
| H | H | H | OCH$_3$ | OCF$_2$CHFCF$_3$ | N | |
| H | H | H | OCF$_2$H | OCF$_2$H | N | |

TABLE IIe

[In Formula I] Q is $$\underset{N}{\overset{R_{10}}{\diagdown}}\underset{}{\overset{S}{=}}R_{11}$$

| R | R10 | R11 | X | Y | Z | m.p. (°C.) |
|---|-----|-----|---|---|---|------------|
| H | H | H | CH$_3$ | CH$_3$ | CH | |
| H | H | H | OCH$_3$ | OCH$_3$ | CH | |
| H | H | H | CH$_3$ | CH$_3$ | N | |
| H | H | H | OCH$_3$ | OCH$_3$ | N | |
| H | H | H | CH$_3$ | OCH$_3$ | N | |
| H | H | H | Cl | OCH$_3$ | CH | |
| H | H | H | CH$_3$ | C$_2$H$_5$ | CH | |
| H | H | H | OCH$_3$ | CH$_2$OCH$_3$ | N | |
| H | H | H | CH$_3$ | OC$_2$H$_5$ | N | |
| H | H | H | OCH$_3$ | OC$_2$H$_5$ | CH | |
| H | H | H | CH$_3$ | CH(OCH$_3$)$_2$ | CH | |
| H | CH$_3$ | H | OCH$_3$ | OCH$_3$ | CH | |
| H | C$_2$H$_5$ | H | OCH$_3$ | OCH$_3$ | CH | |
| H | H | CH$_3$ | OCH$_3$ | OCH$_3$ | CH | |
| H | H | C$_2$H$_5$ | OCH$_3$ | OCH$_3$ | CH | |
| H | H | H | CH$_3$ | OCH$_2$CF$_3$ | CH | |
| H | H | H | CH$_3$ | OCH$_2$CF$_3$ | N | |
| H | H | H | OCH$_3$ | 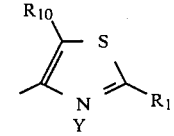 | CH | |
| H | H | H | Cl | OC$_2$H$_5$ | CH | |
| H | H | H | CH$_3$ | OCF$_2$H | CH | |
| H | H | H | OCH$_3$ | OCF$_2$H | CH | |
| H | H | H | CH$_3$ | SCF$_2$H | CH | |
| H | H | H | OCH$_3$ | SCF$_2$H | CH | |
| H | H | H | CH$_3$ | OCF$_2$CHFCl | CH | |
| H | H | H | OCH$_3$ | OCF$_2$CHFCl | CH | |
| H | H | H | CH$_3$ | OCF$_2$CHFBr | CH | |
| H | H | H | OCH$_3$ | OCF$_2$CHFBr | CH | |
| H | H | H | CH$_3$ | OCF$_2$CF$_2$H | CH | |
| H | H | H | OCH$_3$ | OCF$_2$CF$_2$H | CH | |
| H | H | H | CH$_3$ | OCF$_2$CHFCF$_3$ | CH | |
| H | H | H | OCH$_3$ | OCF$_2$CHFCF$_3$ | CH | |
| H | H | H | OCF$_2$H | OCF$_2$H | CH | |
| H | H | H | OCF$_2$H | SCF$_2$H | CH | |
| H | H | H | SCF$_2$H | SCF$_2$H | CH | |
| H | H | H | CH$_3$ | OCF$_2$H | N | |
| H | H | H | OCH$_3$ | OCF$_2$H | N | |
| H | H | H | CH$_3$ | SCF$_2$H | N | |
| H | H | H | OCH$_3$ | SCF$_2$H | N | |
| H | H | H | CH$_3$ | OCF$_2$CHFCl | N | |
| H | H | H | OCH$_3$ | OCF$_2$CHFCl | N | |

TABLE IIe-continued

[In Formula I] Q is $$\underset{N}{\overset{R_{10}}{\diagdown}}\underset{}{\overset{S}{=}}R_{11}$$

| R | R10 | R11 | X | Y | Z | m.p. (°C.) |
|---|-----|-----|---|---|---|------------|
| H | H | H | CH$_3$ | OCF$_2$CHFBr | N | |
| H | H | H | OCH$_3$ | OCF$_2$CHFBr | N | |
| H | H | H | CH$_3$ | OCF$_2$CF$_2$H | N | |
| H | H | H | OCH$_3$ | OCF$_2$CF$_2$H | N | |
| H | H | H | CH$_3$ | OCF$_2$CHFCF$_3$ | N | |
| H | H | H | OCH$_3$ | OCF$_2$CHFCF$_3$ | N | |
| H | H | H | OCF$_2$H | OCF$_2$H | N | |

TABLE III

[In Formula I] Q is

| R | R14 | X | Y | Z | m.p.(°C.) |
|---|-----|---|---|---|-----------|
| H | H | CH$_3$ | CH$_3$ | CH | 87–92° |
| H | H | OCH$_3$ | OCH$_3$ | CH | 161–164° |
| H | H | CH$_3$ | OCH$_3$ | CH | 92–97° |
| H | H | CH$_3$ | CH$_3$ | N | 139–144° |
| H | H | OCH$_3$ | OCH$_3$ | N | 168–173° |
| H | H | CH$_3$ | OCH$_3$ | N | 167–171° |
| H | H | Cl | OCH$_3$ | CH | 153–157° |
| H | H | CH$_3$ | C$_2$H$_5$ | CH | |
| H | H | OCH$_3$ | CH$_2$OCH$_3$ | N | |
| H | H | CH$_3$ | OC$_2$H$_5$ | N | |
| H | H | OCH$_3$ | OC$_2$H$_5$ | CH | |
| H | H | CH$_3$ | CH(OCH$_3$)$_2$ | CH | |
| H | CH$_3$ | CH$_3$ | CH$_3$ | CH | |
| H | CH$_3$ | OCH$_3$ | OCH$_3$ | CH | 149–152° |
| H | CH$_3$ | CH$_3$ | OCH$_3$ | CH | |
| H | CH$_3$ | CH$_3$ | CH$_3$ | N | |
| H | CH$_3$ | OCH$_3$ | OCH$_3$ | N | |
| H | CH$_3$ | CH$_3$ | OCH$_3$ | N | |
| H | CH$_3$ | Cl | OCH$_3$ | CH | |
| H | CH$_3$ | CH$_3$ | C$_2$H$_5$ | CH | |
| H | CH$_3$ | OCH$_3$ | CH$_2$OCH$_3$ | N | |
| H | CH$_3$ | CH$_3$ | OC$_2$H$_5$ | N | |
| H | CH$_3$ | OCH$_3$ | OC$_2$H$_5$ | CH | |
| H | CH$_3$ | CH$_3$ | CH(OCH$_3$)$_2$ | CH | |
| H | C$_2$H$_5$ | CH$_3$ | CH$_3$ | CH | |
| H | C$_2$H$_5$ | OCH$_3$ | OCH$_3$ | CH | 149–153° |
| H | C$_2$H$_5$ | CH$_3$ | OCH$_3$ | CH | |
| H | C$_2$H$_5$ | CH$_3$ | CH$_3$ | N | |
| H | C$_2$H$_5$ | OCH$_3$ | OCH$_3$ | N | |
| H | C$_2$H$_5$ | CH$_3$ | OCH$_3$ | N | |
| H | C$_2$H$_5$ | Cl | OCH$_3$ | CH | |
| H | C$_2$H$_5$ | CH$_3$ | C$_2$H$_5$ | CH | |
| H | C$_2$H$_5$ | OCH$_3$ | CH$_2$OCH$_3$ | N | |
| H | C$_2$H$_5$ | CH$_3$ | OC$_2$H$_5$ | N | |
| H | C$_2$H$_5$ | OCH$_3$ | OC$_2$H$_5$ | CH | |
| H | C$_2$H$_5$ | CH$_3$ | CH(OCH$_3$)$_2$ | CH | |
| 5-F | CH$_3$ | OCH$_3$ | OCH$_3$ | CH | |
| 6-Cl | CH$_3$ | OCH$_3$ | OCH$_3$ | CH | |
| 6-Br | CH$_3$ | OCH$_3$ | OCH$_3$ | CH | |
| 3-CH$_3$ | CH$_3$ | OCH$_3$ | OCH$_3$ | CH | |
| 5-CF$_3$ | CH$_3$ | OCH$_3$ | OCH$_3$ | CH | |
| 5-OCH$_3$ | CH$_3$ | OCH$_3$ | OCH$_3$ | CH | |
| H | H | Cl | OC$_2$H$_5$ | CH | |
| H | CH$_3$ | Cl | OC$_2$H$_5$ | CH | |
| H | C$_2$H$_5$ | Cl | OC$_2$H$_5$ | CH | |
| H | H | OCH$_3$ | CH(OCH$_3$)$_2$ | CH | |
| H | CH$_3$ | OCH$_3$ | CH(OCH$_3$)$_2$ | CH | |
| H | C$_2$H$_5$ | OCH$_3$ | CH(OCH$_3$)$_2$ | CH | |
| 6-CH$_3$ | C$_2$H$_5$ | OCH$_3$ | OCH$_3$ | CH | 180–182° |
| H | H | OCH$_3$ | OCH$_2$CF$_3$ | CH | |
| H | H | CH$_3$ | OCH$_2$CF$_3$ | CH | |
| H | H | OCH$_3$ | OCH$_2$CF$_3$ | N | |
| H | CH$_3$ | OCH$_3$ | OCH$_2$CF$_3$ | CH | |
| H | CH$_3$ | OCH$_3$ | OCH$_2$CF$_3$ | N | |

TABLE III-continued

[In Formula I] Q is

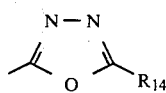

| R | R14 | X | Y | Z | m.p.(°C.) |
|---|---|---|---|---|---|
| H | C2H5 | OCH3 | OCH2CF3 | CH | |
| H | H | OCH3 | O-CH(-O-)(ring) | CH | |
| H | CH3 | OCH3 | O-CH(-O-)(ring) | CH | |
| H | H | CH3 | O-CH(-O-)(ring) | CH | |
| H | H | CH3 | OCF2H | CH | |
| H | H | OCH3 | OCF2H | CH | |
| H | H | CH3 | SCF2H | CH | |
| H | H | OCH3 | SCF2H | CH | |
| H | H | CH3 | OCF2CHFCl | CH | |
| H | H | OCH3 | OCF2CHFCl | CH | |
| H | H | CH3 | OCF2CHFBr | CH | |
| H | H | OCH3 | OCF2CHFBr | CH | |
| H | H | CH3 | OCF2CF2H | CH | |
| H | H | OCH3 | OCF2CF2H | CH | |
| H | H | CH3 | OCF2CHFCF3 | CH | |
| H | H | OCH3 | OCF2CHFCF3 | CH | |
| H | H | OCF2H | OCF2H | CH | |
| H | H | OCF2H | SCF2H | CH | |
| H | H | SCF2H | SCF2H | CH | |
| H | H | CH3 | OCF2H | N | |
| H | H | OCH3 | OCF2H | N | |
| H | H | CH3 | SCF2H | N | |
| H | H | OCH3 | SCF2H | N | |
| H | H | CH3 | OCF2CHFCl | N | |
| H | H | OCH3 | OCF2CHFCl | N | |
| H | H | CH3 | OCF2CHFBr | N | |
| H | H | OCH3 | OCF2CHFBr | N | |
| H | H | CH3 | OCF2CF2H | N | |
| H | H | OCH3 | OCF2CF2H | N | |
| H | H | CH3 | OCF2CHFCF3 | N | |
| H | H | OCH3 | OCF2CHFCF3 | N | |
| H | H | OCF2H | OCF2H | N | |

TABLE IIIa

[In Formula I] Q is

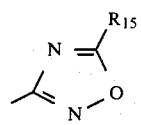

| R | R15 | X | Y | Z | m.p. (°C.) |
|---|---|---|---|---|---|
| H | H | CH3 | CH3 | CH | |
| H | H | OCH3 | OCH3 | CH | |
| H | H | CH3 | CH3 | N | |
| H | H | OCH3 | OCH3 | N | |
| H | H | CH3 | OCH3 | N | |
| H | H | Cl | OCH3 | CH | |
| H | H | CH3 | C2H5 | CH | |
| H | H | OCH3 | CH2OCH3 | N | |
| H | H | CH3 | OC2H5 | N | |
| H | H | OCH3 | OC2H5 | CH | |
| H | H | CH3 | CH(OCH3)2 | CH | |

TABLE IIIa-continued

[In Formula I] Q is

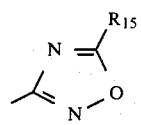

| R | R15 | X | Y | Z | m.p. (°C.) |
|---|---|---|---|---|---|
| H | CH3 | CH3 | CH3 | CH | |
| H | CH3 | OCH3 | OCH3 | CH | |
| H | CH3 | CH3 | CH3 | N | |
| H | CH3 | OCH3 | OCH3 | N | |
| H | CH3 | CH3 | OCH3 | N | |
| H | CH3 | Cl | OCH3 | CH | |
| H | CH3 | CH3 | C2H5 | CH | |
| H | CH3 | OCH3 | CH2OCH3 | N | |
| H | CH3 | CH3 | OC2H5 | N | |
| H | CH3 | OCH3 | OC2H5 | CH | |
| H | CH3 | OCH3 | CH(OCH3)2 | CH | |
| H | C2H5 | CH3 | CH3 | CH | |
| H | C2H5 | OCH3 | OCH3 | CH | |
| H | C2H5 | CH3 | OCH3 | CH | |
| H | C2H5 | CH3 | CH3 | N | |
| H | C2H5 | OCH3 | OCH3 | N | |
| H | C2H5 | CH3 | OCH3 | N | |
| H | C2H5 | Cl | OCH3 | CH | |
| H | C2H5 | CH3 | C2H5 | CH | |
| H | C2H5 | OCH3 | CH2OCH3 | N | |
| H | C2H5 | CH3 | OC2H5 | N | |
| H | C2H5 | OCH3 | OC2H5 | CH | |
| H | C2H5 | CH3 | CH(OCH3)2 | CH | |
| 5-F | CH3 | OCH3 | OCH3 | CH | |
| 6-Cl | CH3 | OCH3 | OCH3 | CH | |
| 6-Br | CH3 | OCH3 | OCH3 | CH | |
| 3-CH3 | CH3 | OCH3 | OCH3 | CH | |
| 5-CF3 | CH3 | OCH3 | OCH3 | CH | |
| 5-OCH3 | CH3 | OCH3 | OCH3 | CH | |
| H | H | OCH3 | OCH2CF3 | CH | |
| H | H | CH3 | OCH2CF3 | N | |
| H | H | OCH3 | O-CH(-O-)(ring) | CH | |
| H | H | CH3 | OCF2H | CH | |
| H | H | OCH3 | OCF2H | CH | |
| H | H | CH3 | SCF2H | CH | |
| H | H | OCH3 | SCF2H | CH | |
| H | H | CH3 | OCF2CHFCl | CH | |
| H | H | OCH3 | OCF2CHFCl | CH | |
| H | H | CH3 | OCF2CHFBr | CH | |
| H | H | OCH3 | OCF2CHFBr | CH | |
| H | H | CH3 | OCF2CF2H | CH | |
| H | H | OCH3 | OCF2CF2H | CH | |
| H | H | CH3 | OCF2CHFCF3 | CH | |
| H | H | OCH3 | OCF2CHFCF3 | CH | |
| H | H | OCF2H | OCF2H | CH | |
| H | H | OCF2H | SCF2H | CH | |
| H | H | SCF2H | SCF2H | CH | |
| H | H | CH3 | OCF2H | N | |
| H | H | OCH3 | OCF2H | N | |
| H | H | CH3 | SCF2H | N | |
| H | H | OCH3 | SCF2H | N | |
| H | H | CH3 | OCF2CHFCl | N | |
| H | H | OCH3 | OCF2CHFCl | N | |
| H | H | CH3 | OCF2CHFBr | N | |
| H | H | OCH3 | OCF2CHFBr | N | |
| H | H | CH3 | OCF2CF2H | N | |
| H | H | OCH3 | OCF2CF2H | N | |
| H | H | CH3 | OCF2CHFCF3 | N | |
| H | H | OCH3 | OCF2CHFCF3 | N | |
| H | H | OCF2H | OCF2H | N | |

TABLE IIIb

[In Formula I] Q is

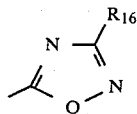

| R | R16 | X | Y | Z | m.p. (°C.) |
|---|---|---|---|---|---|
| H | H | CH3 | CH3 | CH | |
| H | H | OCH3 | OCH3 | CH | |
| H | H | CH3 | OCH3 | CH | |
| H | H | CH3 | CH3 | N | |
| H | H | OCH3 | OCH3 | N | |
| H | H | CH3 | OCH3 | N | |
| H | CH3 | CH3 | CH3 | CH | |
| H | CH3 | OCH3 | OCH3 | CH | |
| H | CH3 | CH3 | OCH3 | CH | |
| H | CH3 | CH3 | CH3 | N | |
| H | CH3 | OCH3 | OCH3 | N | |
| H | CH3 | CH3 | OCH3 | N | |
| H | C2H5 | CH3 | CH3 | CH | |
| H | C2H5 | OCH3 | OCH3 | CH | |
| H | C2H5 | CH3 | OCH3 | CH | |
| H | C2H5 | CH3 | CH3 | N | |
| H | C2H5 | CH3 | OCH3 | N | |
| H | C2H5 | OCH3 | OCH3 | N | |
| H | CH3 | Cl | OCH3 | CH | |
| H | CH3 | CH3 | C2H5 | CH | |
| H | CH3 | OCH3 | CH2OCH3 | CH | |
| H | CH3 | CH3 | OC2H5 | N | |
| H | CH3 | CH3 | OC2H5 | CH | |
| H | CH3 | CH3 | CH(OCH3)2 | CH | |
| H | H | Cl | OCH3 | CH | |
| H | CH3 | OCH3 | OCH2CF3 | CH | |
| H | CH3 | OCH3 | 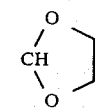 | CH | |
| H | H | CH3 | OCF2H | CH | |
| H | H | OCH3 | OCF2H | CH | |
| H | H | CH3 | SCF2H | CH | |
| H | H | OCH3 | SCF2H | CH | |
| H | H | CH3 | OCF2CHFCl | CH | |
| H | H | OCH3 | OCF2CHFCl | CH | |
| H | H | CH3 | OCF2CHFBr | CH | |
| H | H | OCH3 | OCF2CHFBr | CH | |
| H | H | CH3 | OCF2CF2H | CH | |
| H | H | OCH3 | OCF2CF2H | CH | |
| H | H | CH3 | OCF2CHFCF3 | CH | |
| H | H | OCH3 | OCF2CHFCF3 | CH | |
| H | H | OCF2H | OCF2H | CH | |
| H | H | OCF2H | SCF2H | CH | |
| H | H | SCF2H | SCF2H | CH | |
| H | H | CH3 | OCF2H | N | |
| H | H | OCH3 | OCF2H | N | |
| H | H | CH3 | SCF2H | N | |
| H | H | OCH3 | SCF2H | N | |
| H | H | CH3 | OCF2CHFCl | N | |
| H | H | OCH3 | OCF2CHFCl | N | |
| H | H | CH3 | OCF2CHFBr | N | |
| H | H | OCH3 | OCF2CHFBr | N | |
| H | H | CH3 | OCF2CF2H | N | |
| H | H | OCH3 | OCF2CF2H | N | |
| H | H | CH3 | OCF2CHFCF3 | N | |
| H | H | OCH3 | OCF2CHFCF3 | N | |
| H | H | OCF2H | OCF2H | N | |

TABLE IIIc

[In Formula I] Q is

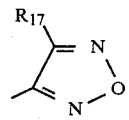

| R | R17 | X | Y | Z | m.p.(°C.) |
|---|---|---|---|---|---|
| H | H | CH3 | CH3 | CH | |
| H | H | OCH3 | OCH3 | CH | |
| H | H | CH3 | OCH3 | CH | |
| H | H | CH3 | CH3 | N | |
| H | H | CH3 | OCH3 | N | |
| H | H | OCH3 | OCH3 | N | |
| H | CH3 | OCH3 | OCH3 | CH | |
| H | CH3 | CH3 | OCH3 | CH | |
| H | CH3 | CH3 | CH3 | CH | |
| H | CH3 | OCH3 | OCH3 | N | |
| H | CH3 | CH3 | OCH3 | N | |
| H | H | Cl | OCH3 | CH | |
| H | H | CH3 | C2H5 | CH | |
| H | H | OCH3 | CH2OCH3 | N | |
| H | H | CH3 | OC2H5 | N | |
| H | H | OCH3 | OC2H5 | CH | |
| H | H | OCH3 | CH(OCH3)2 | CH | |
| H | H | OCH3 | OCH2CF3 | CH | |
| H | H | OCH3 | OCH2CF3 | N | |
| H | H | OCH3 |  | CH | |
| H | H | CH3 | OCF2H | CH | |
| H | H | OCH3 | OCF2H | CH | |
| H | H | CH3 | SCF2H | CH | |
| H | H | OCH3 | SCF2H | CH | |
| H | H | CH3 | OCF2CHFCl | CH | |
| H | H | OCH3 | OCF2CHFCl | CH | |
| H | H | CH3 | OCF2CHFBr | CH | |
| H | H | OCH3 | OCF2CHFBr | CH | |
| H | H | CH3 | OCF2CF2H | CH | |
| H | H | OCH3 | OCF2CF2H | CH | |
| H | H | CH3 | OCF2CHFCF3 | CH | |
| H | H | OCH3 | OCF2CHFCF3 | CH | |
| H | H | OCF2H | OCF2H | CH | |
| H | H | OCF2H | SCF2H | CH | |
| H | H | SCF2H | SCF2H | CH | |
| H | H | CH3 | OCF2H | N | |
| H | H | OCH3 | OCF2H | N | |
| H | H | CH3 | SCF2H | N | |
| H | H | OCH3 | SCF2H | N | |
| H | H | CH3 | OCF2CHFCl | N | |
| H | H | OCH3 | OCF2CHFCl | N | |
| H | H | CH3 | OCF2CHFBr | N | |
| H | H | OCH3 | OCF2CHFBr | N | |
| H | H | CH3 | OCF2CF2H | N | |
| H | H | OCH3 | OCF2CF2H | N | |
| H | H | CH3 | OCF2CHFCF3 | N | |
| H | H | OCH3 | OCF2CHFCF3 | N | |
| H | H | OCF2H | OCF2H | N | |

TABLE IIId

[In Formula I] Q is

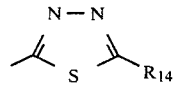

| R | R14 | X | Y | Z | m.p.(°C.) |
|---|---|---|---|---|---|
| H | H | CH3 | CH3 | CH | |
| H | H | OCH3 | OCH3 | CH | |
| H | H | CH3 | OCH3 | CH | |
| H | H | CH3 | CH3 | N | |
| H | H | OCH3 | OCH3 | N | |
| H | H | CH3 | OCH3 | N | |

TABLE IIId-continued

[In Formula I] Q is

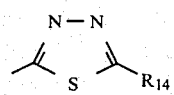

| R | R14 | X | Y | Z | m.p.(°C.) |
|---|-----|---|---|---|-----------|
| H | H | Cl | OCH3 | CH | |
| H | H | CH3 | C2H5 | CH | |
| H | H | OCH3 | CH2OCH3 | N | |
| H | H | CH3 | OC2H5 | N | |
| H | H | OCH3 | OC2H5 | CH | |
| H | H | OCH3 | CH(OCH3)2 | CH | |
| H | CH3 | CH3 | CH3 | CH | |
| H | CH3 | CH3 | OCH3 | CH | |
| H | CH3 | OCH3 | OCH3 | CH | |
| H | CH3 | CH3 | CH3 | N | |
| H | CH3 | CH3 | OCH3 | N | |
| H | CH3 | OCH3 | OCH3 | N | |
| H | C2H5 | OCH3 | OCH3 | CH | |
| H | C2H5 | OCH3 | CH3 | CH | |
| H | C2H5 | CH3 | CH3 | CH | |
| H | C2H5 | OCH3 | OCH3 | N | |
| H | C2H5 | OCH3 | CH3 | N | |
| H | CH3 | Cl | OCH3 | CH | |
| H | C2H5 | Cl | OCH3 | CH | |
| H | CH3 | CH3 | OCH2CF3 | N | |
| H | CH3 | OCH3 |  | CH | |
| H | H | CH3 | OCF2H | CH | |
| H | H | OCH3 | OCF2H | CH | |
| H | H | CH3 | SCF2H | CH | |
| H | H | OCH3 | SCF2H | CH | |
| H | H | CH3 | OCF2CHFCl | CH | |
| H | H | OCH3 | OCF2CHFCl | CH | |
| H | H | CH3 | OCF2CHFBr | CH | |
| H | H | OCH3 | OCF2CHFBr | CH | |
| H | H | CH3 | OCF2CF2H | CH | |
| H | H | OCH3 | OCF2CF2H | CH | |
| H | H | CH3 | OCF2CHFCF3 | CH | |
| H | H | OCH3 | OCF2CHFCF3 | CH | |
| H | H | OCF2H | OCF2H | CH | |
| H | H | OCF2H | SCF2H | CH | |
| H | H | SCF2H | SCF2H | CH | |
| H | H | CH3 | OCF2H | N | |
| H | H | OCH3 | OCF2H | N | |
| H | H | CH3 | SCF2H | N | |
| H | H | OCH3 | SCF2H | N | |
| H | H | CH3 | OCF2CHFCl | N | |
| H | H | OCH3 | OCF2CHFCl | N | |
| H | H | CH3 | OCF2CHFBr | N | |
| H | H | OCH3 | OCF2CHFBr | N | |
| H | H | CH3 | OCF2CF2H | N | |
| H | H | OCH3 | OCF2CF2H | N | |
| H | H | CH3 | OCF2CHFCF3 | N | |
| H | H | OCH3 | OCF2CHFCF3 | N | |
| H | H | OCF2H | OCF2H | N | |

TABLE IIIe

[In Formula I] Q is

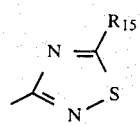

| R | R15 | X | Y | Z | m.p.(°C.) |
|---|-----|---|---|---|-----------|
| H | H | CH3 | OCH3 | N | |
| H | H | Cl | OCH3 | CH | |
| H | H | CH3 | C2H5 | CH | |
| H | H | OCH3 | CH2OCH3 | N | |
| H | H | CH3 | OC2H5 | N | |
| H | H | OCH3 | OC2H5 | CH | |
| H | H | OCH3 | CH(OCH3)2 | CH | |
| H | CH3 | CH3 | CH3 | CH | |
| H | CH3 | CH3 | OCH3 | CH | |
| H | CH3 | OCH3 | OCH3 | CH | |
| H | CH3 | CH3 | CH3 | N | |
| H | CH3 | CH3 | OCH3 | N | |
| H | CH3 | OCH3 | OCH3 | N | |
| H | C2H5 | OCH3 | OCH3 | CH | |
| H | C2H5 | OCH3 | CH3 | CH | |
| H | C2H5 | CH3 | CH3 | CH | |
| H | C2H5 | OCH3 | OCH3 | N | |
| H | C2H5 | OCH3 | CH3 | N | |
| H | CH3 | OCH3 | OCH2CF3 | CH | |
| H | CH3 | OCH3 | (ring) | CH | |
| H | H | CH3 | OCF2H | CH | |
| H | H | OCH3 | OCF2H | CH | |
| H | H | CH3 | SCF2H | CH | |
| H | H | OCH3 | SCF2H | CH | |
| H | H | CH3 | OCF2CHFCl | CH | |
| H | H | OCH3 | OCF2CHFCl | CH | |
| H | H | CH3 | OCF2CHFBr | CH | |
| H | H | OCH3 | OCF2CHFBr | CH | |
| H | H | CH3 | OCF2CF2H | CH | |
| H | H | OCH3 | OCF2CF2H | CH | |
| H | H | CH3 | OCF2CHFCF3 | CH | |
| H | H | OCH3 | OCF2CHFCF3 | CH | |
| H | H | OCF2H | OCF2H | CH | |
| H | H | OCF2H | SCF2H | CH | |
| H | H | SCF2H | SCF2H | CH | |
| H | H | CH3 | OCF2H | N | |
| H | H | OCH3 | OCF2H | N | |
| H | H | CH3 | SCF2H | N | |
| H | H | OCH3 | SCF2H | N | |
| H | H | CH3 | OCF2CHFCl | N | |
| H | H | OCH3 | OCF2CHFCl | N | |
| H | H | CH3 | OCF2CHFBr | N | |
| H | H | OCH3 | OCF2CHFBr | N | |
| H | H | CH3 | OCF2CF2H | N | |
| H | H | OCH3 | OCF2CF2H | N | |
| H | H | CH3 | OCF2CHFCF3 | N | |
| H | H | OCH3 | OCF2CHFCF3 | N | |
| H | H | OCF2H | OCF2H | N | |

TABLE IIIe

[In Formula I] Q is

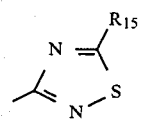

| R | R15 | X | Y | Z | m.p.(°C.) |
|---|-----|---|---|---|-----------|
| H | H | CH3 | CH3 | CH | |
| H | H | OCH3 | OCH3 | CH | |
| H | H | CH3 | OCH3 | CH | |
| H | H | CH3 | CH3 | N | |
| H | H | OCH3 | OCH3 | N | |

TABLE IIIf

[In Formula I] Q is

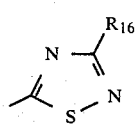

| R | R16 | X | Y | Z | m.p.(°C.) |
|---|-----|---|---|---|-----------|
| H | H | CH3 | CH3 | CH | |
| H | H | OCH3 | OCH3 | CH | |
| H | H | CH3 | OCH3 | CH | |
| H | H | CH3 | CH3 | N | |
| H | H | OCH3 | OCH3 | N | |

TABLE IIIf-continued

[In Formula I] Q is

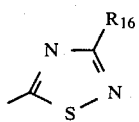

| R | R16 | X | Y | Z | m.p.(°C.) |
|---|---|---|---|---|---|
| H | H | CH3 | OCH3 | N | |
| H | H | Cl | OCH3 | CH | |
| H | H | CH3 | C2H5 | CH | |
| H | H | OCH3 | CH2OCH3 | N | |
| H | H | CH3 | OC2H5 | N | |
| H | H | OCH3 | OC2H5 | CH | |
| H | H | CH3 | CH(OCH3)2 | CH | |
| H | CH3 | CH3 | CH3 | CH | |
| H | CH3 | CH3 | OCH3 | CH | |
| H | CH3 | OCH3 | OCH3 | CH | |
| H | CH3 | CH3 | CH3 | N | |
| H | CH3 | CH3 | OCH3 | N | |
| H | CH3 | OCH3 | OCH3 | N | |
| H | C2H5 | OCH3 | OCH3 | CH | |
| H | C2H5 | OCH3 | CH3 | CH | |
| H | C2H5 | CH3 | CH3 | CH | |
| H | C2H5 | OCH3 | OCH3 | N | |
| H | C2H5 | OCH3 | CH3 | N | |
| H | H | OCH3 | OCH2CF3 | CH | |
| H | H | CH3 | OCF2H | CH | |
| H | H | OCH3 | OCF2H | CH | |
| H | H | CH3 | SCF2H | CH | |
| H | H | OCH3 | SCF2H | CH | |
| H | H | CH3 | OCF2CHFCl | CH | |
| H | H | OCH3 | OCF2CHFCl | CH | |
| H | H | CH3 | OCF2CHFBr | CH | |
| H | H | OCH3 | OCF2CHFBr | CH | |
| H | H | CH3 | OCF2CF2H | CH | |
| H | H | OCH3 | OCF2CF2H | CH | |
| H | H | CH3 | OCF2CHFCF3 | CH | |
| H | H | OCH3 | OCF2CHFCF3 | CH | |
| H | H | OCF2H | OCF2H | CH | |
| H | H | OCF2H | SCF2H | CH | |
| H | H | SCF2H | SCF2H | CH | |
| H | H | CH3 | OCF2H | N | |
| H | H | OCH3 | OCF2H | N | |
| H | H | CH3 | SCF2H | N | |
| H | H | OCH3 | SCF2H | N | |
| H | H | CH3 | OCF2CHFCl | N | |
| H | H | OCH3 | OCF2CHFCl | N | |
| H | H | CH3 | OCF2CHFBr | N | |
| H | H | OCH3 | OCF2CHFBr | N | |
| H | H | CH3 | OCF2CF2H | N | |
| H | H | OCH3 | OCF2CF2H | N | |
| H | H | CH3 | OCF2CHFCF3 | N | |
| H | H | OCH3 | OCF2CHFCF3 | N | |
| H | H | OCF2H | OCF2H | N | |

TABLE IIIg

[In Formula I] Q is

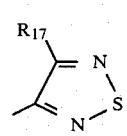

| R | R17 | X | Y | Z | m.p. (°C.) |
|---|---|---|---|---|---|
| H | H | CH3 | CH3 | CH | |
| H | H | OCH3 | OCH3 | CH | |
| H | H | CH3 | OCH3 | CH | |
| H | H | CH3 | CH3 | N | |
| H | H | OCH3 | OCH3 | N | |
| H | H | CH3 | OCH3 | N | |
| H | CH3 | CH3 | CH3 | CH | |
| H | CH3 | CH3 | OCH3 | CH | |
| H | CH3 | OCH3 | OCH3 | CH | |
| H | CH3 | CH3 | CH3 | N | |
| H | CH3 | CH3 | OCH3 | N | |

TABLE IIIg-continued

[In Formula I] Q is

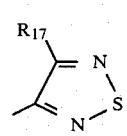

| R | R17 | X | Y | Z | m.p. (°C.) |
|---|---|---|---|---|---|
| H | CH3 | OCH3 | OCH3 | N | |
| H | H | Cl | OCH3 | CH | |
| H | H | OCH3 | OCH2CF3 | CH | |
| H | H | OCH3 | (dioxolane) | CH | |
| H | H | CH3 | OCF2H | CH | |
| H | H | OCH3 | OCF2H | CH | |
| H | H | CH3 | SCF2H | CH | |
| H | H | OCH3 | SCF2H | CH | |
| H | H | CH3 | OCF2CHFCl | CH | |
| H | H | OCH3 | OCF2CHFCl | CH | |
| H | H | CH3 | OCF2CHFBr | CH | |
| H | H | OCH3 | OCF2CHFBr | CH | |
| H | H | CH3 | OCF2CF2H | CH | |
| H | H | OCH3 | OCF2CF2H | CH | |
| H | H | CH3 | OCF2CHFCF3 | CH | |
| H | H | OCH3 | OCF2CHFCF3 | CH | |
| H | H | OCF2H | OCF2H | CH | |
| H | H | OCF2H | SCF2H | CH | |
| H | H | SCF2H | SCF2H | CH | |
| H | H | CH3 | OCF2H | N | |
| H | H | OCH3 | OCF2H | N | |
| H | H | CH3 | SCF2H | N | |
| H | H | OCH3 | SCF2H | N | |
| H | H | CH3 | OCF2CHFCl | N | |
| H | H | OCH3 | OCF2CHFCl | N | |
| H | H | CH3 | OCF2CHFBr | N | |
| H | H | OCH3 | OCF2CHFBr | N | |
| H | H | CH3 | OCF2CF2H | N | |
| H | H | OCH3 | OCF2CF2H | N | |
| H | H | CH3 | OCF2CHFCF3 | N | |
| H | H | OCH3 | OCF2CHFCF3 | N | |
| H | H | OCF2H | OCF2H | N | |

TABLE IIIh

[In Formula I] Q is

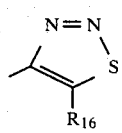

| R | R16 | X | Y | Z | m.p. (°C.) |
|---|---|---|---|---|---|
| H | H | CH3 | CH3 | CH | 156–158° |
| H | H | CH3 | OCH3 | CH | 145–147° |
| H | H | OCH3 | OCH3 | CH | 173–175° |
| H | H | CH3 | OCH3 | N | 151–155° |
| H | H | OCH3 | OCH3 | N | 155–156° |
| H | H | CH3 | CH3 | N | 157–159° |
| H | H | Cl | OCH3 | CH | 167–169° |
| H | H | CH3 | C2H5 | CH | |
| H | H | OCH3 | CH2OCH3 | N | |
| H | H | CH3 | OC2H5 | N | |
| H | H | OCH3 | OC2H5 | CH | |
| H | H | CH3 | CH(OCH3)2 | CH | |
| H | CH3 | CH3 | CH3 | CH | |
| H | CH3 | CH3 | OCH3 | CH | |
| H | CH3 | OCH3 | OCH3 | CH | |
| H | CH3 | CH3 | CH3 | N | |
| H | CH3 | CH3 | OCH3 | N | |
| H | CH3 | OCH3 | OCH3 | N | |
| H | C2H5 | CH3 | CH3 | CH | |
| H | C2H5 | CH3 | OCH3 | CH | |

TABLE IIIh-continued

[In Formula I] Q is

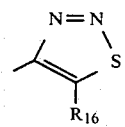

| R | R16 | X | Y | Z | m.p. (°C.) |
|---|---|---|---|---|---|
| H | C2H5 | OCH3 | OCH3 | CH | |
| H | C2H5 | CH3 | CH3 | N | |
| H | C2H5 | CH3 | OCH3 | N | |
| H | C2H5 | OCH3 | OCH3 | N | |
| 6-F | H | OCH3 | OCH3 | CH | |
| 6-Cl | H | OCH3 | OCH3 | CH | |
| 6-Br | H | OCH3 | OCH3 | CH | |
| 6-CF3 | H | OCH3 | OCH3 | CH | |
| 5-OCH3 | H | OCH3 | OCH3 | CH | |
| 5-CH3 | H | OCH3 | OCH3 | CH | |
| H | H | OCH3 | CH(OCH3)2 | CH | |
| H | H | Cl | OC2H5 | CH | |
| H | H | OCH3 | OCH2CF3 | CH | |
| H | H | CH3 | OCH2CF3 | CH | |
| H | H | CH3 | OCH2CF3 | N | |
| H | H | OCH3 | OCH2CF3 | N | |
| H | H | OCH3 | CH2OCH3 | CH | |
| H | H | CH3 | OC2H5 | CH | |
| H | H | OCH3 | C2H5 | CH | |
| H | H | OCH3 | (dioxolane) | CH | |
| H | H | CH3 | (dioxolane) | CH | |
| H | H | CH3 | OCF2H | CH | |
| H | H | OCH3 | OCF2H | CH | |
| H | H | CH3 | SCF2H | CH | |
| H | H | OCH3 | SCF2H | CH | |
| H | H | CH3 | OCF2CHFCl | CH | |
| H | H | OCH3 | OCF2CHFCl | CH | |
| H | H | CH3 | OCF2CHFBr | CH | |
| H | H | OCH3 | OCF2CHFBr | CH | |
| H | H | CH3 | OCF2CF2H | CH | |
| H | H | OCH3 | OCF2CF2H | CH | |
| H | H | CH3 | OCF2CHFCF3 | CH | |
| H | H | OCH3 | OCF2CHFCF3 | CH | |
| H | H | OCF2H | OCF2H | CH | |
| H | H | OCF2H | SCF2H | CH | |
| H | H | SCF2H | SCF2H | CH | |
| H | H | CH3 | OCF2H | N | |
| H | H | OCH3 | OCF2H | N | |
| H | H | CH3 | SCF2H | N | |
| H | H | OCH3 | SCF2H | N | |
| H | H | CH3 | OCF2CHFCl | N | |
| H | H | OCH3 | OCF2CHFCl | N | |
| H | H | CH3 | OCF2CHFBr | N | |
| H | H | OCH3 | OCF2CHFBr | N | |
| H | H | CH3 | OCF2CF2H | N | |
| H | H | OCH3 | OCF2CF2H | N | |
| H | H | CH3 | OCF2CHFCF3 | N | |
| H | H | OCH3 | OCF2CHFCF3 | N | |
| H | H | OCF2H | OCF2H | N | |

TABLE IIIi

[In Formula I] Q is

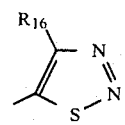

| R | R16 | X | Y | Z | m.p. (°C.) |
|---|---|---|---|---|---|
| H | H | CH3 | CH3 | CH | |
| H | H | CH3 | OCH3 | CH | |
| H | H | OCH3 | OCH3 | CH | |
| H | H | CH3 | OCH3 | N | |
| H | H | OCH3 | OCH3 | N | |
| H | H | CH3 | CH3 | N | |
| H | H | Cl | OCH3 | CH | |
| H | H | Cl | OC2H5 | CH | |
| H | CH3 | OCH3 | OCH3 | CH | |
| H | C2H5 | OCH3 | OCH3 | CH | |
| 6-F | H | OCH3 | OCH3 | CH | |
| 6-Cl | H | OCH3 | OCH3 | CH | |
| 6-Br | H | OCH3 | OCH3 | CH | |
| 5-OCH3 | H | OCH3 | OCH3 | CH | |
| 3-CH3 | H | OCH3 | OCH3 | CH | |
| H | H | OCH3 | C2H5 | CH | |
| H | H | CH3 | OC2H5 | CH | |
| H | H | OCH3 | OCH2CF3 | CH | |
| H | H | CH3 | OCH2CF3 | N | |
| H | H | OCH3 | CH2OCH3 | CH | |
| H | H | OCH3 | CH(OCH3)2 | CH | |
| H | H | OCH3 | (dioxolane) | CH | |
| H | H | CH3 | OCF2H | CH | |
| H | H | OCH3 | OCF2H | CH | |
| H | H | CH3 | SCF2H | CH | |
| H | H | OCH3 | SCF2H | CH | |
| H | H | CH3 | OCF2CHFCl | CH | |
| H | H | OCH3 | OCF2CHFCl | CH | |
| H | H | CH3 | OCF2CHFBr | CH | |
| H | H | OCH3 | OCF2CHFBr | CH | |
| H | H | CH3 | OCF2CF2H | CH | |
| H | H | OCH3 | OCF2CF2H | CH | |
| H | H | CH3 | OCF2CHFCF3 | CH | |
| H | H | OCH3 | OCF2CHFCF3 | CH | |
| H | H | OCF2H | OCF2H | CH | |
| H | H | OCF2H | SCF2H | CH | |
| H | H | SCF2H | SCF2H | CH | |
| H | H | CH3 | OCF2H | N | |
| H | H | OCH3 | OCF2H | N | |
| H | H | CH3 | SCF2H | N | |
| H | H | OCH3 | SCF2H | N | |
| H | H | CH3 | OCF2CHFCl | N | |
| H | H | OCH3 | OCF2CHFCl | N | |
| H | H | CH3 | OCF2CHFBr | N | |
| H | H | OCH3 | OCF2CHFBr | N | |
| H | H | CH3 | OCF2CF2H | N | |
| H | H | OCH3 | OCF2CF2H | N | |
| H | H | CH3 | OCF2CHFCF3 | N | |
| H | H | OCH3 | OCF2CHFCF3 | N | |
| H | H | OCF2H | OCF2H | N | |

Using analogous procedures to those described in Example 7 above, the following compounds in Tables IV–IVd can be prepared.

TABLE IV

[In Formula I] Q is

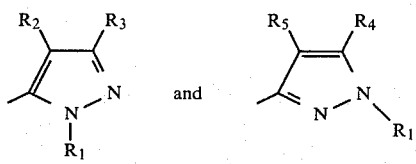
and

| R | $R_1$ | $R_2$ | $R_3$ | $R_4$ | $R_5$ | X | Y | Z | m.p. (°C.) |
|---|---|---|---|---|---|---|---|---|---|
| H | $CH_3$ | H | H | H | H | $CH_3$ | $CH_3$ | CH | |
| H | $CH_3$ | H | H | H | H | $OCH_3$ | $OCH_3$ | CH | |
| H | $CH_3$ | H | H | H | H | $CH_3$ | $OCH_3$ | CH | |
| H | $CH_3$ | H | H | H | H | $CH_3$ | $CH_3$ | N | |
| H | $CH_3$ | H | H | H | H | $OCH_3$ | $OCH_3$ | N | |
| H | $CH_3$ | H | H | H | H | $CH_3$ | $OCH_3$ | N | |
| H | $CH_3$ | H | H | H | H | Cl | $OCH_3$ | CH | |
| H | $CH_3$ | H | H | H | H | $CH_3$ | $C_2H_5$ | CH | |
| H | $CH_3$ | H | H | H | H | $OCH_3$ | $CH_2OCH_3$ | N | |
| H | $CH_3$ | H | H | H | H | $CH_3$ | $OC_2H_5$ | N | |
| H | $CH_3$ | H | H | H | H | $OCH_3$ | $OC_2H_5$ | CH | |
| H | $CH_3$ | H | H | H | H | $OCH_3$ | $CH(OCH_3)_2$ | CH | |
| H | $CH_3$ | $CH_3$ | H | H | $CH_3$ | $OCH_3$ | $OCH_3$ | CH | |
| H | $CH_3$ | $C_2H_5$ | H | H | $C_2H_5$ | $OCH_3$ | $OCH_3$ | CH | |
| H | $CH_3$ | H | $CH_3$ | $CH_3$ | H | $OCH_3$ | $OCH_3$ | CH | |
| H | $CH_3$ | H | $C_2H_5$ | $C_2H_5$ | H | $OCH_3$ | $OCH_3$ | CH | |
| 6-F | $CH_3$ | H | H | H | H | $OCH_3$ | $OCH_3$ | CH | |
| 6-Cl | $CH_3$ | H | H | H | H | $OCH_3$ | $OCH_3$ | CH | |
| 6-Br | $CH_3$ | H | H | H | H | $OCH_3$ | $OCH_3$ | CH | |
| 6-$CF_3$ | $CH_3$ | H | H | H | H | $OCH_3$ | $OCH_3$ | CH | |
| 5-$OCH_3$ | $CH_3$ | H | H | H | H | $OCH_3$ | $OCH_3$ | CH | |
| 3-$CH_3$ | $CH_3$ | H | H | H | H | $OCH_3$ | $OCH_3$ | CH | |
| H | $C_2H_5$ | H | H | H | H | $OCH_3$ | $OCH_3$ | CH | |
| H | $CH_2CH_2CH_3$ | H | H | H | H | $OCH_3$ | $OCH_3$ | CH | |
| H | $CH(CH_3)_2$ | H | H | H | H | $OCH_3$ | $OCH_3$ | CH | |
| H | $CH_3$ | H | H | H | H | $OCH_3$ | $OCH_2CF_3$ | CH | |
| H | $CH_3$ | H | H | H | H | $OCH_3$ | (dioxolane) | CH | |
| H | $CH_3$ | H | H | H | H | $CH_3$ | $OCF_2H$ | CH | |
| H | $CH_3$ | H | H | H | H | $OCH_3$ | $OCF_2H$ | CH | |
| H | $CH_3$ | H | H | H | H | $CH_3$ | $SCF_2H$ | CH | |
| H | $CH_3$ | H | H | H | H | $OCH_3$ | $SCF_2H$ | CH | |
| H | $CH_3$ | H | H | H | H | $CH_3$ | $OCF_2CHFCl$ | CH | |
| H | $CH_3$ | H | H | H | H | $OCH_3$ | $OCF_2CHFCl$ | CH | |
| H | $CH_3$ | H | H | H | H | $CH_3$ | $OCF_2CHFBr$ | CH | |
| H | $CH_3$ | H | H | H | H | $OCH_3$ | $OCF_2CHFBr$ | CH | |
| H | $CH_3$ | H | H | H | H | $CH_3$ | $OCF_2CF_2H$ | CH | |
| H | $CH_3$ | H | H | H | H | $OCH_3$ | $OCF_2CF_2H$ | CH | |
| H | $CH_3$ | H | H | H | H | $CH_3$ | $OCF_2CHFCF_3$ | CH | |
| H | $CH_3$ | H | H | H | H | $OCH_3$ | $OCF_2CHFCF_3$ | CH | |
| H | $CH_3$ | H | H | H | H | $OCF_2H$ | $OCF_2H$ | CH | |
| H | $CH_3$ | H | H | H | H | $OCF_2H$ | $SCF_2H$ | CH | |
| H | $CH_3$ | H | H | H | H | $SCF_2H$ | $SCF_2H$ | CH | |
| H | $CH_3$ | H | H | H | H | $CH_3$ | $OCF_2H$ | N | |
| H | $CH_3$ | H | H | H | H | $OCH_3$ | $OCF_2H$ | N | |
| H | $CH_3$ | H | H | H | H | $CH_3$ | $SCF_2H$ | N | |
| H | $CH_3$ | H | H | H | H | $OCH_3$ | $SCF_2H$ | N | |
| H | $CH_3$ | H | H | H | H | $CH_3$ | $OCF_2CHFCl$ | N | |
| H | $CH_3$ | H | H | H | H | $OCH_3$ | $OCF_2CHFCl$ | N | |
| H | $CH_3$ | H | H | H | H | $CH_3$ | $OCF_2CHFBr$ | N | |
| H | $CH_3$ | H | H | H | H | $OCH_3$ | $OCF_2CHFBr$ | N | |
| H | $CH_3$ | H | H | H | H | $CH_3$ | $OCF_2CF_2H$ | N | |
| H | $CH_3$ | H | H | H | H | $OCH_3$ | $OCF_2CF_2H$ | N | |
| H | $CH_3$ | H | H | H | H | $CH_3$ | $OCF_2CHFCF_3$ | N | |
| H | $CH_3$ | H | H | H | H | $OCH_3$ | $OCF_2CHFCF_3$ | N | |
| H | $CH_3$ | H | H | H | H | $OCF_2H$ | $OCF_2H$ | N | |

TABLE IVa

[In Formula I] Q is

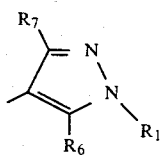

| R | R₁ | R₆ | R₇ | X | Y | Z | m.p. (°C.) |
|---|---|---|---|---|---|---|---|
| H | CH₃ | H | H | CH₃ | CH₃ | CH | |
| H | CH₃ | H | H | OCH₃ | OCH₃ | CH | |
| H | CH₃ | H | H | CH₃ | OCH₃ | CH | |
| H | CH₃ | H | H | CH₃ | CH₃ | N | |
| H | CH₃ | H | H | OCH₃ | OCH₃ | N | |
| H | CH₃ | H | H | CH₃ | OCH₃ | N | |
| H | CH₃ | H | H | Cl | OCH₃ | CH | |
| H | CH₃ | H | H | CH₃ | C₂H₅ | CH | |
| H | CH₃ | H | H | OCH₃ | CH₂OCH₃ | N | |
| H | CH₃ | H | H | CH₃ | OC₂H₅ | N | |
| H | CH₃ | H | H | OCH₃ | OC₂H₅ | CH | |
| H | CH₃ | H | H | OCH₃ | CH(OCH₃)₂ | CH | |
| H | CH₃ | CH₃ | H | OCH₃ | OCH₃ | CH | |
| H | CH₃ | H | CH₃ | OCH₃ | OCH₃ | CH | |
| H | C₂H₅ | H | H | OCH₃ | OCH₃ | CH | |
| H | CH₂CH₂CH₃ | H | H | OCH₃ | OCH₃ | CH | |
| H | CH(CH₃)₂ | H | H | OCH₃ | OCH₃ | CH | |
| H | CH₃ | H | H | OCH₃ | OCH₂CF₃ | CH | |
| H | CH₃ | H | H | OCH₃ | 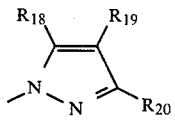 | CH | |
| H | CH₃ | H | H | CH₃ | OCF₂H | CH | |
| H | CH₃ | H | H | OCH₃ | OCF₂H | CH | |

TABLE IVa-continued

[In Formula I] Q is

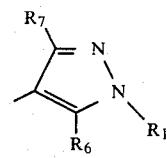

| R | R₁ | R₆ | R₇ | X | Y | Z | m.p. (°C.) |
|---|---|---|---|---|---|---|---|
| H | CH₃ | H | H | CH₃ | SCF₂H | CH | |
| H | CH₃ | H | H | OCH₃ | SCF₂H | CH | |
| H | CH₃ | H | H | CH₃ | OCF₂CHFCl | CH | |
| H | CH₃ | H | H | OCH₃ | OCF₂CHFCl | CH | |
| H | CH₃ | H | H | CH₃ | OCF₂CHFBr | CH | |
| H | CH₃ | H | H | OCH₃ | OCF₂CHFBr | CH | |
| H | CH₃ | H | H | CH₃ | OCF₂CF₂H | CH | |
| H | CH₃ | H | H | OCH₃ | OCF₂CF₂H | CH | |
| H | CH₃ | H | H | CH₃ | OCF₂CHFCF₃ | CH | |
| H | CH₃ | H | H | OCH₃ | OCF₂CHFCF₃ | CH | |
| H | CH₃ | H | H | OCF₂H | OCF₂H | CH | |
| H | CH₃ | H | H | OCF₂H | SCF₂H | CH | |
| H | CH₃ | H | H | SCF₂H | SCF₂H | CH | |
| H | CH₃ | H | H | CH₃ | OCF₂H | N | |
| H | CH₃ | H | H | OCH₃ | OCF₂H | N | |
| H | CH₃ | H | H | CH₃ | SCF₂H | N | |
| H | CH₃ | H | H | OCH₃ | SCF₂H | N | |
| H | CH₃ | H | H | CH₃ | OCF₂CHFCl | N | |
| H | CH₃ | H | H | OCH₃ | OCF₂CHFCl | N | |
| H | CH₃ | H | H | CH₃ | OCF₂CHFBr | N | |
| H | CH₃ | H | H | OCH₃ | OCF₂CHFBr | N | |
| H | CH₃ | H | H | CH₃ | OCF₂CF₂H | N | |
| H | CH₃ | H | H | OCH₃ | OCF₂CF₂H | N | |
| H | CH₃ | H | H | CH₃ | OCF₂CHFCF₃ | N | |
| H | CH₃ | H | H | OCH₃ | OCF₂CHFCF₃ | N | |
| H | CH₃ | H | H | OCF₂H | OCF₂H | N | |

TABLE IVb

[In Formula I] Q is

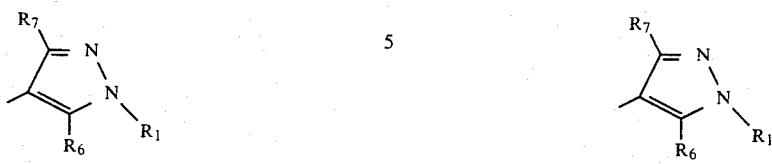

| R | R₁₈ | R₁₉ | R₂₀ | X | Y | Z | m.p. (°C.) |
|---|---|---|---|---|---|---|---|
| H | H | H | H | OCH₃ | OCH₃ | CH | |
| H | H | H | H | OCH₃ | CH₃ | CH | |
| H | H | H | H | CH₃ | CH₃ | CH | |
| H | H | H | H | OCH₃ | OCH₃ | N | |
| H | H | H | H | OCH₃ | CH₃ | N | |
| H | CH₃ | H | CH₃ | OCH₃ | OCH₃ | CH | |
| H | CH₃ | H | CH₃ | OCH₃ | CH₃ | CH | |
| H | CH₃ | H | CH₃ | CH₃ | CH₃ | CH | |
| H | CH₃ | H | CH₃ | OCH₃ | OCH₃ | N | |
| H | CH₃ | H | CH₃ | CH₃ | OCH₃ | N | |
| H | CH₃ | CH₃ | CH₃ | OCH₃ | OCH₃ | CH | |
| H | CH₃ | C₂H₅ | CH₃ | OCH₃ | OCH₃ | CH | |
| H | C₂H₅ | H | C₂H₅ | OCH₃ | OCH₃ | CH | |
| H | CH₂CH₂CH₃ | H | CH₂CH₂CH₃ | OCH₃ | OCH₃ | CH | |
| H | CH(CH₃)₂ | H | CH(CH₃)₂ | OCH₃ | OCH₃ | CH | |
| H | CH₃ | H | CH₃ | Cl | OCH₃ | CH | |
| H | CH₃ | H | CH₃ | OCH₃ | OC₂H₅ | CH | |
| H | CH₃ | H | CH₃ | CH₃ | C₂H₅ | CH | |
| H | CH₃ | H | CH₃ | OCH₃ | CH₂OCH₃ | N | |
| H | CH₃ | H | CH₃ | CH₃ | OC₂H₅ | N | |
| H | CH₃ | H | CH₃ | OCH₃ | CH(OCH₃)₂ | CH | |
| 5-F | CH₃ | H | CH₃ | OCH₃ | OCH₃ | CH | |
| 6-Cl | CH₃ | H | CH₃ | OCH₃ | OCH₃ | CH | |
| 6-Br | CH₃ | H | CH₃ | OCH₃ | OCH₃ | CH | |
| 3-CH₃ | CH₃ | H | CH₃ | OCH₃ | OCH₃ | CH | |
| 5-CF₃ | CH₃ | H | CH₃ | OCH₃ | OCH₃ | CH | |
| 5-OCH₃ | CH₃ | H | CH₃ | OCH₃ | OCH₃ | CH | |
| H | CH₃ | H | CH₃ | OCH₃ | OCH₂CF₃ | CH | |

TABLE IVb-continued

[In Formula I] Q is

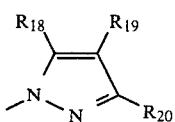

| R | R$_{18}$ | R$_{19}$ | R$_{20}$ | X | Y | Z | m.p. (°C.) |
|---|---|---|---|---|---|---|---|
| H | CH$_3$ | H | CH$_3$ | OCH$_3$ | ![](cyclic acetal) | CH | |
| H | CH$_3$ | H | H | CH$_3$ | OCF$_2$H | CH | |
| H | CH$_3$ | H | H | OCH$_3$ | OCF$_2$H | CH | |
| H | CH$_3$ | H | H | CH$_3$ | SCF$_2$H | CH | |
| H | CH$_3$ | H | H | OCH$_3$ | SCF$_2$H | CH | |
| H | CH$_3$ | H | H | CH$_3$ | OCF$_2$CHFCl | CH | |
| H | CH$_3$ | H | H | OCH$_3$ | OCF$_2$CHFCl | CH | |
| H | CH$_3$ | H | H | CH$_3$ | OCF$_2$CHFBr | CH | |
| H | CH$_3$ | H | H | OCH$_3$ | OCF$_2$CHFBr | CH | |
| H | CH$_3$ | H | H | CH$_3$ | OCF$_2$CF$_2$H | CH | |
| H | CH$_3$ | H | H | OCH$_3$ | OCF$_2$CF$_2$H | CH | |
| H | CH$_3$ | H | H | CH$_3$ | OCF$_2$CHFCF$_3$ | CH | |
| H | CH$_3$ | H | H | OCH$_3$ | OCF$_2$CHFCF$_3$ | CH | |
| H | CH$_3$ | H | H | OCF$_2$H | OCF$_2$H | CH | |
| H | CH$_3$ | H | H | OCF$_2$H | SCF$_2$H | CH | |
| H | CH$_3$ | H | H | SCF$_2$H | SCF$_2$H | CH | |
| H | CH$_3$ | H | H | CH$_3$ | OCF$_2$H | N | |
| H | CH$_3$ | H | H | OCH$_3$ | OCF$_2$H | N | |
| H | CH$_3$ | H | H | CH$_3$ | SCF$_2$H | N | |
| H | CH$_3$ | H | H | OCH$_3$ | SCF$_2$H | N | |
| H | CH$_3$ | H | H | CH$_3$ | OCF$_2$CHFCl | N | |
| H | CH$_3$ | H | H | OCH$_3$ | OCF$_2$CHFCl | N | |
| H | CH$_3$ | H | H | CH$_3$ | OCF$_2$CHFBr | N | |
| H | CH$_3$ | H | H | OCH$_3$ | OCF$_2$CHFBr | N | |
| H | CH$_3$ | H | H | CH$_3$ | OCF$_2$CF$_2$H | N | |
| H | CH$_3$ | H | H | OCH$_3$ | OCF$_2$CF$_2$H | N | |
| H | CH$_3$ | H | H | CH$_3$ | OCF$_2$CHFCF$_3$ | N | |
| H | CH$_3$ | H | H | OCH$_3$ | OCF$_2$CHFCF$_3$ | N | |
| H | CH$_3$ | H | H | OCF$_2$H | OCF$_2$H | N | |

TABLE V

[In Formula I] Q is

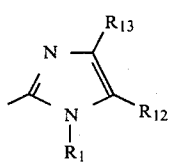

| R | R$_1$ | R$_{12}$ | R$_{13}$ | X | Y | Z | m.p. (°C.) |
|---|---|---|---|---|---|---|---|
| H | CH$_3$ | H | H | CH$_3$ | CH$_3$ | CH | |
| H | CH$_3$ | H | H | OCH$_3$ | OCH$_3$ | CH | |
| H | CH$_3$ | H | H | CH$_3$ | OCH$_3$ | CH | |
| H | CH$_3$ | H | H | CH$_3$ | CH$_3$ | N | |
| H | CH$_3$ | H | H | OCH$_3$ | OCH$_3$ | N | |
| H | CH$_3$ | H | H | CH$_3$ | OCH$_3$ | N | |
| H | CH$_3$ | H | H | Cl | OCH$_3$ | CH | |
| H | CH$_3$ | H | H | CH$_3$ | C$_2$H$_5$ | CH | |
| H | CH$_3$ | H | H | OCH$_3$ | CH$_2$OCH$_3$ | N | |
| H | CH$_3$ | H | H | CH$_3$ | OC$_2$H$_5$ | N | |
| H | CH$_3$ | H | H | OCH$_3$ | OC$_2$H$_5$ | CH | |
| H | CH$_3$ | H | H | OCH$_3$ | CH(OCH$_3$)$_2$ | CH | |
| H | CH$_3$ | CH$_3$ | H | OCH$_3$ | OCH$_3$ | CH | |
| H | CH$_3$ | C$_2$H$_5$ | H | OCH$_3$ | OCH$_3$ | CH | |
| H | CH$_3$ | H | CH$_3$ | OCH$_3$ | OCH$_3$ | CH | |
| H | CH$_3$ | H | C$_2$H$_5$ | OCH$_3$ | OCH$_3$ | CH | |
| H | C$_2$H$_5$ | H | H | OCH$_3$ | OCH$_3$ | CH | |
| H | CH$_2$CH$_2$CH$_3$ | H | H | OCH$_3$ | OCH$_3$ | CH | |
| H | CH(CH$_3$)$_2$ | H | H | OCH$_3$ | OCH$_3$ | CH | |
| 5-F | CH$_3$ | H | H | OCH$_3$ | OCH$_3$ | CH | |
| 6-Cl | CH$_3$ | H | H | OCH$_3$ | OCH$_3$ | CH | |
| 6-Br | CH$_3$ | H | H | OCH$_3$ | OCH$_3$ | CH | |
| 3-CH$_3$ | CH$_3$ | H | H | OCH$_3$ | OCH$_3$ | CH | |

TABLE V-continued

[In Formula I] Q is

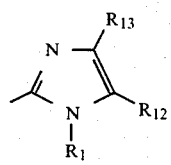

| R | R₁ | R₁₂ | R₁₃ | X | Y | Z | m.p. (°C.) |
|---|---|---|---|---|---|---|---|
| 5-OCH₃ | CH₃ | H | H | OCH₃ | OCH₃ | CH | |
| 5-CF₃ | CH₃ | H | H | OCH₃ | OCH₃ | CH | |
| H | CH₃ | H | H | OCH₃ | OCH₂CF₃ | CH | |
| H | CH₃ | H | H | OCH₃ | $\begin{smallmatrix}O\\CH\\O\end{smallmatrix}$ (1,3-dioxolane) | CH | |
| H | CH₃ | H | H | Cl | OC₂H₅ | CH | |
| H | CH₃ | H | H | CH₃ | OCF₂H | CH | |
| H | CH₃ | H | H | OCH₃ | OCF₂H | CH | |
| H | CH₃ | H | H | CH₃ | SCF₂H | CH | |
| H | CH₃ | H | H | OCH₃ | SCF₂H | CH | |
| H | CH₃ | H | H | CH₃ | OCF₂CHFCl | CH | |
| H | CH₃ | H | H | OCH₃ | OCF₂CHFCl | CH | |
| H | CH₃ | H | H | CH₃ | OCF₂CHFBr | CH | |
| H | CH₃ | H | H | OCH₃ | OCF₂CHFBr | CH | |
| H | CH₃ | H | H | CH₃ | OCF₂CF₂H | CH | |
| H | CH₃ | H | H | OCH₃ | OCF₂CF₂H | CH | |
| H | CH₃ | H | H | CH₃ | OCF₂CHFCF₃ | CH | |
| H | CH₃ | H | H | OCH₃ | OCF₂CHFCF₃ | CH | |
| H | CH₃ | H | H | OCF₂H | OCF₂H | CH | |
| H | CH₃ | H | H | OCF₂H | SCF₂H | CH | |
| H | CH₃ | H | H | SCF₂H | SCF₂H | CH | |
| H | CH₃ | H | H | CH₃ | OCF₂H | N | |
| H | CH₃ | H | H | OCH₃ | OCF₂H | N | |
| H | CH₃ | H | H | CH₃ | SCF₂H | N | |
| H | CH₃ | H | H | OCH₃ | SCF₂H | N | |
| H | CH₃ | H | H | CH₃ | OCF₂CHFCl | N | |
| H | CH₃ | H | H | OCH₃ | OCF₂CHFCl | N | |
| H | CH₃ | H | H | CH₃ | OCF₂CHFBr | N | |
| H | CH₃ | H | H | OCH₃ | OCF₂CHFBr | N | |
| H | CH₃ | H | H | CH₃ | OCF₂CF₂H | N | |
| H | CH₃ | H | H | OCH₃ | OCF₂CF₂H | N | |
| H | CH₃ | H | H | CH₃ | OCF₂CHFCF₃ | N | |
| H | CH₃ | H | H | OCH₃ | OCF₂CHFCF₃ | N | |
| H | CH₃ | H | H | OCF₂H | OCF₂H | N | |

TABLE Va

[In Formula I] Q is

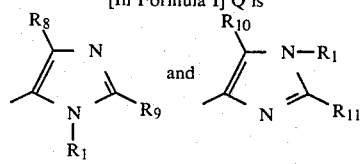

| R | R₁ | R₈ | R₉ | R₁₀ | R₁₁ | X | Y | Z | m.p. (°C.) |
|---|---|---|---|---|---|---|---|---|---|
| H | CH₃ | H | H | H | H | CH₃ | CH₃ | CH | |
| H | CH₃ | H | H | H | H | OCH₃ | OCH₃ | CH | |
| H | CH₃ | H | H | H | H | CH₃ | OCH₃ | CH | |
| H | CH₃ | H | H | H | H | CH₃ | CH₃ | N | |
| H | CH₃ | H | H | H | H | OCH₃ | OCH₃ | N | |
| H | CH₃ | H | H | H | H | CH₃ | OCH₃ | N | |
| H | CH₃ | H | H | H | H | Cl | OCH₃ | CH | |
| H | CH₃ | H | H | H | H | CH₃ | C₂H₅ | CH | |
| H | CH₃ | H | H | H | H | OCH₃ | CH₂OCH₃ | N | |
| H | CH₃ | H | H | H | H | CH₃ | OC₂H₅ | N | |
| H | CH₃ | H | H | H | H | OCH₃ | OC₂H₅ | CH | |
| H | CH₃ | H | H | H | H | OCH₃ | CH(OCH₃)₂ | CH | |
| H | CH₃ | CH₃ | H | CH₃ | H | OCH₃ | OCH₃ | CH | |
| H | CH₃ | C₂H₅ | H | C₂H₅ | H | OCH₃ | OCH₃ | CH | |
| H | CH₃ | H | CH₃ | H | CH₃ | OCH₃ | OCH₃ | CH | |
| H | CH₃ | H | C₂H₅ | H | C₂H₅ | OCH₃ | OCH₃ | CH | |
| H | C₂H₅ | H | H | H | H | OCH₃ | OCH₃ | CH | |

TABLE Va-continued

[In Formula I] Q is

![structures with R8, R9, R1, R10, R11]

and

| R | R₁ | R₈ | R₉ | R₁₀ | R₁₁ | X | Y | Z | m.p. (°C.) |
|---|---|---|---|---|---|---|---|---|---|
| H | CH₂CH₂CH₃ | H | H | H | H | OCH₃ | OCH₃ | CH | |
| H | CH(CH₃)₂ | H | H | H | H | OCH₃ | OCH₃ | CH | |
| H | CH₃ | H | H | H | H | OCH₃ | OCH₂CF₃ | CH | |
| H | CH₃ | H | H | H | H | OCH₃ | 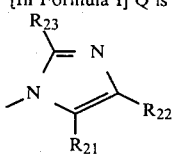 | CH | |
| H | CH₃ | H | H | H | H | CH₃ | OCF₂H | CH | |
| H | CH₃ | H | H | H | H | OCH₃ | OCF₂H | CH | |
| H | CH₃ | H | H | H | H | CH₃ | SCF₂H | CH | |
| H | CH₃ | H | H | H | H | OCH₃ | SCF₂H | CH | |
| H | CH₃ | H | H | H | H | CH₃ | OCF₂CHFCl | CH | |
| H | CH₃ | H | H | H | H | OCH₃ | OCF₂CHFCl | CH | |
| H | CH₃ | H | H | H | H | CH₃ | OCF₂CHFBr | CH | |
| H | CH₃ | H | H | H | H | OCH₃ | OCF₂CHFBr | CH | |
| H | CH₃ | H | H | H | H | CH₃ | OCF₂CF₂H | CH | |
| H | CH₃ | H | H | H | H | OCH₃ | OCF₂CF₂H | CH | |
| H | CH₃ | H | H | H | H | CH₃ | OCF₂CHFCF₃ | CH | |
| H | CH₃ | H | H | H | H | OCH₃ | OCF₂CHFCF₃ | CH | |
| H | CH₃ | H | H | H | H | OCF₂H | OCF₂H | CH | |
| H | CH₃ | H | H | H | H | OCF₂H | SCF₂H | CH | |
| H | CH₃ | H | H | H | H | SCF₂H | SCF₂H | CH | |
| H | CH₃ | H | H | H | H | CH₃ | OCF₂H | N | |
| H | CH₃ | H | H | H | H | OCH₃ | OCF₂H | N | |
| H | CH₃ | H | H | H | H | CH₃ | SCF₂H | N | |
| H | CH₃ | H | H | H | H | OCH₃ | SCF₂H | N | |
| H | CH₃ | H | H | H | H | CH₃ | OCF₂CHFCl | N | |
| H | CH₃ | H | H | H | H | OCH₃ | OCF₂CHFCl | N | |
| H | CH₃ | H | H | H | H | CH₃ | OCF₂CHFBr | N | |
| H | CH₃ | H | H | H | H | OCH₃ | OCF₂CHFBr | N | |
| H | CH₃ | H | H | H | H | CH₃ | OCF₂CF₂H | N | |
| H | CH₃ | H | H | H | H | OCH₃ | OCF₂CF₂H | N | |
| H | CH₃ | H | H | H | H | CH₃ | OCF₂CHFCF₃ | N | |
| H | CH₃ | H | H | H | H | OCH₃ | OCF₂CHFCF₃ | N | |
| H | CH₃ | H | H | H | H | OCF₂H | OCF₂H | N | |

TABLE Vb

[In Formula I] Q is structure with R₂₁, R₂₂, R₂₃

| R | R₂₁ | R₂₂ | R₂₃ | X | Y | Z | m.p. (°C.) |
|---|---|---|---|---|---|---|---|
| H | H | H | H | CH₃ | CH₃ | CH | |
| H | H | H | H | CH₃ | OCH₃ | CH | |
| H | H | H | H | OCH₃ | OCH₃ | CH | |
| H | H | H | H | CH₃ | OCH₃ | N | |
| H | H | H | H | OCH₃ | OCH₃ | N | |
| H | H | H | H | CH₃ | CH₃ | N | |
| H | H | H | CH₃ | OCH₃ | OCH₃ | CH | |
| H | H | H | C₂H₅ | OCH₃ | OCH₃ | CH | |
| H | CH₃ | H | H | OCH₃ | OCH₃ | CH | |
| H | C₂H₅ | H | H | OCH₃ | OCH₃ | CH | |
| H | H | CH₃ | H | OCH₃ | OCH₃ | CH | |
| H | H | C₂H₅ | H | OCH₃ | OCH₃ | CH | |
| H | CH₃ | CH₃ | H | OCH₃ | OCH₃ | CH | |
| 5-F | H | H | H | OCH₃ | OCH₃ | CH | |
| 6-Cl | H | H | H | OCH₃ | OCH₃ | CH | |
| 6-Br | H | H | H | OCH₃ | OCH₃ | CH | |
| 3-CH₃ | H | H | H | OCH₃ | OCH₃ | CH | |
| 5-OCH₃ | H | H | H | OCH₃ | OCH₃ | CH | |
| 5-CF₃ | H | H | H | OCH₃ | OCH₃ | CH | |

TABLE Vb-continued

[In Formula I] Q is

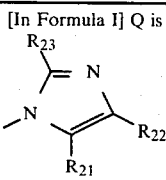

| R | R21 | R22 | R23 | X | Y | Z | m.p. (°C.) |
|---|---|---|---|---|---|---|---|
| H | H | H | H | Cl | OCH3 | CH | |
| H | H | H | H | CH3 | C2H5 | CH | |
| H | H | H | H | OCH3 | CH2OCH3 | N | |
| H | H | H | H | CH3 | OC2H5 | N | |
| H | H | H | H | OCH3 | OC2H5 | CH | |
| H | H | H | H | CH3 | CH(OCH3)2 | CH | |
| H | H | H | H | CH3 | OCF2H | CH | |
| H | H | H | H | OCH3 | OCF2H | CH | |
| H | H | H | H | CH3 | SCF2H | CH | |
| H | H | H | H | OCH3 | SCF2H | CH | |
| H | H | H | H | CH3 | OCF2CHFCl | CH | |
| H | H | H | H | OCH3 | OCF2CHFCl | CH | |
| H | H | H | H | CH3 | OCF2CHFBr | CH | |
| H | H | H | H | OCH3 | OCF2CHFBr | CH | |
| H | H | H | H | CH3 | OCF2CF2H | CH | |
| H | H | H | H | OCH3 | OCF2CF2H | CH | |
| H | H | H | H | CH3 | OCF2CHFCF3 | CH | |
| H | H | H | H | OCH3 | OCF2CHFCF3 | CH | |
| H | H | H | H | OCF2H | OCF2H | CH | |
| H | H | H | H | OCF2H | SCF2H | CH | |
| H | H | H | H | SCF2H | SCF2H | CH | |
| H | H | H | H | CH3 | OCF2H | N | |
| H | H | H | H | OCH3 | OCF2H | N | |
| H | H | H | H | CH3 | SCF2H | N | |
| H | H | H | H | OCH3 | SCF2H | N | |
| H | H | H | H | CH3 | OCF2CHFCl | N | |
| H | H | H | H | OCH3 | OCF2CHFCl | N | |
| H | H | H | H | CH3 | OCF2CHFBr | N | |
| H | H | H | H | OCH3 | OCF2CHFBr | N | |
| H | H | H | H | CH3 | OCF2CF2H | N | |
| H | H | H | H | OCH3 | OCF2CF2H | N | |
| H | H | H | H | CH3 | OCF2CHFCF3 | N | |
| H | H | H | H | OCH3 | OCF2CHFCF3 | N | |
| H | H | H | H | OCF2H | OCF2H | N | |

TABLE VI

[In Formula I] Q is

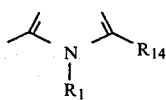

| R | R1 | R14 | X | Y | Z | m.p. (°C.) |
|---|---|---|---|---|---|---|
| H | CH3 | CH3 | OCH3 | OCH3 | CH | |
| H | CH3 | CH3 | OCH3 | CH3 | CH | |
| H | CH3 | CH3 | CH3 | CH3 | CH | |
| H | CH3 | CH3 | OCH3 | OCH3 | N | |
| H | CH3 | CH3 | OCH3 | CH3 | N | |
| H | CH3 | C2H5 | OCH3 | OCH3 | CH | |
| H | CH3 | C2H5 | OCH3 | CH3 | CH | |
| H | CH3 | C2H5 | CH3 | CH3 | CH | |
| H | CH3 | C2H5 | OCH3 | OCH3 | N | |
| H | CH3 | C2H5 | CH3 | OCH3 | N | |
| H | CH3 | H | OCH3 | OCH3 | CH | |
| H | CH3 | H | CH3 | OCH3 | CH | |
| H | CH3 | H | CH3 | CH3 | CH | |
| H | CH3 | H | OCH3 | OCH3 | N | |
| H | CH3 | H | OCH3 | CH3 | N | |
| H | C2H5 | CH3 | OCH3 | OCH3 | CH | |
| H | CH2CH2CH3 | CH3 | OCH3 | OCH3 | CH | |
| H | CH(CH3)2 | CH3 | OCH3 | OCH3 | CH | |
| H | CH3 | CH3 | Cl | OCH3 | CH | |
| H | CH3 | CH3 | CH3 | OCF2H | CH | |
| H | CH3 | CH3 | OCH3 | OCF2H | CH | |
| H | CH3 | CH3 | CH3 | SCF2H | CH | |
| H | CH3 | CH3 | OCH3 | SCF2H | CH | |

TABLE VI-continued

[In Formula I] Q is

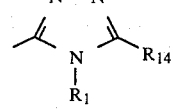

| R | R1 | R14 | X | Y | Z | m.p. (°C.) |
|---|---|---|---|---|---|---|
| H | CH3 | CH3 | CH3 | OCF2CHFCl | CH | |
| H | CH3 | CH3 | OCH3 | OCF2CHFCl | CH | |
| H | CH3 | CH3 | CH3 | OCF2CHFBr | CH | |
| H | CH3 | CH3 | OCH3 | OCF2CHFBr | CH | |
| H | CH3 | CH3 | CH3 | OCF2CF2H | CH | |
| H | CH3 | CH3 | OCH3 | OCF2CF2H | CH | |
| H | CH3 | CH3 | CH3 | OCF2CHFCF3 | CH | |
| H | CH3 | CH3 | OCH3 | OCF2CHFCF3 | CH | |
| H | CH3 | CH3 | OCF2H | OCF2H | CH | |
| H | CH3 | CH3 | OCF2H | SCF2H | CH | |
| H | CH3 | CH3 | SCF2H | SCF2H | CH | |
| H | CH3 | CH3 | CH3 | OCF2H | N | |
| H | CH3 | CH3 | OCH3 | OCF2H | N | |
| H | CH3 | CH3 | CH3 | SCF2H | N | |
| H | Ch3 | CH3 | OCH3 | SCF2H | N | |
| H | CH3 | CH3 | CH3 | OCF2CHFCl | N | |
| H | CH3 | CH3 | OCH3 | OCF2CHFCl | N | |
| H | CH3 | CH3 | CH3 | OCF2CHFBr | N | |
| H | CH3 | CH3 | OCH3 | OCF2CHFBr | N | |
| H | CH3 | CH3 | CH3 | OCF2CF2H | N | |
| H | CH3 | CH3 | OCH3 | OCF2CF2H | N | |
| H | CH3 | CH3 | CH3 | OCF2CHFCF3 | N | |
| H | CH3 | CH3 | OCH3 | OCF2CHFCF3 | N | |

TABLE VI-continued

[In Formula I] Q is

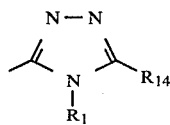

| R | R₁ | R₁₄ | X | Y | Z | m.p. (°C.) |
|---|---|---|---|---|---|---|
| H | CH₃ | CH₃ | OCF₂H | OCF₂H | N | |

TABLE VIa

[In Formula I] Q is

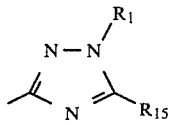

| R | R₁ | R₁₅ | X | Y | Z | m.p. (°C.) |
|---|---|---|---|---|---|---|
| H | CH₃ | CH₃ | OCH₃ | OCH₃ | CH | |
| H | CH₃ | CH₃ | OCH₃ | CH₃ | CH | |
| H | CH₃ | CH₃ | CH₃ | CH₃ | CH | |
| H | CH₃ | CH₃ | OCH₃ | OCH₃ | N | |
| H | CH₃ | CH₃ | OCH₃ | CH₃ | N | |
| H | CH₃ | C₂H₅ | OCH₃ | OCH₃ | CH | |
| H | CH₃ | C₂H₅ | CH₃ | OCH₃ | CH | |
| H | CH₃ | C₂H₅ | CH₃ | CH₃ | CH | |
| H | CH₃ | C₂H₅ | OCH₃ | OCH₃ | N | |
| H | CH₃ | C₂H₅ | CH₃ | OCH₃ | N | |
| H | CH₃ | H | OCH₃ | OCH₃ | CH | |
| H | CH₃ | H | OCH₃ | CH₃ | CH | |
| H | CH₃ | H | CH₃ | CH₃ | CH | |
| H | CH₃ | H | OCH₃ | OCH₃ | N | |
| H | CH₃ | H | CH₃ | OCH₃ | N | |
| H | C₂H₅ | CH₃ | OCH₃ | OCH₃ | CH | |
| H | CH₂CH₂CH₃ | CH₃ | OCH₃ | OCH₃ | CH | |
| H | CH(CH₃)₂ | CH₃ | OCH₃ | OCH₃ | CH | |
| H | CH₃ | CH₃ | Cl | OCH₃ | CH | |
| H | CH₃ | CH₃ | CH₃ | OCF₂H | CH | |
| H | CH₃ | CH₃ | OCH₃ | OCF₂H | CH | |
| H | CH₃ | CH₃ | CH₃ | SCF₂H | CH | |
| H | CH₃ | CH₃ | OCH₃ | SCF₂H | CH | |
| H | CH₃ | CH₃ | CH₃ | OCF₂CHFCl | CH | |
| H | CH₃ | CH₃ | OCH₃ | OCF₂CHFCl | CH | |
| H | CH₃ | CH₃ | CH₃ | OCF₂CHFBr | CH | |
| H | CH₃ | CH₃ | OCH₃ | OCF₂CHFBr | CH | |
| H | CH₃ | CH₃ | CH₃ | OCF₂CF₂H | CH | |
| H | CH₃ | CH₃ | OCH₃ | OCF₂CF₂H | CH | |
| H | CH₃ | CH₃ | CH₃ | OCF₂CHFCF₃ | CH | |
| H | CH₃ | CH₃ | OCH₃ | OCF₂CHFCF₃ | CH | |
| H | CH₃ | CH₃ | OCF₂H | OCF₂H | CH | |
| H | CH₃ | CH₃ | OCF₂H | SCF₂H | CH | |
| H | CH₃ | CH₃ | SCF₂H | SCF₂H | CH | |
| H | CH₃ | CH₃ | CH₃ | OCF₂H | N | |
| H | CH₃ | CH₃ | OCH₃ | OCF₂H | N | |
| H | CH₃ | CH₃ | CH₃ | SCF₂H | N | |
| H | CH₃ | CH₃ | OCH₃ | SCF₂H | N | |
| H | CH₃ | CH₃ | CH₃ | OCF₂CHFCl | N | |
| H | CH₃ | CH₃ | OCH₃ | OCF₂CHFCl | N | |
| H | CH₃ | CH₃ | CH₃ | OCF₂CHFBr | N | |
| H | CH₃ | CH₃ | OCH₃ | OCF₂CHFBr | N | |
| H | CH₃ | CH₃ | CH₃ | OCF₂CF₂H | N | |
| H | CH₃ | CH₃ | OCH₃ | OCF₂CF₂H | N | |
| H | CH₃ | CH₃ | CH₃ | OCF₂CHFCF₃ | N | |
| H | CH₃ | CH₃ | OCH₃ | OCF₂CHFCF₃ | N | |
| H | CH₃ | CH₃ | OCF₂H | OCF₂H | N | |

TABLE VIb

[In Formula I] Q is

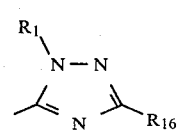

| R | R₁ | R₁₆ | X | Y | Z | m.p. (°C.) |
|---|---|---|---|---|---|---|
| H | CH₃ | CH₃ | OCH₃ | OCH₃ | CH | |
| H | CH₃ | CH₃ | OCH₃ | CH₃ | CH | |
| H | CH₃ | CH₃ | CH₃ | CH₃ | CH | |
| H | CH₃ | CH₃ | CH₃ | CH₃ | N | |
| H | CH₃ | CH₃ | OCH₃ | OCH₃ | N | |
| H | CH₃ | CH₃ | OCH₃ | CH₃ | N | |
| H | CH₃ | C₂H₅ | OCH₃ | OCH₃ | CH | |
| H | CH₃ | C₂H₅ | CH₃ | OCH₃ | CH | |
| H | CH₃ | C₂H₅ | CH₃ | CH₃ | CH | |
| H | CH₃ | C₂H₅ | OCH₃ | OCH₃ | N | |
| H | CH₃ | C₂H₅ | CH₃ | OCH₃ | N | |
| H | CH₃ | H | OCH₃ | OCH₃ | CH | |
| H | CH₃ | H | OCH₃ | CH₃ | CH | |
| H | CH₃ | H | CH₃ | CH₃ | CH | |
| H | CH₃ | H | OCH₃ | OCH₃ | N | |
| H | CH₃ | H | CH₃ | OCH₃ | N | |
| H | C₂H₅ | CH₃ | OCH₃ | OCH₃ | CH | |
| H | CH₂CH₂CH₃ | CH₃ | OCH₃ | OCH₃ | CH | |
| H | CH(CH₃)₂ | CH₃ | OCH₃ | OCH₃ | CH | |
| H | CH₃ | CH₃ | Cl | OCH₃ | CH | |
| H | CH₃ | CH₃ | CH₃ | OCF₂H | CH | |
| H | CH₃ | CH₃ | OCH₃ | OCF₂H | CH | |
| H | CH₃ | CH₃ | CH₃ | SCF₂H | CH | |
| H | CH₃ | CH₃ | OCH₃ | SCF₂H | CH | |
| H | CH₃ | CH₃ | CH₃ | OCF₂CHFCl | CH | |
| H | CH₃ | CH₃ | OCH₃ | OCF₂CHFCl | CH | |
| H | CH₃ | CH₃ | CH₃ | OCF₂CHFBr | CH | |
| H | CH₃ | CH₃ | OCH₃ | OCF₂CHFBr | CH | |
| H | CH₃ | CH₃ | CH₃ | OCF₂CF₂H | CH | |
| H | CH₃ | CH₃ | OCH₃ | OCF₂CF₂H | CH | |
| H | CH₃ | CH₃ | CH₃ | OCF₂CHFCF₃ | CH | |
| H | CH₃ | CH₃ | OCH₃ | OCF₂CHFCF₃ | CH | |
| H | CH₃ | CH₃ | OCF₂H | OCF₂H | CH | |
| H | CH₃ | CH₃ | OCF₂H | SCF₂H | CH | |
| H | CH₃ | CH₃ | SCF₂H | SCF₂H | CH | |
| H | CH₃ | CH₃ | CH₃ | OCF₂H | N | |
| H | CH₃ | CH₃ | OCH₃ | OCF₂H | N | |
| H | CH₃ | CH₃ | CH₃ | SCF₂H | N | |
| H | CH₃ | CH₃ | OCH₃ | SCF₂H | N | |
| H | CH₃ | CH₃ | CH₃ | OCF₂CHFCl | N | |
| H | CH₃ | CH₃ | OCH₃ | OCF₂CHFCl | N | |
| H | CH₃ | CH₃ | CH₃ | OCF₂CHFBr | N | |
| H | CH₃ | CH₃ | OCH₃ | OCF₂CHFBr | N | |
| H | CH₃ | CH₃ | CH₃ | OCF₂CF₂H | N | |
| H | CH₃ | CH₃ | OCH₃ | OCF₂CF₂H | N | |
| H | CH₃ | CH₃ | CH₃ | OCF₂CHFCF₃ | N | |
| H | CH₃ | CH₃ | OCH₃ | OCF₂CHFCF₃ | N | |
| H | CH₃ | CH₃ | OCF₂H | OCF₂H | N | |

TABLE VIc

[In Formula I] Q is

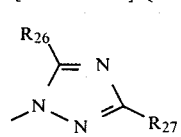

| R | R₂₆ | R₂₇ | X | Y | Z | m.p. (°C.) |
|---|---|---|---|---|---|---|
| H | H | H | CH₃ | CH₃ | CH | |
| H | H | H | OCH₃ | OCH₃ | CH | |
| H | H | H | CH₃ | OCH₃ | CH | |
| H | H | H | CH₃ | CH₃ | N | |
| H | H | H | OCH₃ | OCH₃ | N | |
| H | H | H | CH₃ | OCH₃ | N | |
| H | H | H | Cl | OCH₃ | CH | |
| H | H | H | CH₃ | C₂H₅ | CH | |

TABLE VIc-continued

[In Formula I] Q is

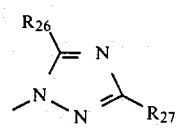

| R | $R_{26}$ | $R_{27}$ | X | Y | Z | m.p. (°C.) |
|---|---|---|---|---|---|---|
| H | H | H | $OCH_3$ | $CH_2OCH_3$ | N | |
| H | H | H | $CH_3$ | $OC_2H_5$ | N | |
| H | H | H | $OCH_3$ | $OC_2H_5$ | CH | |
| H | H | H | $CH_3$ | $CH(OCH_3)_2$ | CH | |
| 5-F | H | H | $OCH_3$ | $OCH_3$ | CH | |
| 6-Cl | H | H | $OCH_3$ | $OCH_3$ | CH | |
| 6-Br | H | H | $OCH_3$ | $OCH_3$ | CH | |
| 3-$CH_3$ | H | H | $OCH_3$ | $OCH_3$ | CH | |
| 5-$OCH_3$ | H | H | $OCH_3$ | $OCH_3$ | CH | |
| 5-$CF_3$ | H | H | $OCH_3$ | $OCH_3$ | CH | |
| H | $CH_3$ | H | $OCH_3$ | $OCH_3$ | CH | |
| H | H | $CH_3$ | $OCH_3$ | $OCH_3$ | CH | |
| H | H | $C_2H_5$ | $OCH_3$ | $OCH_3$ | CH | |
| H | H | H | $OCH_3$ | $OCH_2CF_3$ | CH | |
| H | H | H | $OCH_3$ | (dioxolane) | CH | |
| H | H | H | Cl | $OC_2H_5$ | CH | |
| H | H | H | $CH_3$ | $OCF_2H$ | CH | |
| H | H | H | $OCH_3$ | $OCF_2H$ | CH | |
| H | H | H | $CH_3$ | $SCF_2H$ | CH | |
| H | H | H | $OCH_3$ | $SCF_2H$ | CH | |
| H | H | H | $CH_3$ | $OCF_2CHFCl$ | CH | |
| H | H | H | $OCH_3$ | $OCF_2CHFCl$ | CH | |
| H | H | H | $CH_3$ | $OCF_2CHFBr$ | CH | |
| H | H | H | $OCH_3$ | $OCF_2CHFBr$ | CH | |
| H | H | H | $CH_3$ | $OCF_2CF_2H$ | CH | |
| H | H | H | $OCH_3$ | $OCF_2CF_2H$ | CH | |
| H | H | H | $CH_3$ | $OCF_2CHFCF_3$ | CH | |
| H | H | H | $OCH_3$ | $OCF_2CHFCF_3$ | CH | |
| H | H | H | $OCF_2H$ | $OCF_2H$ | CH | |
| H | H | H | $OCF_2H$ | $SCF_2H$ | CH | |
| H | H | H | $SCF_2H$ | $SCF_2H$ | CH | |
| H | H | H | $CH_3$ | $OCF_2H$ | N | |
| H | H | H | $OCH_3$ | $OCF_2H$ | N | |
| H | H | H | $CH_3$ | $SCF_2H$ | N | |
| H | H | H | $OCH_3$ | $SCF_2H$ | N | |
| H | H | H | $CH_3$ | $OCF_2CHFCl$ | N | |
| H | H | H | $OCH_3$ | $OCF_2CHFCl$ | N | |
| H | H | H | $CH_3$ | $OCF_2CHFBr$ | N | |
| H | H | H | $OCH_3$ | $OCF_2CHFBr$ | N | |
| H | H | H | $CH_3$ | $OCF_2CF_2H$ | N | |
| H | H | H | $OCH_3$ | $OCF_2CF_2H$ | N | |
| H | H | H | $CH_3$ | $OCF_2CHFCF_3$ | N | |
| H | H | H | $OCH_3$ | $OCF_2CHFCF_3$ | N | |
| H | H | H | $OCF_2H$ | $OCF_2H$ | N | |

TABLE VId

[In Formula I] Q is

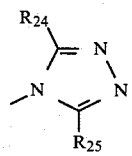

| R | $R_{24}$ | $R_{25}$ | X | Y | Z | m.p. (°C.) |
|---|---|---|---|---|---|---|
| H | H | H | $CH_3$ | $CH_3$ | CH | |
| H | H | H | $OCH_3$ | $OCH_3$ | CH | |
| H | H | H | $OCH_3$ | $CH_3$ | CH | |
| H | H | H | $OCH_3$ | $OCH_3$ | N | |
| H | H | H | $CH_3$ | $CH_3$ | N | |

TABLE VId-continued

[In Formula I] Q is

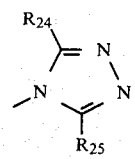

| R | $R_{24}$ | $R_{25}$ | X | Y | Z | m.p. (°C.) |
|---|---|---|---|---|---|---|
| H | $CH_3$ | H | $OCH_3$ | $OCH_3$ | CH |  |
| H | $CH_3$ | H | $OCH_3$ | $CH_3$ | CH |  |
| H | $CH_3$ | H | $CH_3$ | $CH_3$ | CH |  |
| H | $CH_3$ | H | $CH_3$ | $OCH_3$ | N |  |
| H | $CH_3$ | H | $OCH_3$ | $OCH_3$ | N |  |
| H | $CH_3$ | $CH_3$ | $OCH_3$ | $OCH_3$ | CH |  |
| H | $CH_3$ | $CH_3$ | $OCH_3$ | $CH_3$ | CH |  |
| H | $CH_3$ | $CH_3$ | $CH_3$ | $CH_3$ | CH |  |
| H | $CH_3$ | $CH_3$ | $OCH_3$ | $OCH_3$ | N |  |
| H | $CH_3$ | $CH_3$ | $CH_3$ | $CH_3$ | N |  |
| H | $CH_3$ | $C_2H_5$ | $OCH_3$ | $OCH_3$ | CH |  |
| H | $CH_3$ | $CH_3$ | Cl | $OCH_3$ | CH |  |
| H | $CH_3$ | $CH_3$ | $CH_3$ | $C_2H_5$ | CH |  |
| H | $CH_3$ | $CH_3$ | $OCH_3$ | $CH_2OCH_3$ | N |  |
| H | $CH_3$ | $CH_3$ | $CH_3$ | $OC_2H_5$ | N |  |
| H | $CH_3$ | $CH_3$ | $OCH_3$ | $OC_2H_5$ | CH |  |
| H | $CH_3$ | $CH_3$ | $CH_3$ | $CH(OCH_3)_2$ | CH |  |
| H | $CH_3$ | $CH_3$ | $CH_3$ | $OCF_2H$ | CH |  |
| H | $CH_3$ | $CH_3$ | $OCH_3$ | $OCF_2H$ | CH |  |
| H | $CH_3$ | $CH_3$ | $CH_3$ | $SCF_2H$ | CH |  |
| H | $CH_3$ | $CH_3$ | $OCH_3$ | $SCF_2H$ | CH |  |
| H | $CH_3$ | $CH_3$ | $CH_3$ | $OCF_2CHFCl$ | CH |  |
| H | $CH_3$ | $CH_3$ | $OCH_3$ | $OCF_2CHFCl$ | CH |  |
| H | $CH_3$ | $CH_3$ | $CH_3$ | $OCF_2CHFBr$ | CH |  |
| H | $CH_3$ | $CH_3$ | $OCH_3$ | $OCF_2CHFBr$ | CH |  |
| H | $CH_3$ | $CH_3$ | $CH_3$ | $OCF_2CF_2H$ | CH |  |
| H | $CH_3$ | $CH_3$ | $OCH_3$ | $OCF_2CF_2H$ | CH |  |
| H | $CH_3$ | $CH_3$ | $CH_3$ | $OCF_2CHFCF_3$ | CH |  |
| H | $CH_3$ | $CH_3$ | $OCH_3$ | $OCF_2CHFCF_3$ | CH |  |
| H | $CH_3$ | $CH_3$ | $OCF_2H$ | $OCF_2H$ | CH |  |
| H | $CH_3$ | $CH_3$ | $OCF_2H$ | $SCF_2H$ | CH |  |
| H | $CH_3$ | $CH_3$ | $SCF_2H$ | $SCF_2H$ | CH |  |
| H | $CH_3$ | $CH_3$ | $CH_3$ | $OCF_2H$ | N |  |
| H | $CH_3$ | $CH_3$ | $OCH_3$ | $OCF_2H$ | N |  |
| H | $CH_3$ | $CH_3$ | $CH_3$ | $SCF_2H$ | N |  |
| H | $CH_3$ | $CH_3$ | $OCH_3$ | $SCF_2H$ | N |  |
| H | $CH_3$ | $CH_3$ | $CH_3$ | $OCF_2CHFCl$ | N |  |
| H | $CH_3$ | $CH_3$ | $OCH_3$ | $OCF_2CHFCl$ | N |  |
| H | $CH_3$ | $CH_3$ | $CH_3$ | $OCF_2CHFBr$ | N |  |
| H | $CH_3$ | $CH_3$ | $OCH_3$ | $OCF_2CHFBr$ | N |  |
| H | $CH_3$ | $CH_3$ | $CH_3$ | $OCF_2CF_2H$ | N |  |
| H | $CH_3$ | $CH_3$ | $OCH_3$ | $OCF_2CF_2H$ | N |  |
| H | $CH_3$ | $CH_3$ | $CH_3$ | $OCF_2CHFCF_3$ | N |  |
| H | $CH_3$ | $CH_3$ | $OCH_3$ | $OCF_2CHFCF_3$ | N |  |
| H | $CH_3$ | $CH_3$ | $OCF_2H$ | $OCF_2H$ | N |  |

Using analogous procedures to those described in Examples 1, 3 and 5 above, the following compounds in Table VII can be prepared.

TABLE VII

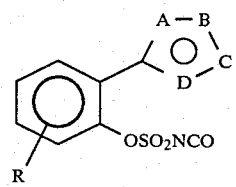

| R | A | B | C | D | Physical Property |
|---|---|---|---|---|---|
| H | N | N | CH | O | 2220 cm$^{-1}$ |
| H | N | N | C—$CH_3$ | O | 2220 cm$^{-1}$ |
| H | N | N | C—$C_2H_5$ | O | 2220 cm$^{-1}$ |
| H | N | CH | O | N | |
| H | N | C—$CH_3$ | O | N | |
| H | N | C—$C_2H_5$ | O | N | |

TABLE VII-continued

[Structure: benzene ring with substituent R, and group -A=B-O-C=D attached, plus -OSO₂NCO]

| R | A | B | C | D | Physical Property |
|---|---|---|---|---|---|
| H | N | CH | N | O | |
| H | N | C—CH₃ | N | O | |
| H | N | C—C₂H₅ | N | O | |
| H | CH | N | O | N | |
| H | C—CH₃ | N | O | N | |
| H | N | N | S | CH | 2220 cm⁻¹ |
| H | N | N | S | C—CH₃ | |
| H | N | N | S | C—C₂H₅ | |
| H | N | N | CH | S | |
| H | N | N | C—CH₃ | S | |
| H | N | N | C—C₂H₅ | S | |
| H | N | CH | S | N | |
| H | N | CH | N | S | |
| H | CH | N | S | N | |
| H | C—CH₃ | N | S | N | |
| H | CH | CH | N | O | 2220 cm⁻¹ |
| H | C—CH₃ | CH | N | O | |
| H | CH | C—CH₃ | N | O | |
| H | CH | CH | O | N | 2220 cm⁻¹ |
| H | C—CH₃ | CH | O | N | |
| H | CH | C—CH₃ | O | N | |
| H | CH | N | O | CH | |
| H | C—CH₃ | N | O | C—CH₃ | |
| H | CH | CH | N | S | |
| H | CH | CH | S | N | |
| H | CH | S | N | CH | |
| H | N | CH | CH | O | |
| H | CH | N | CH | O | |
| H | CH | O | CH | N | |
| H | N | CH | CH | S | |
| H | CH | S | C—CH₃ | N | |
| H | CH | S | C—C₂H₅ | N | |
| H | C—CH₃ | N | C—CH₃ | S | |
| 6-CH₃ | N | N | CH | O | 2220 cm⁻¹ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VIII

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 8

| Wettable Powder | |
|---|---|
| 2-(5-isoxazolyl)phenyl N—[(4,6-dimethoxypyrimidin-2-yl)aminocarbonyl]sulfamate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 9

| Wettable Powder | |
|---|---|
| 2-(1,3,4-oxadiazol-2-yl)-6-methylphenyl N—[(4-methoxy-6-methylpyrimidin-2-yl)aminocarbonyl]sulfamate | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 10

| Granule | |
|---|---|
| Wettable Powder of Example 9 | 5% |
| attapulgite granules (U.S.S. 20-40 mesh; 0.84-0.42 mm) | 95% |

A slurry of wettable powder containing ≈25% solids is sprayed on the surface of attapulgite granules in a double-cone blender. The granules are dried and packaged.

EXAMPLE 11

| Extruded Pellet | |
|---|---|
| 2-(3-isoxazolyl)phenyl N—[(4-methoxy-6-methyl-1,3,5-triazin-2-yl)aminocarbonyl]sulfamate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 12

| Oil Suspension | |
|---|---|
| 2-(5-isoxazolyl)phenyl N—[(4,6-dimethylpyrimidin-2-yl)aminocarbonyl]sulfamate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 13

| Wettable Powder | |
|---|---|
| 2-(1,3,4-oxadiazol-2-yl)phenyl N—[(4-methoxy-6-methylpyrimidin-2-yl)aminocarbonyl]sulfamate | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 14

| Low Strength Granule | |
|---|---|
| 2-(5-isoxazolyl)phenyl N—[(4-methoxy-6-methylpyrimidin-2-yl aminocarbonyl]sulfamate | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 15

| Aqueous Suspension | |
|---|---|
| 2-(5-methyl-1,3,4-oxadiazol-2-yl)phenyl N—[(4,6-dimethoxypyrimidin-2-yl)aminocarbonyl]sulfamate | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 16

| Solution | |
|---|---|
| 2-(3-isoxazolyl)phenyl N—[(4-methoxy-6-methyl-1,3,5-triazin-2-yl)aminocarbonyl]sulfamate, sodium salt | 5% |
| water | 95% |

The salt is added directly to the water with stirring to produce the solution, which may then be packaged for use.

EXAMPLE 17

| Low Strength Granule | |
|---|---|
| 2-(3-isoxazolyl)phenyl N—[(4,6-dimethylpyrimidin-2-yl)aminocarbonyl]sulfamate | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 18

| Granule | |
|---|---|
| 2-(3-isoxazolyl)phenyl N—[(4,6-dimethoxypyrimidin-2-yl)aminocarbonyl]sulfamate | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 19

| High Strength Concentrate | |
|---|---|
| 2-(1,3,4-oxadiazol-2-yl)phenyl N—[(-methoxy-6-1,3,5-triazin-2-yl)aminocarbonyl]sulfamate | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 20

| Wettable Powder | |
|---|---|
| 2-(1,3,4-oxadiazol-2-yl))phenyl N—[(4,6-dimethyl-pyrimidin-2-yl)aminocarbonyl]sulfamate | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 21

| Wettable Powder | |
|---|---|
| 2-(1,3,4-oxadiazol-2-yl)phenyl N—[(4,6-dimethoxy-pyrimidin-2-yl)aminocarbonyl]sulfamate | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 22

| Oil Suspension | |
|---|---|
| 2-(3-isoxazolyl)phenyl N—[(4-methoxy-6-methylpyrimidin-2-yl)aminocarbonyl]sulfamate | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

The compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- or post-emergence weed control in crops, such as wheat, corn, rice and cotton.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria sp.), barnyardgrass (Echinochloa crusgalli), wild oats (Avena fatua), sicklepod (Cassia obtusifolia), morningglory (Ipomoea sp.), cocklebur (Xanthium sp.), sorghum, corn, soybean, rice, wheat and nutsedge tubers (Cyperus rotundus) were planted in a growth medium and treated pre-emergence with the chemicals dissolved in a non-phytotoxic solvent. At the same time, cotton having five leaves (including cotyledonary ones), bush beans with the third trifoliolate leaf expanding, crabgrass, barnyardgrass and wild oats with two leaves, sicklepod with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed. Sometimes the testing technique is modified by omitting the bush bean from the post-emergence phase, and adding cotton to the pre-emergence plantings. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings:

C=chlorosis or necrosis;
E=emergence inhibition;
G=growth retardation;
H=formative effects;
P=terminal bud injury;
U=unusual pigmentation; and
6Y=abscised buds or flowers.

The ratings for the compounds tested by this procedure are presented in Table A. It will be seen that the compounds have high pre- and post-emergence herbicidal activity.

Although some of the compounds do not exhibit a high degree of activity at the rates tested, it is expected that these compounds will exhibit herbicidal effects at higher rates.

Compounds

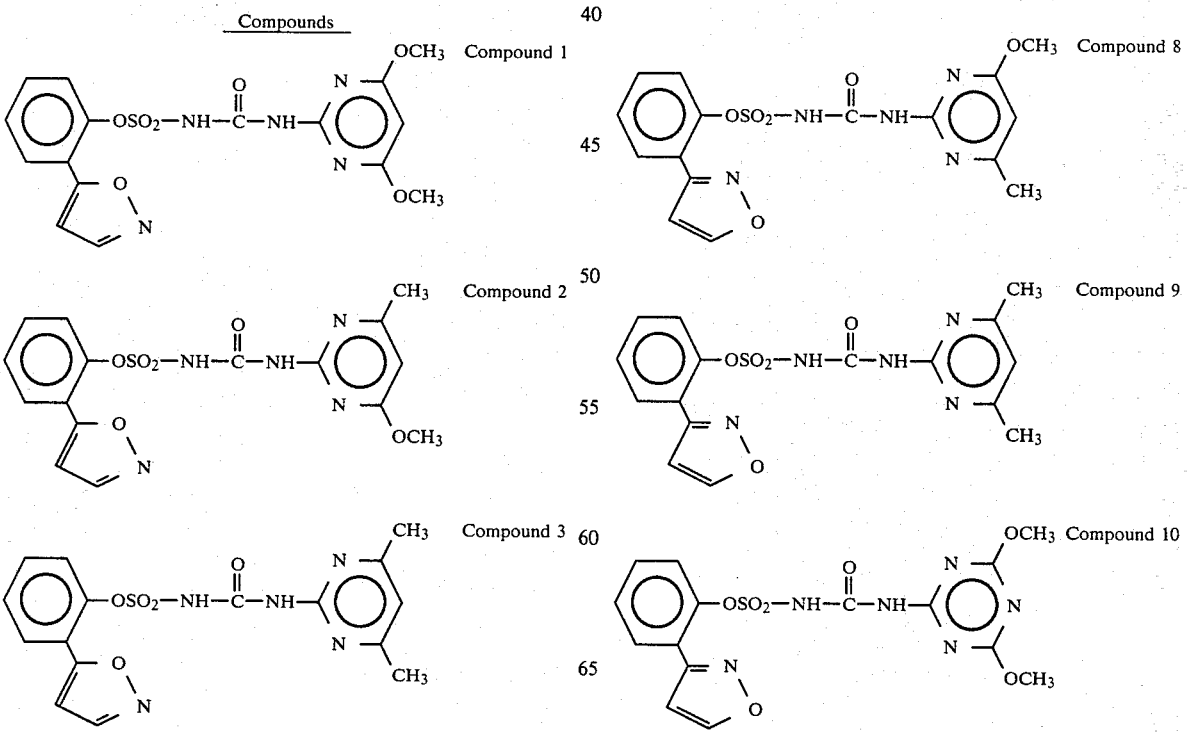

-continued
Compounds
Compound 11
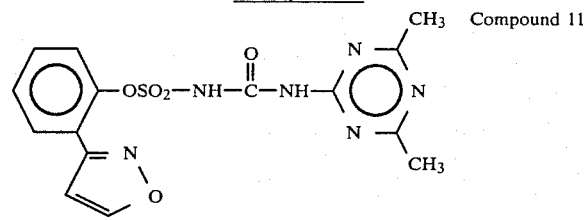
Compound 12
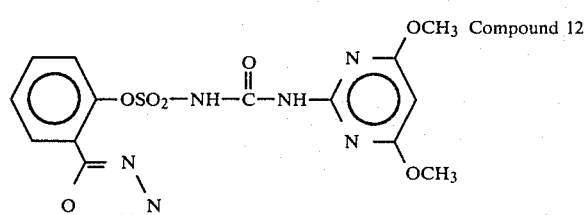
Compound 13
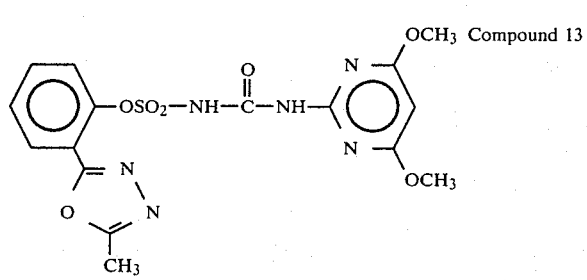
Compound 14
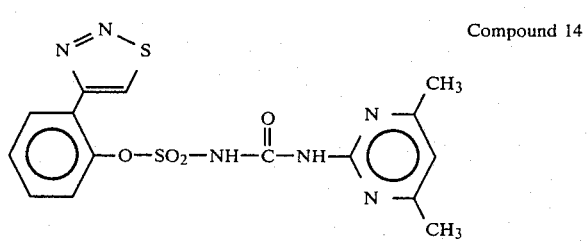
Compound 15
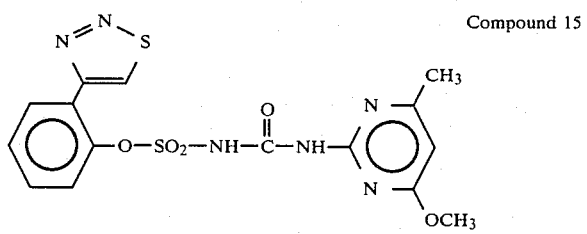
Compound 16
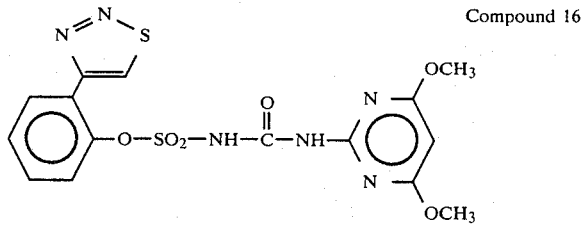
Compound 17
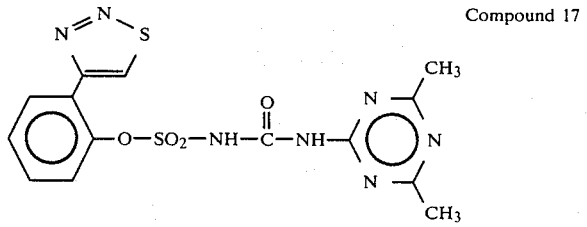
-continued
Compounds
Compound 18
Compound 19
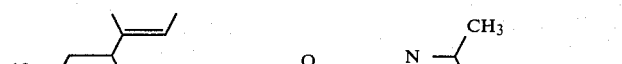
Compound 20
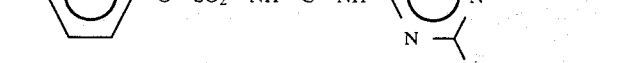
Compound 21
Compound 22
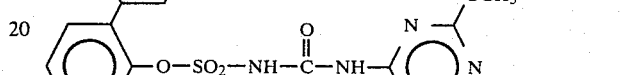
Compound 23

-continued
Compounds

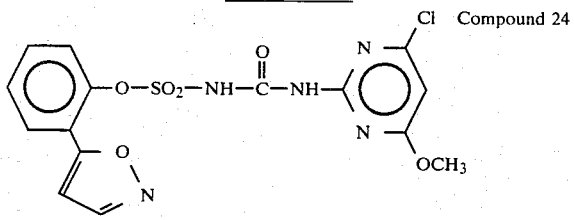
Compound 24

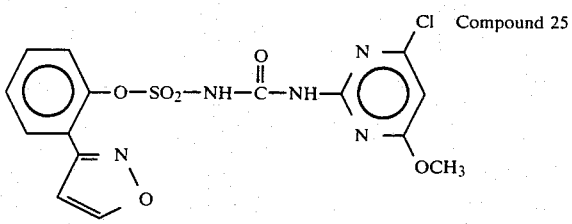
Compound 25

-continued
Compounds

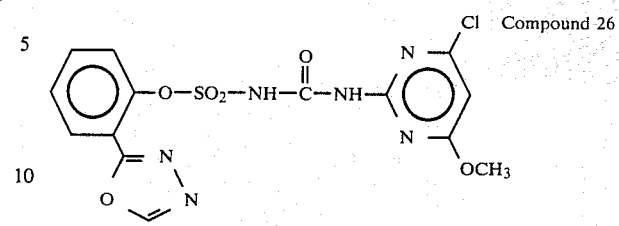
Compound 26

TABLE A

| Rate kg/ha | Cmpd. 1<br>0.4 | Cmpd. 2<br>0.4 | Cmpd. 3<br>0.4 | Cmpd. 4<br>0.4 | Cmpd. 5<br>0.4 | Cmpd. 6<br>0.4 | Cmpd. 7<br>.05 | Cmpd. 8<br>.05 | Cmpd. 9<br>.05 | Cmpd. 10<br>.05 |
|---|---|---|---|---|---|---|---|---|---|---|
| POST-EMERGENCE | | | | | | | | | | |
| Bush bean | 7G | 9G | 4G | 0 | 3H | 0 | 5C,8H,6Y | 6C,9G,6Y | 1C,3H | 1C,1H |
| Cotton | 2C | 6G | 1H | 0 | 1C | 0 | 1C | 1C,4G | 0 | 1H |
| Morningglory | 10C | 9G | 9G | 2C | 9G | 1C | 2C,6H | 5C,9G | 2C | 1C |
| Cocklebur | 9C | 9C | 9C | 1C | 9H | 0 | 10C | 9C | 2C,9H | 1H |
| Sicklepod | 3H | 5G | 2C | 1C | 1C | 0 | 1C,3G | 2C | 2C | 0 |
| Nutsedge | 9C | 9G | 2G | 0 | 0 | 0 | 4C,9G | 2C,8G | 0 | 0 |
| Crabgrass | 0 | 0 | 0 | 0 | 2G | 0 | 2G | 4G | 0 | 0 |
| Barnyardgrass | 7H | 7H | 1H | 1H | 5H | 0 | 1C,4H | 2C,6H | 0 | 0 |
| Wild Oats | 0 | 3G | 0 | 0 | 0 | 0 | 0 | 0 | 0 | 0 |
| Wheat | 0 | 0 | 0 | 0 | 0 | 0 | 0 | 0 | 0 | 0 |
| Corn | 3G | 3H | 0 | 0 | 5G | 0 | 1G | 2C,5H | 2G | 0 |
| Soybean | 9C | 9H | 8H | 2H,1C | 8G | 1H | 5C,9G | 5C,9G | 1C,2H | 1H |
| Rice | 2G | 4G | 2G | 1C,4G | 7G | 0 | 0 | 0 | 0 | 0 |
| Sorghum | 5G | 9H | 9H | 2C,8H | 9G | 2G | 2G | 4C,8H | 2C,4H | 2C,4H |
| Sugarbeet | | | | | | | 5C,9G | 5C,9H | 3C,6G | 2C,6G |

| Rate kg/ha | Cmpd. 11<br>.05 | Cmpd. 12<br>.05 | Cmpd. 13<br>.05 | Cmpd. 14<br>0.05 | Cmpd. 15<br>0.05 | Compound 16<br>0.05 | Cmpd. 17<br>0.4 | Cmpd. 18<br>0.05 | Cmpd. 19<br>0.05 |
|---|---|---|---|---|---|---|---|---|---|
| POST-EMERGENCE | | | | | | | | | |
| Bush bean | 0 | 9C | 3C,5G,6Y | 0 | 2C,3G | 2C,5H,6Y | 4C,9G,6Y | 0 | 1C | 0 |
| Cotton | 0 | 9G | 3C,4H | 2C,3G | 2C,3H | 2C | 4C,9G | 0 | 2C | 2C |
| Morningglory | 0 | 9G | 5C,9G | 3C,6G | 5C,9G | 2C,8G | 4C,9G | 0 | 3C,5H | 3C,8G |
| Cocklebur | 0 | 9H | 4C,9G | 2C,8G | 5C,9G | 9C | 9C | 0 | 2C,4H | 1H |
| Sicklepod | 0 | 6H | 2C | 2C | 0 | 1C | 3C,6G | 0 | 1C | 4G |
| Nutsedge | 0 | 9G | 5C,9G | 0 | 2C,9G | 6C,9G | 10C | 0 | 0 | 0 |
| Crabgrass | 0 | 3G | 1C,3G | 0 | 0 | 0 | 5C | 0 | 1C,4G | 2G |
| Barnyardgrass | 0 | 7H | 1C,3H | 0 | 0 | 0 | 5H | 0 | 0 | 0 |
| Wild Oats | 0 | 0 | 0 | 0 | 0 | 0 | 0 | 0 | 0 | 0 |
| Wheat | 0 | 0 | 0 | 0 | 0 | 0 | 0 | 0 | 0 | 0 |
| Corn | 2C,4G | 0 | 0 | 0 | 0 | 0 | 1C | 0 | 0 | 0 |
| Soybean | 2G | 9C | 4C,8G | 0 | 0 | 2C,9G,5X | 5C,9G | 0 | 1C,1H | 1H |
| Rice | 0 | 0 | 0 | 0 | 0 | 0 | 4G | 0 | 0 | 2C |
| Sorghum | 0 | 9H | 3C,9H | 0 | 0 | 2G | 1C,6G | 0 | 2C,6H | 1C |
| Sugarbeet | 1C,3G | | 5C,9H | 2C,5G | 5C,8G | 4C,9G | 9C | 0 | 2C,6G | 1C,3H |

| | Cmpd. 20 | Compound 21 | Cmpd. 22 | Cmpd. 23 | Cmpd. 24 | Cmpd. 25 | Cmpd. 26 |
|---|---|---|---|---|---|---|---|
| Rate kg/ha | 0.05 | 0.05 | 0.4 | 0.05 | 0.05 | 0.05 | 0.05 |
| POST-EMERGENCE | | | | | | | |
| Bush bean | 6C,9G,6Y | 0 | 2C,3H | 1H | — | — | — | — |
| Cotton | 4C,9G | 0 | 3C,7G | 0 | 0 | 3G | 6G | 0 |
| Morningglory | 9C | 1B | 5C,9G | 2C,5H | 1C,3H | 2C,6H | 3C,8H | 0 |
| Cocklebur | 5C,9G | 0 | 5C,9G | 4C,8H | 1C,2G | 1C,3H | 3C,8H | 0 |
| Sicklepod | 4C,9G | 0 | 3C | 2C | 0 | 0 | 0 | 0 |
| Nutsedge | 4C,9G | 0 | 1C,5G | 0 | 0 | 3G | 0 | 0 |
| Crabgrass | 1C,3G | 0 | 0 | 0 | 0 | 0 | 0 | 0 |
| Barnyardgrass | 2C,9H | 0 | 1H | 2C,5H | 0 | 0 | 0 | 0 |
| Wild Oats | 0 | 0 | 0 | 0 | 0 | 0 | 0 | 0 |
| Wheat | 0 | 0 | 0 | 0 | 0 | 0 | 0 | 0 |
| Corn | 4G | 0 | 0 | 2C,8H | 1C | 1C | 0 | 0 |
| Soybean | 5C,9G | 0 | 2C,9G | 2C,2H | 0 | 0 | 2H | 0 |
| Rice | 3G | 0 | 0 | 0 | 0 | 0 | 2C,4G | 0 |
| Sorghum | 2C,8H | 0 | 2C,6H | 2C,9H | 1C | 0 | 2G | 0 |

TABLE A-continued

|  | | | | | Sugarbeet | 10C | 0 | 5C,9G | 2C,5G | 0 | 2C,8H | 2C,7G | 0 |

| Rate kg/ha | Cmpd. 1<br>0.4 | Cmpd. 2<br>0.4 | Cmpd. 3<br>0.4 | Cmpd. 4<br>0.4 | Cmpd. 5<br>0.4 | Cmpd. 6<br>0.4 | Cmpd. 7<br>.05 | Cmpd. 8<br>.05 | Cmpd. 9<br>.05 | Cmpd. 10<br>.05 |
|---|---|---|---|---|---|---|---|---|---|---|
| | | | | | PRE-EMERGENCE | | | | | |
| Morningglory | 10C | 10C | 5G | 8H | 9G | 0 | 5C,9G | 10C | 0 | 0 |
| Cocklebur | 9H | 9H | 9H | 8H | 8H | 4G | 9H | — | 8H | 2H |
| Sicklepod | 7G | 7G | 0 | 0 | 1C | 1H | 3C,7G | 2C,9G | 0 | 1C |
| Nutsedge | 10E | 9G | 0 | 0 | 4G | 0 | 10E | 0 | 2C,5G | 0 |
| Crabgrass | 0 | 1H | 0 | 1C | 0 | 1H | 4G | 2G | 1C,3G | 0 |
| Barnyardgrass | 9H | 9H | 2G | 2C,9H | 9H | 0 | 5C,9H | 3C,8H | 5C,9H | 0 |
| Wild Oats | 3G | 5G | 0 | 1C,8G | 5G | 0 | 0 | 2C | 4C,9H | 0 |
| Wheat | 3G | 5G | 0 | 3C,9G | 6G | 0 | 0 | 2C | 2C,8G | 0 |
| Corn | 8G | 8G | 6G | 9H | 9G | 2G | 2C,7G | 8H | 2C,7H | 2C,7H |
| Soybean | 8H | 8H | 2H | 0 | 1C | 0 | 3C,9H | 3C,7H | 2C,2H | 0 |
| Rice | 5G | 8H | 5G | 9H | 9H | 0 | 1C | 1C,3G | 2C,5G | 4G |
| Sorghum | 8H | 9H | 9H | 3C,9H | 9H | 4G | 5G | 2C,9H | 5C,9H | 2C,6G |
| Sugarbeet | | | | | | | 9G | 2C,9G | 9G | 0 |
| Cotton | | | | | | | | | | |

| Rate kg/ha | Cmpd. 11<br>.05 | Cmpd. 12<br>.05 | Cmpd. 13<br>.05 | Cmpd. 14<br>0.05 | Cmpd. 15<br>0.05 | Compound 16<br>0.05 0.4 | Cmpd. 17<br>0.05 | Cmpd. 18<br>0.05 | Cmpd. 19<br>0.05 |
|---|---|---|---|---|---|---|---|---|---|
| | | | | | PRE-EMERGENCE | | | | |
| Morningglory | 0 | 9G | 9G | 0 | 9G | 9G | 10C | 0 | 1C,1H | 0 |
| Cocklebur | 0 | 8H | 8H | 0 | 8H | — | 9H | 0 | 0 | 4G |
| Sicklepod | 1H | 8G | 2C | 0 | 0 | 4G | 8H | 0 | 0 | 0 |
| Nutsedge | 0 | 10E | 2C,5G | 0 | 0 | 5G | 10E | 0 | 0 | 0 |
| Crabgrass | 0 | 2C | 2C | 0 | 0 | 0 | 1C,3G | 0 | 0 | O |
| Barnyardgrass | 0 | 9H | 1C,4H | 0 | 0 | 2C | 2C,6H | 0 | 0 | 0 |
| Wild Oats | 0 | 2C | 0 | 0 | 0 | 0 | 2C | 0 | 0 | 0 |
| Wheat | 0 | 0 | 0 | 0 | 0 | 0 | 1C | 0 | 0 | 0 |
| Corn | 0 | 9G | 2C,5H | 0 | 1C | 3G | 1C,7G | 0 | 2C,5G | 0 |
| Soybean | 0 | 8H | 2C,5H | 0 | 0 | 3H | 7H | 0 | 0 | 0 |
| Rice | 0 | 6G | 2G | 0 | 0 | 0 | 4G | 0 | 1C | 3G |
| Sorghum | 0 | 9H | 2G,9H | 2C | 1C,5G | 4G | 2H,6G | 0 | 2C,8H | 2C,7H |
| Sugarbeet | 0 | | 5C,9G | 0 | 3C,9G | 4C,9G | 5C,9G | 0 | 0 | 0 |
| Cotton | | | | | | | | | | |

| Rate kg/ha | Cmpd. 20<br>0.05 | Compound 21<br>0.05 0.4 | Cmpd. 22<br>0.05 | Cmpd. 23<br>0.05 | Cmpd. 24<br>0.05 | Cmpd. 25<br>0.05 | Cmpd. 26<br>0.05 |
|---|---|---|---|---|---|---|---|
| | | PRE-EMERGENCE | | | | | |
| Morningglory | 3C,9H | 2C | 9G | 0 | 1C | 3H | 2C,5H | 2G |
| Cocklebur | — | 0 | 8G | 0 | 0 | 2C,5H | 8H | 0 |
| Sicklepod | 4C,9G | 0 | 2G | 0 | 0 | 1H | 2H | 0 |
| Nutsedge | 10E | 0 | 3G | 0 | 0 | 0 | 0 | 0 |
| Crabgrass | 1C,3G | 0 | 0 | 0 | 0 | 0 | 0 | 0 |
| Barnyardgrass | 3C,8H | 0 | 3C | 1C,5G | 0 | 0 | 0 | 0 |
| Wild Oats | 2C,2G | 0 | 0 | 0 | 0 | 0 | 0 | 0 |
| Wheat | 2C,5G | 0 | 0 | 0 | 0 | 0 | 0 | 0 |
| Corn | 9G | 0 | 2C,7G | 2C,7H | 0 | 0 | 2C,3H | 0 |
| Soybean | 9H | 0 | 0 | 1C,1H | 0 | 0 | 0 | 0 |
| Rice | 3C,7G | 0 | 1C,3G | 2G | 0 | 0 | 0 | 0 |
| Sorghum | 3C,9H | 0 | 2C,9H | 5C,9H | 0 | 5G | 5G | 0 |
| Sugarbeet | 9C | 2C,5G | 10E | 7G | 3G | 3C,9G | 2C,8G | 2H |
| Cotton | | | | 0 | 2G | 0 | 2G |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

TABLE B

PRE-EMERGENCE ON FALLSINGTON SANDY LOAM

| | Compound 1 | | Compound 2 | |
|---|---|---|---|---|
| Rate kg/ha | 0.25 | 0.06 | 0.25 | 0.06 |
| Rice | 2G | 0 | 3G | 0 |
| Barnyardgrass | 0 | 0 | 4G | 0 |
| Wheat | 3G | 3G | 0 | 0 |
| Wild Oats | 0 | 0 | 3G | 0 |
| Crabgrass | 0 | 0 | 0 | 0 |

TABLE B-continued

| | | | | |
|---|---|---|---|---|
| Sorghum | 0 | 0 | 5G | 0 |
| Johnsongrass | 3G,2U | 2U | 4G | 0 |
| Dallasgrass | 0 | 0 | 0 | 0 |
| Giant foxtail | 3G | 0 | 0 | 0 |
| Ky. bluegrass | 0 | 0 | 0 | 0 |
| Cheatgrass | 0 | 0 | 3G | 0 |
| Corn | 0 | 0 | 4G | 0 |
| Mustard | 10C | 7G,3C | 9G | 5G |
| Cocklebur | 2G | — | 0 | 0 |
| Pigweed | 5G | 0 | 7G | 0 |
| Nutsedge | 3G | 0 | 0 | 0 |
| Cotton | 0 | 0 | 0 | 0 |
| Morningglory | 2G | 0 | 0 | 0 |
| Sicklepod | 2G | 0 | 0 | 0 |
| Teaweed | 3G | 0 | 3G | 0 |
| Velvetleaf | 3G | 3G | 0 | 0 |
| Jimsonweed | 6G,4C | 3G,2C | 7G | 3G |
| Soybean | 0 | 0 | 2G | 0 |
| Sugarbeet | 10C | 5G | 6G | 0 |

PRE-EMERGENCE ON FALLSINGTON SILT LOAM

| | Compound 4 | | Compound 5 | | Compound 12 | |
|---|---|---|---|---|---|---|
| Rate kg/ha | .060 | .250 | .060 | .250 | .030 | .120 |
| Crabgrass | 0 | 0 | 0 | 0 | 0 | 2G |
| Barnyardgrass | 0 | 0 | 0 | 3H | 2G | 3G |
| Sorghum | 0 | 5G | 0 | 8G,5H | 2G | 8G,5H |
| Wild Oats | 0 | 0 | 0 | 0 | 0 | 0 |
| Johnsongrass | 0 | 3G | 0 | 5G,3H | 0 | 2G |
| Dallisgrass | 0 | 0 | 0 | 0 | 0 | 0 |
| Giant Foxtail | 0 | 0 | 0 | 0 | 0 | 2G |
| Ky. bluegrass | 0 | 0 | 0 | 0 | 0 | 0 |
| Cheatgrass | 0 | 0 | 0 | 0 | 0 | 5G |
| Sugarbeets | 0 | 0 | 0 | 0 | 3G | 8G |
| Corn | 0 | 0 | 0 | 0 | 0 | 2G |
| Mustard | 0 | 0 | 0 | 5G,3H | 8G | 9G |
| Cocklebur | 0 | 0 | 0 | 0 | 0 | 6G |
| Pigweed | 0 | 0 | 0 | 4G | — | — |
| Nutsedge | 0 | 0 | 0 | 0 | 2G | 5G |
| Cotton | 0 | 0 | 0 | 0 | 0 | 0 |
| Morningglory | 0 | 0 | 0 | 0 | 0 | 2G |
| Sicklepod | 0 | 0 | 0 | 0 | 0 | 3G |
| Teaweed | 0 | 0 | 0 | 0 | 0 | 5G |
| Velvetleaf | 0 | 0 | 0 | 0 | — | — |
| Jimsonweed | 0 | 0 | 0 | 0 | 0 | 5G |
| Soybean | 0 | 0 | 0 | 0 | 0 | 2G |
| Rice | 0 | 0 | 0 | 3G | 3G | 4G |
| Wheat | 0 | 0 | 0 | 0 | 0 | 0 |

Test C

Twenty-five cm diameter plastic pots filled with Fallsington silt loam were planted with soybeans, cotton, alfalfa, corn, rice, wheat, sunflower, sugarbeet, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (*Digitaria* sp.), nutsedge (*Cyperus rotundus*), barnyardgrass (*Echinochloa crusgalli*), johnsongrass (*Sorghum halepense*), bindweed (*Convolvulus* sp.), giant foxtail (*Setaria faberii*) and wild oats (*Avena fatua*). Approximately 2½ weeks after planting, the young plants and the soil around them were sprayed overall with the test chemicals dissolved in a non-phytotoxic solvent. Fourteen days after treatment, all species were compared to untreated controls and visually rated for response to treatment. The rating system was as described previously for Test A. The data are presented in Table C. Several of the compounds tested by this procedure are highly active herbicides, useful for the post-emergence control of weeds in crops such as corn, cotton, wheat and rice.

TABLE C

Over-the-Top Soil/Foliage Treatment

| | Compound 1 | | | | | Compound 2 | | Compound 3 | | Compound 5 | | Compound 12 | | |
|---|---|---|---|---|---|---|---|---|---|---|---|---|---|---|
| Rate, kg/ha | 0.12 | 0.03 | 0.015 | 0.008 | 0.004 | 0.25 | 0.06 | 0.25 | 0.06 | 0.25 | 0.06 | 0.06 | 0.015 | 0.008 |
| Soybeans | 10G | 9G | 9G | 9G | 9G | 10G | 9G | 5G | 0 | 4G | 2G | 10C | 4C,9G | 10C |
| Corn | — | 0 | 0 | 0 | 0 | 2G | 0 | 0 | 0 | 1G | 0 | 0 | 0 | 0 |
| Cotton | 2C | — | 2G | 1G | 0 | 1G | 0 | 0 | 0 | 0 | 0 | 10C | 4C,9G | 5C,9G |
| Rice | — | 0 | 0 | 0 | 0 | 0 | 0 | 0 | 0 | 0 | 0 | 2C | 2C | 0 |
| Wheat | — | 0 | 0 | 0 | 0 | 0 | 0 | 0 | 0 | 0 | 0 | 0 | 0 | 0 |
| Sunflower | 10C | 10C | 9G | 10P | 10P | 10C | 10C | 10C | 10P | 9G | 7G | 10C | 10C | 10C |
| Velvetleaf | 9G | 9G | 8G | 9G | 6G | 9G | 8G | 0 | 0 | 0 | 0 | 8C,9G | 10C | 2G,3C |
| Sesbania | 10C | — | 10C | 9G | 7G | 10C | 9G | 7G | 0 | 2G | 1G | 10C | 10C | 10C |
| Sicklepod | — | — | 3G | 2G | 1C | 0 | 3G | 0 | 0 | 0 | 0 | 6C,8G | 10G | 4G |
| Morningglory | 9G | — | 9G | 8G | 5G | 10C | 4G | 2G | 0 | 0 | 0 | 10C | 10C | 10C |
| Alfalfa | 7G | — | 2G | 5G | 1C | 5G | 5G | 9G | 8G | 9G | 7G | 10C | 10C | 8C,8G |
| Jimsonweed | 9G | — | 9G | 7G | 5G | 3G | 3G | 0 | 0 | 9G | 6G | 8C,9G | 4C,9G | 6C,8G |
| Cocklebur | 10G | — | 5G | 5G | 3G | 10C | 8G | — | 6G | 5G | 0 | 9G | 2H,7G | 2G |
| Mustard | — | 10C | 9G | 10C | 8G | 10C | 10C | 10C | 9G | 9G | 9G | 10C | 10C | 10C |
| Crabgrass | — | 0 | 0 | 0 | 0 | 0 | 0 | 0 | 0 | 0 | 0 | 0 | 5G | 0 |
| Barnyardgrass | — | 2G | 0 | 0 | 0 | 0 | 0 | 0 | 0 | 5G | 0 | 8G | 6G | 3G |
| Giant Foxtail | 0 | 0 | 0 | 0 | 0 | 9G | 0 | 0 | 0 | 0 | 0 | 2C,4G | 0 | 0 |
| Wild Oats | 0 | 0 | 0 | 0 | 0 | 0 | 0 | 0 | 0 | 0 | 0 | 0 | 0 | 0 |
| Sorghum | 3G | 3G | 0 | 0 | 2G | 6G | 4G | 6G | 0 | 6G | 3G | 2C,7G | 6G | 0 |
| Nutsedge | — | 8C | 8G | 8G | 0 | 3G | 0 | 0 | 0 | 0 | 0 | 8G | 2C,6G | 8G |
| Johnsongrass | — | — | 0 | 0 | 0 | 5G | 2G | 0 | 0 | 5G | 0 | 6G | 3G | 3G |
| Bindweed | 5G | 2C | 3G | 2C | 0 | 9G | 6G | 0 | 0 | 2C | 0 | 10C | 8C,9G | 5C,9G |
| Sugarbeet | — | 9G | 7G | 6G | 5G | 8G | 6G | 6G | 3G | 9G | 8G | 9C,9G | 8C,9G | 8C,9G |

Test D

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyran repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), smartweed (*Polygonum pensylvanicum*), tumble mustard (*Sisymbrium altissium*) kochia (*Kochia scoparia*), shepherd's purse (*Capsella bursa-pastoris*), *Matricaria inodora*, black nightshade (*Solanum nigrum*), yellow rocket (*Barbarea vulgaris*), wild mustard (*Brassica kaber*) and wild buckwheat (*Po-

*lygonum convolulus*). The above two pans were treated pre-emergence. At the same time two pans in which the above plant species were growing were treated post-emergence. Plant height at the time of treatment ranged from 1–15 cm depending on plant species.

The compound applied was diluted with a non-phytotoxic solvent and sprayed over-the-top of the pans. An untreated control and a solvent alone control were included for comparison. All treatments were maintained in the greenhouse for 19–21 days at which time the treatments were compared to the controls and the effects visually rated. The recorded data are presented in Table D. It will be seen that the compound tested has utility for pre- and/or post-emergence weed control in cereal crops such as wheat and barley.

TABLE D

| | Compound 1 | | | |
|---|---|---|---|---|
| | Pre-Emergence | | Post-Emergence | |
| Rate kg/ha | 0.015 | 0.06 | 0.015 | 0.06 |
| wheat | 0 | 0 | 0 | 0 |
| barley | 0 | 0 | 0 | 0 |
| wild oats | 0 | 0 | 0 | 0 |
| downy brome | 3G | 2G | — | 0 |
| cheatgrass | 2G | 2G | 0 | 0 |
| blackgrass | 0 | 2G | — | 0 |
| annual bluegrass | 1C,4G | 1C,4G | 3G | 2G |
| green foxtail | 1C,4G | 4G | 3G | 2C,2G |
| quackgrass | 0 | 0 | 0 | 0 |
| Italian ryegrass | 0 | 0 | 0 | 0 |
| ripgut brome | 0 | 0 | 0 | 0 |
| Russian thistle | — | 0 | 5G | 0 |
| tansy mustard | — | 10E | 9C,9G | 5C,9G |
| Galium aparine | — | 9G | 2C,7G | 10C |
| tumble mustard | — | 10C | 10C | 10C |
| kochia | — | 3G | 4G | 7G |
| shepherd's purse | — | 10C | 1C,8G | 3C,9G |
| *Matricaria inodora* | — | 9G | 2G | 3G |
| black nightshade | — | 0 | 0 | 3G |
| yellow rocket | — | 9G | 8G | 2C,9G |
| rapeseed | — | 2C,9G | 5C,9G | 8C,9G |
| wild buckwheat | — | 10C | 0 | 3C,9G |

What is claimed is:

1. A compound of the formula:

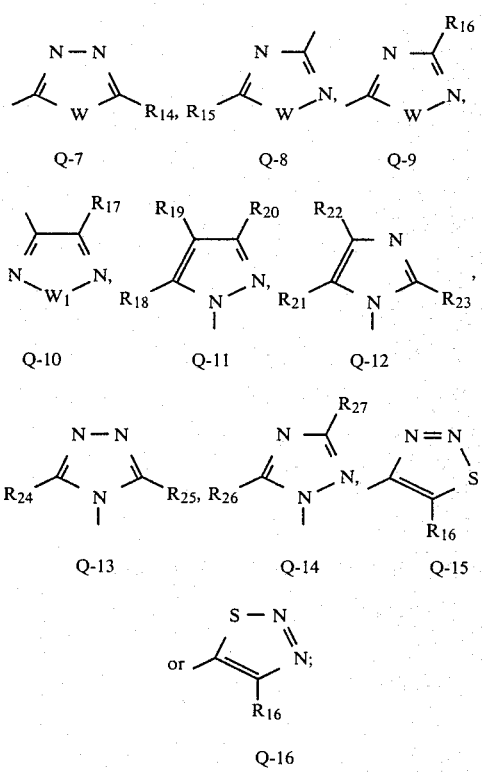

where

Q is

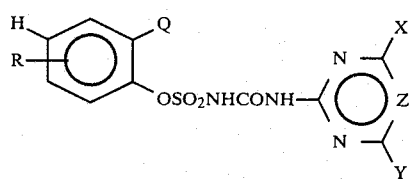

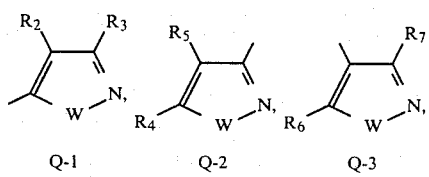

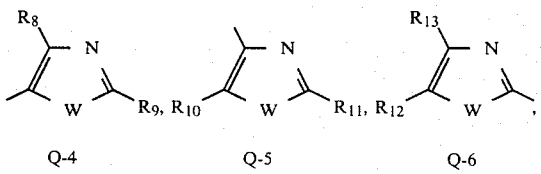

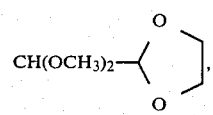

or

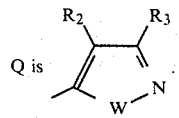

R is H, F, Cl, Br, $CH_3$, $CF_3$ or $OCH_3$;
W is O, S or $NR_1$;
$W_1$ is O or S;
$R_1$ is $C_1$–$C_3$ alkyl;
$R_2$, $R_3$, $R_4$, $R_5$, $R_8$, $R_9$, $R_{10}$, $R_{11}$, $R_{12}$, $R_{13}$, $R_{14}$, $R_{15}$, $R_{16}$, $R_{19}$, $R_{21}$, $R_{22}$, $R_{23}$, $R_{25}$ or $R_{27}$ are independently H, $CH_3$ or $C_2H_5$;
$R_6$, $R_7$, $R_{17}$, $R_{24}$ or $R_{26}$ are independently H or $CH_3$;
$R_{18}$ or $R_{20}$ are independently H or $C_1$–$C_3$ alkyl;
X is Cl, $CH_3$, $OCH_3$, $OCF_2H$ or $SCF_2H$;
Y is $CH_3$, $C_2H_5$, $OCH_3$, $OC_2H_5$, $OCH_2CF_3$, $CH_2OCH_3$, $$CH(OCH_3)_2 \text{—}\!\!\left\langle\begin{array}{c}O\\O\end{array}\right.,$$

or $GCF_2T$ where G is O or S and T is H, CHClF, CHBrF, $CF_2H$ or $CHFCF_3$; and Z is N;
provided that when X is Cl, then Y is $OCH_3$ or $OC_2H_5$; and their agriculturally suitable salts.

2. Compounds of claim 1 where R is H, W is O or S, and Q is Q-1 to Q-10, Q-15 and Q-16.

3. Compounds of claim 2 where $R_2$ to $R_{16}$, inclusive, are independently H or $CH_3$.

4. Compounds of claim 3 where

Q is 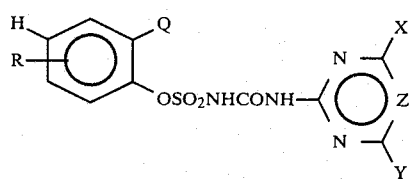

5. Compounds of claim 3 where

6. Compounds of claim 3 where Q is 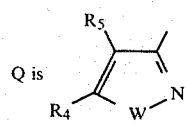

7. Compounds of claim 3 where Q is 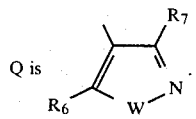

8. Compounds of claim 3 where Q is 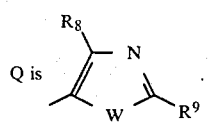

9. Compounds of claim 3 where Q is 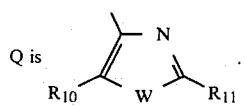

10. Compounds of claim 3 where Q is 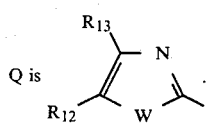

11. Compounds of claim 3 where Q is 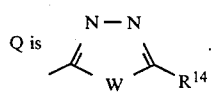

12. Compounds of claim 3 where Q is 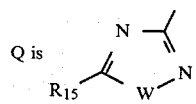

13. Compounds of claim 4 where Q is 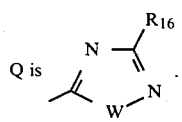

14. Compounds of claim 4 where Q is 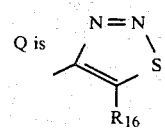

15. Compounds of claim 4 where Q is 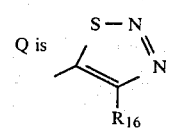

16. Compounds of claim 5 where W is O.
17. Compounds of claim 6 where W is O.
18. Compounds of claim 10 where W is O.
19. Compounds of claim 4 where X and Y are independently $CH_3$ or $OCH_3$.
20. The compound of claim 1 which is 2-(5-isoxazolyl)phenyl N-[(4-methoxy-6-methyl-1,3,5-triazin-2-yl)aminocarbonyl]sulfamate.
21. The compound of claim 1 which is 2-(3-isoxazolyl)phenyl N-[(4-methoxy-6-methyl-1,3,5-triazin-2-yl)phenyl N-[(4,6-dimethoxypyrimidin-2-yl)aminocarbonyl]sulfamate.
22. The compound of claim 1 which is 2-(1,3,4-oxadiazol-2-phenyl N-[(4-methoxy-6-methyl-1,3,5-triazin-2-yl)aminocarbonyl]sulfamate.
23. A composition suitable for controlling the growth of undesired vegetation which comprises an effective amount of a compound of claim 1 and at least one of the following: surfactant, solid or liquid diluent.
24. A composition suitable for controlling the growth of undesired vegetation which comprises an effective amount of a compound of claim 2 and at least one of the following: surfactant, solid or liquid diluent.
25. A composition suitable for controlling the growth of undesired vegetation which comprises an effective amount of a compound of claim 3 and at least one of the following: surfactant, solid or liquid diluent.
26. A composition suitable for controlling the growth of undesired vegetation which comprises an effective amount of a compound of claim 4 and at least one of the following: surfactant, solid or liquid diluent.
27. A composition suitable for controlling the growth of undesired vegetation which comprises an effective amount of a compound of claim 5 and at least one of the following: surfactant, solid or liquid diluent.
28. A composition suitable for controlling the growth of undesired vegetation which comprises an effective amount of a compound of claim 6 and at least one of the following: surfactant, solid or liquid diluent.
29. A composition suitable for controlling the growth of undesired vegetation which comprises an effective amount of a compound of claim 7 and at least one of the following: surfactant, solid or liquid diluent.
30. A method for controlling the growth of undesired vegetation which comprises applying to the locus to be protected an effective amount of a compound of claim 1.
31. A method for controlling the growth of undesired vegetation which comprises applying to the locus to be protected an effective amount of a compound of claim 2.

32. A method for controlling the growth of undesired vegetation which comprises applying to the locus to be protected an effective amount of a compound of claim 3.

33. A method for controlling the growth of undesired vegetation which comprises applying to the locus to be protected an effective amount of a compound of claim 4.

34. A method for controlling the growth of undesired vegetation which comprises applying to the locus to be protected an effective amount of a compound of claim 5.

35. A method for controlling the growth of undesired vegetation which comprises applying to the locus to be protected an effective amount of a compound of claim 6.

36. A method for controlling the growth of undesired vegetation which comprises applying to the locus to be protected an effective amount of a compound of claim 7.

* * * * *